(12) United States Patent
Sanford et al.

(10) Patent No.: US 10,443,101 B2
(45) Date of Patent: Oct. 15, 2019

(54) EXONIC SPLICING ENHANCERS AND EXONIC SPLICING SILENCERS

(71) Applicant: THE REGENTS OF THE UNIVERSITY OF CALIFORNIA, Oakland, CA (US)

(72) Inventors: Jeremy Sanford, Santa Cruz, CA (US); Timothy Steme-Weiler, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 18 days.

(21) Appl. No.: 15/706,485

(22) Filed: Sep. 15, 2017

(65) Prior Publication Data

US 2018/0119223 A1     May 3, 2018

Related U.S. Application Data

(63) Continuation of application No. 14/235,476, filed as application No. PCT/US2012/048427 on Jul. 27, 2012, now Pat. No. 9,765,398.

(60) Provisional application No. 61/512,827, filed on Jul. 28, 2011.

(51) Int. Cl.
   *C12N 15/113*        (2010.01)
   *C12Q 1/6883*        (2018.01)

(52) U.S. Cl.
   CPC .......... *C12Q 1/6883* (2013.01); *C12N 15/113* (2013.01); *C12N 2310/11* (2013.01); *C12N 2320/33* (2013.01)

(58) Field of Classification Search
None
See application file for complete search history.

(56) References Cited

U.S. PATENT DOCUMENTS

2009/0318362 A1    12/2009   Hansen et al.
2010/0297621 A1    11/2010   Weyrich et al.

FOREIGN PATENT DOCUMENTS

| EP | 1489185 | 12/2004 |
|---|---|---|
| RU | 2008110075 | 9/2009 |
| WO | 2007/022369 | 9/2009 |

OTHER PUBLICATIONS

PCT/US20121048427, International Search Report and Written Opinion dated Nov. 15, 2012, 6 pages.
Zhang X. H.-F. et al. RNA (2009). 15:367-376.
Schimpf S. et al. Hum Mutat 29(1), 106-112, 2008.
*Homo sapiens* optic atrophy 1 (autosomal dominant) (OPA1), transcript variant 1, mRNA, Locus: NM_015560 (Jul. 4, 2010) from www.ncbi.nlm.nih.gov, pp. 1-8.
*Homo sapiens* mRNA for KIAA0567 protein, partial cds, Locus: AB011139 (Apr. 10, 1998) from www.ncbi.nlm.nih.gov, pp. 1-3.
Hegele R.A. Arterioscler Thromb Vasc Biol. 2002;22:1058-1061.
Pennisi E. Science; Sep. 18, 1998; 281, 5384, pp. 1787-1789.
Lucentini J. The Scientist (Dec. 20, 2004), p. 20.

*Primary Examiner* — Sean McGarry
(74) *Attorney, Agent, or Firm* — Kilpatrick Townsend & Stockton LLP

(57) ABSTRACT

Compounds and methods for regulation of exonic splicing enhancers and exonic splicing silencers. Compounds include polynucleotides targeted to aberrant exonic splicing enhancers and exonic splicing silencers. Compounds and methods for the diagnosis of diseases and conditions associated with aberrant exonic splicing enhancers and exonic splicing silencers. Methods for identifying splicing-sensitive disease mutations, and functional RNA elements as targets for amelioration of aberrant pre-mRNA splicing.

5 Claims, 27 Drawing Sheets

Specification includes a Sequence Listing.

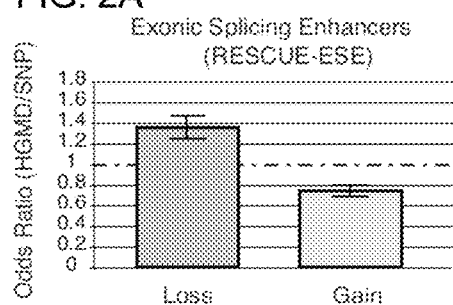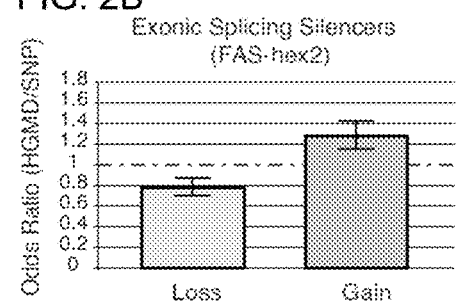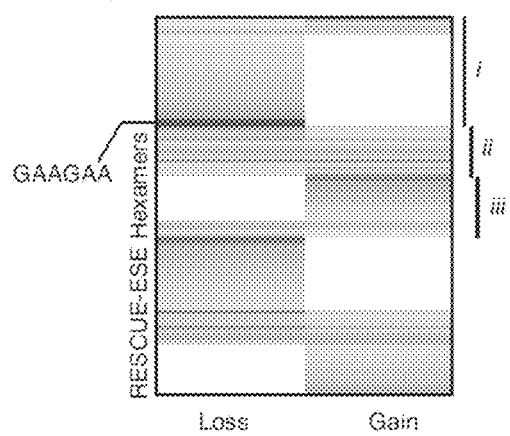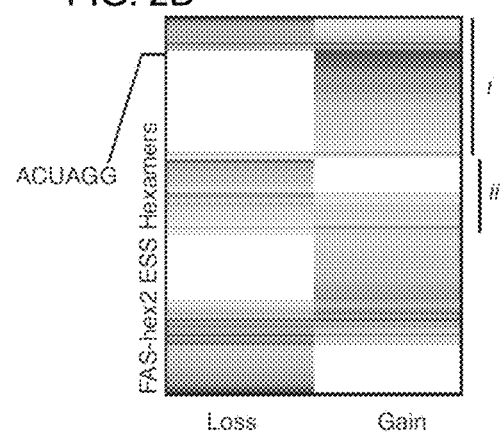

FIG. 7

|  | Disease-Mutation Count | Exon Count | Gene Count |
|---|---|---|---|
| 3-72 bp from SS | 27,681 | 7,974 | 1,760 |
| ESR Loss or Gain | 14,608 | 5,743 | 1,431 |
| Statistically Significant (5% FDR) | 7,154 | 3,747 | 1,055 |

FIG. 8

|  | SNP Count | Exon Count | Gene Count |
|---|---|---|---|
| >3 bp from SS | 8,438 | 7,338 | 4,529 |
| ESR loss or gain | 4,248 | 3,886 | 2,866 |

FIG. 9

| Hexamer | # of HGMD Mutations (Redundant) | # of Genes (Redundant) | # of HGMD Mutations (Non-Redundant) | # of Genes (Non-Redundant) | Binomial P-value |
|---|---|---|---|---|---|
| gaagaa | 56 | 33 | 51 | 31 | <2.22E-16 |
| agaaga | 35 | 27 | 28 | 20 | <2.22E-16 |
| gaaaac | 28 | 20 | 17 | 15 | <2.22E-16 |
| actcaa | 52 | 42 | 51 | 41 | <2.22E-16 |
| aaaaga | 45 | 28 | 42 | 26 | 1.11E-15 |
| tggaat | 90 | 56 | 85 | 53 | 1.73E-14 |
| ggatca | 51 | 36 | 50 | 35 | 6.28E-14 |
| aaacga | 51 | 44 | 46 | 39 | 6.28E-14 |
| actctg | 42 | 34 | 39 | 32 | 8.02E-14 |
| aagaag | 42 | 33 | 16 | 15 | 8.02E-14 |
| gagtaa | 29 | 24 | 23 | 19 | 1.19E-11 |
| agaaaa | 44 | 33 | 22 | 20 | 2.72E-10 |
| tcaaga | 58 | 38 | 57 | 37 | 5.34E-10 |
| gaagat | 34 | 28 | 27 | 23 | 3.01E-09 |
| gaaaga | 56 | 39 | 26 | 21 | 3.39E-09 |
| gaagac | 32 | 21 | 19 | 13 | 3.23E-08 |
| gatgaa | 46 | 30 | 36 | 23 | 5.96E-08 |
| acttca | 71 | 52 | 63 | 48 | 1.08E-07 |
| attgga | 52 | 33 | 39 | 29 | 1.12E-07 |
| caagaa | 52 | 43 | 19 | 19 | 1.12E-07 |
| ttcgaa | 45 | 39 | 33 | 30 | 1.48E-07 |
| aaggac | 38 | 26 | 30 | 20 | 1.55E-07 |
| aggaga | 58 | 42 | 50 | 39 | 1.61E-07 |
| tggaag | 73 | 53 | 52 | 40 | 1.50E-06 |
| cagaaa | 55 | 40 | 41 | 32 | 1.54E-06 |
| agcaga | 47 | 38 | 38 | 30 | 5.84E-06 |
| acgact | 34 | 27 | 20 | 13 | 6.58E-06 |
| aatgaa | 27 | 20 | 26 | 20 | 7.22E-06 |
| gaatca | 27 | 21 | 24 | 19 | 7.22E-06 |
| aaggag | 39 | 36 | 9 | 9 | 2.21E-05 |
| tgtgtt | 74 | 48 | 46 | 32 | 2.31E-05 |
| gatatg | 32 | 22 | 30 | 20 | 3.66E-05 |
| cgaaga | 18 | 13 | 8 | 7 | 4.10E-05 |
| cagatc | 50 | 40 | 41 | 35 | 4.72E-05 |
| tguaac | 44 | 36 | 43 | 35 | 4.98E-05 |
| gaaaaa | 31 | 26 | 17 | 14 | 8.26E-05 |
| cgaatg | 60 | 37 | 48 | 26 | 0.0001 |
| aagaaa | 54 | 38 | 10 | 9 | 0.0001 |
| aaccag | 48 | 39 | 35 | 28 | 0.0002 |
| gaagta | 30 | 20 | 21 | 18 | 0.0002 |
| atcaag | 42 | 37 | 25 | 24 | 0.0002 |
| gacgaa | 36 | 30 | 21 | 20 | 0.0002 |
| gagtag | 53 | 43 | 36 | 29 | 0.0002 |
| tgtgga | 121 | 83 | 78 | 55 | 0.0003 |
| gcagaa | 47 | 37 | 14 | 13 | 0.0003 |
| aaagac | 23 | 15 | 19 | 14 | 0.0003 |
| aaggt | 23 | 16 | 12 | 10 | 0.0003 |
| tgaagt | 41 | 28 | 32 | 24 | 0.0004 |
| actgga | 79 | 66 | 47 | 41 | 0.0004 |
| aaacca | 22 | 18 | 10 | 10 | 0.0007 |
| agaaag | 28 | 21 | 10 | 10 | 0.0008 |
| cgaaaa | 45 | 39 | 22 | 20 | 0.0009 |
| gatgag | 65 | 47 | 33 | 28 | 0.0018 |
| atcaga | 32 | 21 | 22 | 15 | 0.0026 |
| aactgg | 84 | 59 | 46 | 34 | 0.0030 |
| tcgaaa | 84 | 59 | 36 | 31 | 0.0030 |
| aagcag | 58 | 46 | 25 | 21 | 0.0038 |
| ttcgat | 78 | 48 | 16 | 15 | 0.0042 |
| atgaag | 31 | 25 | 9 | 9 | 0.0046 |
| caagat | 47 | 35 | 31 | 25 | 0.0049 |
| tgaagg | 36 | 33 | 22 | 20 | 0.0059 |
| atccaa | 30 | 23 | 26 | 22 | 0.0080 |
| gaaaga | 30 | 26 | 5 | 4 | 0.0080 |
| ggaggt | 71 | 48 | 33 | 25 | 0.0084 |
| ctacat | 45 | 37 | 27 | 23 | 0.0115 |
| agatga | 50 | 34 | 21 | 16 | 0.0119 |
| aatcaa | 18 | 15 | 9 | 7 | 0.0133 |
| gaaacg | 18 | 17 | 8 | 8 | 0.0133 |
| caatca | 44 | 27 | 33 | 20 | 0.0172 |
| tatgaa | 54 | 41 | 34 | 27 | 0.0174 |
| caaaag | 28 | 22 | 15 | 15 | 0.0219 |
| gaagta | 63 | 52 | 16 | 16 | 0.0229 |
| gcagaa | 58 | 46 | 28 | 23 | 0.0238 |

FIG. 10

| Hexamer | # of HGMD Mutations (Redundant) | # of Genes (Redundant) | # of HGMD Mutations (Non-Redundant) | # of Genes (Non-Redundant) | Binomial P-value |
|---|---|---|---|---|---|
| caagta | 67 | 57 | 60 | 52 | <2.22E-16 |
| atgaga | 103 | 86 | 103 | 86 | <2.22E-17 |
| cctgaa | 108 | 87 | 108 | 87 | <2.22E-18 |
| atcaag | 51 | 46 | 48 | 43 | 1.11E-15 |
| tcaaga | 43 | 43 | 31 | 31 | 9.77E-15 |
| aagaga | 27 | 23 | 27 | 23 | 7.49E-14 |
| ctgaaa | 99 | 85 | 68 | 61 | 1.29E-13 |
| gaigaaa | 25 | 24 | 21 | 21 | 2.86E-12 |
| caagaa | 56 | 49 | 43 | 38 | 3.56E-12 |
| aatgat | 76 | 63 | 59 | 50 | 4.50E-12 |
| tgaaag | 71 | 61 | 44 | 38 | 5.06E-12 |
| gaaigag | 42 | 32 | 28 | 24 | 1.13E-10 |
| agtgaa | 72 | 59 | 64 | 52 | 1.57E-10 |
| tgactg | 130 | 105 | 118 | 95 | 7.25E-10 |
| gatcaa | 34 | 31 | 27 | 25 | 1.83E-09 |
| aactga | 99 | 76 | 70 | 58 | 3.98E-08 |
| atgaaa | 31 | 28 | 26 | 25 | 6.54E-08 |
| tgaaac | 36 | 33 | 22 | 20 | 9.07E-08 |
| acaact | 33 | 31 | 31 | 30 | 1.82E-06 |
| aggaca | 64 | 58 | 57 | 52 | 2.03E-06 |
| ggatga | 32 | 29 | 29 | 26 | 4.70E-06 |
| gaagac | 32 | 28 | 13 | 12 | 4.70E-06 |
| atgaag | 43 | 34 | 42 | 37 | 3.51E-05 |
| ctacat | 43 | 38 | 37 | 30 | 3.51E-05 |
| gaaaag | 25 | 22 | 18 | 17 | 3.63E-05 |
| tactag | 50 | 44 | 44 | 38 | 8.20E-05 |
| catgaa | 24 | 18 | 15 | 14 | 9.23E-05 |
| acatga | 61 | 57 | 50 | 47 | 0.00014 |
| atgaag | 28 | 24 | 24 | 23 | 0.00015 |
| aagaac | 28 | 26 | 21 | 19 | 0.00015 |
| aaagtc | 28 | 27 | 18 | 18 | 0.00015 |
| atggat | 64 | 56 | 56 | 49 | 0.00021 |
| tgagaa | 97 | 83 | 60 | 58 | 0.00025 |
| gaaaga | 18 | 18 | 8 | 8 | 0.00029 |
| tatgaa | 63 | 47 | 51 | 39 | 0.00035 |
| agaaca | 63 | 54 | 40 | 36 | 0.00035 |
| actagg | 59 | 52 | 51 | 46 | 0.00038 |
| caagat | 55 | 52 | 33 | 32 | 0.00042 |
| aaccag | 47 | 41 | 43 | 39 | 0.00048 |
| aacaga | 39 | 35 | 29 | 26 | 0.00050 |
| actaca | 38 | 31 | 25 | 25 | 0.00091 |
| ggatga | 48 | 41 | 37 | 32 | 0.00211 |
| tggatc | 47 | 43 | 35 | 34 | 0.00340 |
| aagaag | 5 | 4 | 4 | 3 | 0.00435 |
| aactac | 39 | 28 | 25 | 18 | 0.00439 |
| aaagag | 19 | 19 | 13 | 13 | 0.00551 |
| aactac | 27 | 26 | 19 | 19 | 0.00574 |
| tggaat | 38 | 35 | 28 | 26 | 0.00716 |
| ggatca | 34 | 31 | 19 | 17 | 0.00817 |
| cagatc | 37 | 32 | 23 | 21 | 0.01142 |
| agatga | 47 | 42 | 12 | 12 | 0.01580 |
| agaaaa | 9 | 9 | 5 | 5 | 0.01660 |
| agacaa | 36 | 33 | 25 | 24 | 0.01779 |
| aactgg | 74 | 66 | 43 | 38 | 0.01944 |
| aaasag | 13 | 12 | 10 | 9 | 0.02081 |
| agigac | 60 | 51 | 36 | 31 | 0.02174 |
| actaga | 39 | 36 | 8 | 8 | 0.02262 |

FIG. 11

| Hexamer | # of HGMD Mutations (Redundant) | # of Genes (Redundant) | # of HGMD Mutations (Non-Redundant) | # of Genes (Non-Redundant) | Binomial P-value |
|---|---|---|---|---|---|
| gtgtgg | 85 | 58 | 172 | 85 | <2.22E-16 |
| gqtgtg | 92 | 49 | 84 | 58 | <2.22E-17 |
| tcctgg | 184 | 89 | 66 | 41 | <2.22E-18 |
| cctggg | 151 | 84 | 111 | 67 | 6.15E-14 |
| tccagg | 100 | 73 | 95 | 69 | 1.08E-13 |
| tgggga | 75 | 50 | 60 | 46 | 8.79E-13 |
| tgggtg | 73 | 47 | 50 | 31 | 5.78E-12 |
| agatgg | 82 | 49 | 69 | 43 | 2.28E-10 |
| tggggg | 91 | 68 | 67 | 53 | 3.49E-06 |
| ggtta | 20 | 17 | 17 | 15 | 1.65E-05 |
| aggtta | 8 | 6 | 8 | 6 | 1.75E-05 |
| tgatgg | 58 | 44 | 51 | 40 | 1.87E-05 |
| gtggtt | 28 | 22 | 22 | 18 | 6.16E-05 |
| ggctta | 17 | 10 | 13 | 8 | 0.00040 |
| gggagg | 76 | 47 | 42 | 32 | 0.00054 |
| ccacta | 21 | 14 | 18 | 12 | 0.00061 |
| ggttat | 21 | 13 | 15 | 11 | 0.00061 |
| agttig | 29 | 19 | 28 | 18 | 0.00073 |
| gtgggg | 40 | 35 | 31 | 27 | 0.00100 |
| taagtg | 11 | 8 | 9 | 6 | 0.00148 |
| gtgatg | 50 | 40 | 26 | 21 | 0.00161 |
| ttatgg | 27 | 21 | 21 | 20 | 0.00279 |
| tggtgg | 97 | 72 | 71 | 56 | 0.00595 |
| aatggg | 59 | 41 | 43 | 32 | 0.01152 |
| ttttgg | 42 | 28 | 31 | 22 | 0.01256 |
| gatggg | 42 | 32 | 18 | 14 | 0.01256 |
| gggtta | 4 | 4 | 2 | 2 | 0.01477 |
| tatggg | 31 | 21 | 19 | 15 | 0.01698 |
| ggttgg | 20 | 16 | 17 | 13 | 0.02036 |

FIG. 12

| Hexamer | # of HGMD Mutations (Redundant) | # of Genes (Redundant) | # of HGMD Mutations (Non-Redundant) | # of Genes (Non-Redundant) | Binomial P-value |
|---|---|---|---|---|---|
| actagg | 83 | 67 | 64 | 52 | <2.22E-16 |
| cttagg | 50 | 43 | 45 | 39 | <2.22E-16 |
| attagg | 39 | 34 | 37 | 36 | <2.22E-16 |
| taggta | 63 | 50 | 37 | 32 | <2.22E-16 |
| gtagtt | 37 | 36 | 62 | 49 | <2.22E-16 |
| gtaggt | 64 | 59 | 53 | 49 | <2.22E-16 |
| ctaggt | 63 | 54 | 46 | 41 | <2.22E-16 |
| agtagg | 84 | 74 | 60 | 57 | <2.22E-16 |
| tgtagg | 96 | 79 | 77 | 63 | <2.22E-16 |
| gattag | 34 | 25 | 29 | 20 | 1.11E-16 |
| tagtta | 21 | 20 | 18 | 18 | 2.22E-16 |
| ttaggt | 42 | 39 | 16 | 16 | 1.33E-15 |
| atagtt | 32 | 24 | 26 | 19 | 3.33E-15 |
| tactag | 55 | 48 | 33 | 31 | 6.20E-14 |
| agatta | 44 | 32 | 32 | 24 | 5.74E-12 |
| tagttt | 43 | 34 | 25 | 23 | 1.97E-11 |
| tagtgg | 50 | 40 | 48 | 39 | 2.10E-11 |
| tagtgt | 54 | 44 | 45 | 38 | 3.25E-10 |
| aagtga | 77 | 68 | 59 | 55 | 7.45E-10 |
| gtgtag | 53 | 48 | 29 | 28 | 8.71E-10 |
| ccacta | 46 | 40 | 40 | 36 | 1.58E-09 |
| gatagg | 22 | 22 | 19 | 19 | 3.58E-08 |
| tctagg | 60 | 49 | 46 | 38 | 6.51E-08 |
| agttag | 20 | 18 | 17 | 16 | 5.83E-07 |
| tttlag | 20 | 20 | 17 | 17 | 5.83E-07 |
| ttctag | 67 | 53 | 49 | 40 | 1.10E-06 |
| ctaggu | 56 | 50 | 30 | 28 | 1.35E-06 |
| gtcta | 32 | 30 | 18 | 16 | 3.27E-06 |
| tatagg | 31 | 26 | 22 | 19 | 8.34E-06 |
| agtgtt | 36 | 30 | 30 | 26 | 1.74E-05 |
| tagtat | 47 | 37 | 37 | 31 | 1.75E-05 |
| gtaagg | 40 | 35 | 37 | 32 | 5.35E-05 |
| ttagta | 16 | 14 | 8 | 8 | 8.81E-05 |
| ggtgtt | 28 | 27 | 17 | 17 | 0.00011 |
| tgtagt | 58 | 51 | 26 | 24 | 0.00024 |
| gcttag | 32 | 28 | 23 | 20 | 0.00036 |
| agtata | 32 | 27 | 13 | 13 | 0.00036 |
| gtaggg | 26 | 26 | 3 | 3 | 0.00056 |
| gtttg | 35 | 33 | 29 | 28 | 0.00148 |
| tttagg | 24 | 21 | 14 | 13 | 0.00242 |
| agtgta | 39 | 33 | 28 | 28 | 0.00248 |
| ggtag | 39 | 37 | 20 | 17 | 0.00248 |
| tgtag | 34 | 29 | 23 | 23 | 0.00264 |
| aggtaa | 37 | 32 | 19 | 16 | 0.00689 |
| tgtgg | 86 | 70 | 74 | 62 | 0.00759 |
| tgggtg | 17 | 17 | 15 | 15 | 0.00831 |
| ttagat | 22 | 21 | 13 | 12 | 0.00899 |
| ttagtg | 36 | 29 | 5 | 5 | 0.01108 |
| gtatag | 26 | 25 | 8 | 8 | 0.01486 |
| agatgg | 48 | 46 | 34 | 33 | 0.02093 |

FIG. 13

| Locus | Normal Wild Type 200mM | Normal Mutant 200mM | Loose Wild Type 200mM | Loose Mutant 200mM | Total | Description |
|---|---|---|---|---|---|---|
| gi|4506671|ref|NP_000 | 39.1 | 48.7 | 39.1 | 48.7 | 77.4 | ribosomal protein P2 [Homo sapiens] |
| gi|4504517|ref|NP_001 | 13.2 | 47.8 | 13.2 | 47.8 | 47.8 | heat shock 27kDa protein 1 [Homo sapiens] |
| gi|4757756|ref|NP_004 | 14.5 | 34.8 | 16.5 | 41 | 41 | annexin A2 isoform 2 [Homo sapiens] |
| gi|4504447|ref|NP_002 | 22.9 | 40.5 | 27 | 40.5 | 40.5 | heterogeneous nuclear ribonucleoprotein A2/B1 isoform A2 [Homo sapiens] |
| gi|20357552|ref|NP_00 | 15.1 | 31.3 | 15.1 | 31.3 | 35.3 | cortactin isoform a [Homo sapiens] |
| gi|10835063|ref|NP_00 | 12.6 | 33.3 | 12.6 | 33.3 | 33.3 | nucleophosmin 1 isoform 1 [Homo sapiens] |
| gi|5032051|ref|NP_005 | 17.9 | 32.5 | 17.9 | 32.5 | 32.5 | ribosomal protein S14 [Homo sapiens] |
| gi|16507237|ref|NP_00 | 15.6 | 18.2 | 18.3 | 20.5 | 31.7 | heat shock 70kDa protein 5 [Homo sapiens] |
| gi|5453854|ref|NP_006 | 12.1 | 23.3 | 18.5 | 31.5 | 31.5 | poly(rC) binding protein 1 [Homo sapiens] |
| gi|11939575|ref|NP_0 | 19.1 | 25.6 | 21.4 | 29.5 | 31.2 | keratin 1 [Homo sapiens] |
| gi|34932414|ref|NP_03 | 21.2 | 25.9 | 21.2 | 28.5 | 31 | non-POU domain containing, octamer-binding [Homo sapiens] |
| gi|14165439|ref|NP_00 | 13.6 | 30.2 | 13.6 | 30.2 | 30.2 | heterogeneous nuclear ribonucleoprotein K isoform a [Homo sapiens] |
| gi|4504277|ref|NP_003 | 29.4 | 29.4 | 29.4 | 29.4 | 29.4 | histone cluster 2, H2be [Homo sapiens] |
| gi|4885379|ref|NP_005 | 28.3 | 17.4 | 28.3 | 17.4 | 28.3 | histone cluster 1, H1e [Homo sapiens] |
| gi|40354192|ref|NP_00 | 18.2 | 21.2 | 21.1 | 22.8 | 27.7 | keratin 10 [Homo sapiens]; keratin 10; cytokeratin 10 [Homo sapiens] |
| gi|4885049|ref|NP_005 | 12.7 | 18.3 | 15.6 | 21.8 | 26.5 | cardiac muscle alpha actin 1 proprotein [Homo sapiens] |
| gi|14835233|ref|NP_0 | 12.4 | 17.8 | 12.4 | 17.8 | 26.3 | cell division cycle 10 isoform 1 [Homo sapiens] |
| gi|14141152|ref|NP_00 | 16.2 | 24.2 | 20.3 | 25.2 | 26.2 | heterogeneous nuclear ribonucleoprotein M isoform a [Homo sapiens] |
| gi|61743954|ref|NP_00 | 11.5 | 20.6 | 12.3 | 21.6 | 26.2 | AHNAK nucleoprotein isoform 1 [Homo sapiens] |
| gi|71361682|ref|NP_00 | 10.2 | 21.9 | 10.9 | 23.5 | 26.2 | nuclear mitotic apparatus protein 1 [Homo sapiens] |
| gi|41150665|ref|XP_37 | 13.7 | 23.7 | 13.7 | 26.1 | 26.1 | PREDICTED: similar to RPL13 protein isoform 1 [Homo sapiens] |
| gi|67189747|ref|NP_00 | 8 | 26 | 8 | 26 | 26 | ribosomal protein L6 [Homo sapiens] |
| gi|4505763|ref|NP_000 | 8.2 | 17.7 | 8.2 | 21.3 | 25.4 | phosphoglycerate kinase 1 [Homo sapiens] |
| gi|29788785|ref|NP_82 | 17.3 | 20.9 | 17.3 | 20.9 | 25.2 | tubulin, beta [Homo sapiens] |
| gi|4503471|ref|NP_001 | 9.3 | 22.3 | 9.3 | 24.5 | 24.7 | eukaryotic translation elongation factor 1 alpha 1 [Homo sapiens] |
| gi|4504809|ref|NP_002 | 15.3 | 16.4 | 15.3 | 16.4 | 24.5 | jun B proto-oncogene [Homo sapiens] |
| gi|15431290|ref|NP_00 | 7.9 | 24.2 | 7.9 | 24.2 | 24.2 | ribosomal protein L11 [Homo sapiens] |
| gi|19923969|ref|NP_61 | 5.8 | 23.8 | 5.8 | 23.8 | 23.8 | coiled-coil domain containing 124 [Homo sapiens] |
| gi|66346685|ref|NP_05 | 7.5 | 20.9 | 7.5 | 23.8 | 23.8 | SERPINE1 mRNA binding protein 1 isoform 4 [Homo sapiens] |
| gi|78000183|ref|NP_00 | 10.7 | 12.6 | 10.7 | 12.6 | 23.3 | ribosomal protein L14 [Homo sapiens] |
| gi|116256489|ref|NP_0 | 14.3 | 15.3 | 18.1 | 17.4 | 22.9 | septin 9 isoform c [Homo sapiens] |
| gi|5729877|ref|NP_006 | 12.5 | 20.9 | 13.8 | 21.7 | 22.9 | heat shock 70kDa protein 8 isoform 1 [Homo sapiens] |
| gi|14670356|ref|NP_00 | 8.9 | 17.1 | 11.2 | 18.8 | 22.8 | general transcription factor II, i isoform 4 [Homo sapiens] |
| gi|56549640|ref|NP_00 | 4.7 | 22.7 | 4.7 | 22.7 | 22.7 | septin 2 [Homo sapiens] |
| gi|114796640|ref|NP_0 | 8.1 | 14.7 | 8.1 | 18.1 | 22.6 | regulator of chromosome condensation 1 [Homo sapiens] |
| gi|27436948|ref|NP_73 | 9 | 15.6 | 9 | 20.8 | 22.4 | lamin A/C isoform 3 [Homo sapiens] |
| gi|46409270|ref|NP_99 | 12.2 | 22.4 | 12.2 | 22.4 | 22.4 | tubulin, alpha 3c [Homo sapiens] |
| gi|30089919|ref|NP_83 | 12.5 | 22.2 | 12.5 | 22.2 | 22.2 | DNA polymerase delta interacting protein 3 isoform 2 [Homo sapiens] |
| gi|14670268|ref|NP_00 | 11.3 | 17.1 | 11.3 | 17.1 | 21.8 | RD RNA-binding protein [Homo sapiens] |
| gi|17105394|ref|NP_00 | 16 | 16.7 | 16 | 16.7 | 21.8 | ribosomal protein L23a [Homo sapiens] |
| gi|4826998|ref|NP_005 | 8.1 | 21.8 | 8.1 | 21.8 | 21.8 | splicing factor proline/glutamine rich (polypyrimidine tract binding protein associated) [Homo sapiens] |
| gi|73760401|ref|NP_00 | 8.4 | 13.3 | 15.9 | 13.3 | 20.9 | thymopoietin isoform gamma [Homo sapiens] |
| gi|148833484|ref|NP_0 | 14.2 | 20.8 | 14.2 | 20.8 | 20.8 | poly(rC)-binding protein 2 isoform c [Homo sapiens] |
| gi|89027564|ref|XP_94 | 7 | 16.9 | 7 | 16.9 | 20.6 | PREDICTED: similar to Ribosomal protein L6 isoform 7 [Homo sapiens] |
| gi|4506625|ref|NP_000 | 16.9 | 10.8 | 16.9 | 10.8 | 20.3 | ribosomal protein L27a [Homo sapiens] |
| gi|4506743|ref|NP_001 | 18.8 | 13 | 18.8 | 13 | 20.2 | ribosomal protein S8 [Homo sapiens] |
| gi|47132620|ref|NP_00 | 15.8 | 14.9 | 17.2 | 16.3 | 20.2 | keratin 2 [Homo sapiens] |
| gi|16579885|ref|NP_00 | 7.7 | 10.3 | 9.8 | 14.8 | 20.1 | ribosomal protein L4 [Homo sapiens] |
| gi|21361657|ref|NP_00 | 7.5 | 7.7 | 17.2 | 10.1 | 20 | protein disulfide isomerase-associated 3 precursor [Homo sapiens] |
| gi|67946630|ref|NP_00 | 19.3 | 9.9 | 19.3 | 9.9 | 19.8 | ribosomal protein L9 [Homo sapiens] |
| gi|4557493|ref|NP_001 | 14.2 | 11.6 | 14.2 | 14.2 | 19.2 | cleavage stimulation factor subunit 2 [Homo sapiens] |
| gi|20127519|ref|NP_03 | 8.4 | 16.7 | 10.2 | 16.7 | 18.5 | TPX2, microtubule-associated protein homolog [Homo sapiens] |
| gi|62750354|ref|NP_95 | 8.9 | 15.9 | 8.9 | 18.4 | 18.4 | matrin 3 [Homo sapiens] |
| gi|30581135|ref|NP_00 | 8.8 | 14.3 | 9.6 | 14.3 | 18.3 | structural maintenance of chromosomes 1A [Homo sapiens] |
| gi|55956899|ref|NP_00 | 6.9 | 16.5 | 6.9 | 16.5 | 18.3 | keratin 9 [Homo sapiens] |
| gi|4885399|ref|NP_005 | 2.4 | 13.6 | 3.4 | 17.2 | 18.2 | structural maintenance of chromosomes 3 [Homo sapiens] |
| gi|6912676|ref|NP_036 | 9.1 | 11.2 | 11.8 | 16.4 | 18.1 | SKI-interacting protein [Homo sapiens] |
| gi|4758138|ref|NP_004 | 11.2 | 12.1 | 12.9 | 12.1 | 17.6 | DEAD (Asp-Glu-Ala-Asp) box polypeptide 5 [Homo sapiens] |
| gi|11067747|ref|NP_00 | 11.5 | 4.7 | 11.5 | 5.9 | 17.3 | CDC5-like [Homo sapiens] |
| gi|4506663|ref|NP_000 | 13.6 | 12.8 | 13.6 | 12.8 | 17.1 | ribosomal protein L8 [Homo sapiens] |
| gi|21218438|ref|NP_06 | 12.5 | 7.1 | 12.5 | 9.8 | 16.9 | GATA zinc finger domain containing 2B [Homo sapiens] |
| gi|4506619|ref|NP_000 | 14 | 16.6 | 14 | 16.6 | 16.6 | ribosomal protein L24 [Homo sapiens] |
| gi|46231942|ref|NP_0 | 6.4 | 13.1 | 8.3 | 13.1 | 16.1 | catenin, delta 1 isoform 1A [Homo sapiens] |
| gi|15011974|ref|NP_00 | 7.7 | 9.5 | 10.3 | 10.4 | 16.1 | rho/rac guanine nucleotide exchange factor 2 [Homo sapiens] |
| gi|15431295|ref|NP_15 | 10 | 16.1 | 10 | 16.1 | 16.1 | ribosomal protein L13 [Homo sapiens] |
| gi|57164977|ref|NP_00 | 7.1 | 11.2 | 8.8 | 11.9 | 16.1 | Treacher Collins-Franceschetti syndrome 1 isoform a [Homo sapiens] |
| gi|149588928|ref|NP_0 | 7.4 | 6.4 | 7.4 | 13.9 | 16 | SLAIN motif family, member 2 [Homo sapiens] |
| gi|5123454|ref|NP_005 | 10.6 | 13.7 | 10.6 | 13.7 | 15.9 | heat shock 70kDa protein 1A [Homo sapiens] |
| gi|38201710|ref|NP_00 | 6.7 | 10.2 | 6.7 | 11.7 | 15.4 | DEAD box polypeptide 17 isoform 1 [Homo sapiens] |
| gi|4506411|ref|NP_002 | 4.8 | 8.3 | 6.6 | 10.6 | 15.3 | Ran GTPase activating protein 1 [Homo sapiens] |
| gi|169211550|ref|XP_0 | 6.6 | 7.2 | 15.2 | 7.2 | 15.2 | PREDICTED: similar to septin 9 [Homo sapiens] |
| gi|24432016|ref|NP_07 | 5.1 | 10 | 5.1 | 10 | 15.1 | pre-mRNA cleavage factor I, 59 kDa subunit [Homo sapiens] |
| gi|22035579|ref|NP_66 | 9.6 | 12.4 | 9.8 | 12.6 | 14.8 | septin 6 isoform A [Homo sapiens] |
| gi|74136883|ref|NP_11 | 4 | 14.5 | 4 | 14.8 | 14.8 | heterogeneous nuclear ribonucleoprotein U isoform a [Homo sapiens] |
| gi|14389309|ref|NP_11 | 7.1 | 9.1 | 8.9 | 9.1 | 14.7 | tubulin alpha 6 [Homo sapiens] |
| gi|4506597|ref|NP_000 | 5.5 | 14.5 | 5.5 | 14.5 | 14.5 | ribosomal protein L12 [Homo sapiens] |
| gi|19923502|ref|NP_06 | 10 | 9.4 | 10 | 12.7 | 14.3 | GATA zinc finger domain containing 2A [Homo sapiens] |
| gi|45032499|ref|NP_003 | 9.3 | 8 | 9.3 | 10.7 | 14.1 | DEK oncogene [Homo sapiens] |
| gi|113429532|ref|XP_9 | 8.8 | 14 | 8.8 | 14 | 14 | PREDICTED: similar to ribosomal protein S10 [Homo sapiens] |

FIG. 13 (Cont.)

| | | | | | | |
|---|---|---|---|---|---|---|
| gi\|110556636\|ref\|NP_2 | 6.8 | 8.6 | 6.8 | 11.9 | 13.5 | tankyrase 1-binding protein 1 [Homo sapiens] |
| gi\|27363484\|ref\|NP_75 | 7.8 | 10.7 | 7.8 | 13.4 | 13.4 | E74-like factor 1 (ets domain transcription factor) [Homo sapiens] |
| gi\|4506753\|ref\|NP_003 | 7.9 | 10.7 | 7.9 | 13.4 | 13.4 | RuvB-like 1 [Homo sapiens] |
| gi\|45018879\|ref\|NP_001 | 10.4 | 13.1 | 10.4 | 13.1 | 13.1 | actin, gamma 1 propeptide [Homo sapiens] |
| gi\|4503529\|ref\|NP_001 | 5.7 | 9.9 | 5.7 | 13.1 | 13.1 | eukaryotic translation initiation factor 4A isoform 1 [Homo sapiens] |
| gi\|4506661\|ref\|NP_000 | 12.4 | 9.4 | 12.4 | 9.4 | 12.8 | ribosomal protein L7a [Homo sapiens] |
| gi\|82546824\|ref\|NP_00 | 8.7 | 3.3 | 8.7 | 5.3 | 12.8 | forkhead box K1 [Homo sapiens] |
| gi\|116063573\|ref\|NP_0 | 8 | 7.5 | 9.9 | 7.5 | 12.7 | filamin A, alpha isoform 1 [Homo sapiens] |
| gi\|119395716\|ref\|NP_0 | 12.7 | 8.3 | 12.7 | 8.3 | 12.7 | forkhead box C1 [Homo sapiens] |
| gi\|29171753\|ref\|NP_80 | 5.1 | 9.2 | 5.1 | 10.3 | 12.6 | PTPRF interacting protein alpha 1 [Homo sapiens] |
| gi\|33286422\|ref\|NP_87 | 12.2 | 8.1 | 12.2 | 8.1 | 12.6 | pyruvate kinase, muscle isoform 2 [Homo sapiens] |
| gi\|40254978\|ref\|NP_11 | 5.1 | 9.9 | 7.2 | 12.6 | 12.6 | FIP1-like 1 [Homo sapiens] |
| gi\|55770864\|ref\|NP_00 | 11.3 | 12.5 | 11.3 | 12.5 | 12.5 | THO complex 4 [Homo sapiens] |
| gi\|5729730\|ref\|NP_006 | 4 | 12.3 | 4 | 12.3 | 12.3 | apoptosis inhibitor 5 [Homo sapiens] |
| gi\|4505117\|ref\|NP_003 | 7.1 | 8.5 | 7.1 | 8.5 | 12.2 | methyl-CpG binding domain protein 2 isoform 1 [Homo sapiens] |
| gi\|154355000\|ref\|NP_0 | 3 | 7.3 | 3 | 10.7 | 12.1 | KH-type splicing regulatory protein (FUSE binding protein 2) [Homo sapiens] |
| gi\|148596949\|ref\|NP_0 | 5.3 | 8.4 | 6.6 | 8.6 | 12 | nucleolar and coiled-body phosphoprotein 1 [Homo sapiens] |
| gi\|42734503\|ref\|NP_97 | 1.6 | 8.1 | 1.6 | 12 | 12 | membrane component chromosome 11 surface marker 1 isoform 2 [Homo sapiens] |
| gi\|5031973\|ref\|NP_005 | 8.6 | 8.9 | 8.6 | 8.9 | 11.8 | protein disulfide isomerase-associated 6 [Homo sapiens] |
| gi\|169211155\|ref\|XP_0 | 9.5 | 6.2 | 9.5 | 8.3 | 11.5 | PREDICTED: similar to Karyopherin alpha 2 (RAG cohort 1, importin alpha 1) isoform 1 [Homo sapiens] |
| gi\|4505317\|ref\|NP_002 | 2.5 | 10.6 | 3.3 | 10.6 | 11.5 | protein phosphatase 1, regulatory (inhibitor) subunit 12A [Homo sapiens] |
| gi\|22538461\|ref\|NP_00 | 4.7 | 8.9 | 4.7 | 9.9 | 11.4 | nuclear receptor co-repressor 1 [Homo sapiens] |
| gi\|45822771\|ref\|NP_05 | 2.6 | 7.2 | 4.2 | 7.2 | 11.4 | autoantigen RCD8 [Homo sapiens] |
| gi\|6005830\|ref\|NP_009 | 5.5 | 7 | 7.4 | 7 | 11.3 | plakophilin 3 [Homo sapiens] |
| gi\|14141170\|ref\|NP_00 | 5.1 | 11.1 | 5.1 | 11.1 | 11.1 | metastasis-associated protein 2 [Homo sapiens] |
| gi\|24308179\|ref\|NP_06 | 9.4 | 9.7 | 9.4 | 9.7 | 11.1 | CTTNBP2 N-terminal like [Homo sapiens] |
| gi\|27477136\|ref\|NP_06 | 4.7 | 6.2 | 5.9 | 11 | 11 | zinc finger antiviral protein isoform 1 [Homo sapiens] |
| gi\|21361397\|ref\|NP_03 | 10.9 | 5.1 | 10.9 | 5.1 | 10.9 | Rac GTPase activating protein 1 [Homo sapiens] |
| gi\|38201625\|ref\|NP_93 | 1.9 | 6.7 | 1.9 | 9.8 | 10.9 | eukaryotic translation initiation factor 4 gamma, 1 isoform 3 [Homo sapiens] |
| gi\|5453994\|ref\|NP_006 | 5.5 | 5.2 | 5.5 | 5.2 | 10.8 | RAD21 homolog [Homo sapiens] |
| gi\|112807226\|ref\|NP_0 | 4.6 | 5.2 | 7 | 5.2 | 10.5 | hypothetical protein LOC91748 [Homo sapiens] |
| gi\|109255228\|ref\|NP_0 | 1.6 | 8.3 | 1.6 | 9.5 | 10.4 | centrosomal protein 170kDa isoform alpha [Homo sapiens] |
| gi\|57863301\|ref\|NP_05 | 4.2 | 5.8 | 4.2 | 6.8 | 10.3 | CLIP-associating protein 2 [Homo sapiens] |
| gi\|4507555\|ref\|NP_003 | 6.6 | 2.3 | 7.6 | 4.9 | 10.2 | thymopoietin isoform alpha [Homo sapiens] |
| gi\|5730027\|ref\|NP_006 | 8.6 | 4.5 | 10.2 | 9.9 | 10.2 | KH domain containing, RNA binding, signal transduction associated 1 [Homo sapiens] |
| gi\|119395754\|ref\|NP_0 | 4.4 | 9.8 | 4.4 | 9.8 | 9.8 | keratin 5 [Homo sapiens] |
| gi\|19913363\|ref\|NP_00 | 2.7 | 8.1 | 2.7 | 9.8 | 9.8 | Wolf-Hirschhorn syndrome candidate 2 protein [Homo sapiens] |
| gi\|5032179\|ref\|NP_005 | 4.1 | 4 | 4.1 | 7.5 | 9.6 | tripartite motif-containing 28 protein [Homo sapiens] |
| gi\|19924131\|ref\|NP_59 | 1.9 | 8.4 | 1.9 | 8.4 | 9.5 | RAD50 homolog isoform 2 [Homo sapiens] |
| gi\|4504919\|ref\|NP_002 | 5.4 | 9.5 | 5.4 | 9.5 | 9.5 | keratin 8 [Homo sapiens]; keratin 8; cytokeratin 8; keratin, type II cytoskeletal 8 [Homo sapiens] |
| gi\|5031755\|ref\|NP_005 | 4.3 | 5.1 | 4.3 | 9.5 | 9.5 | heterogeneous nuclear ribonucleoprotein R isoform 2 [Homo sapiens] |
| gi\|50658063\|ref\|NP_00 | 3.5 | 8.1 | 3.5 | 8.1 | 9.5 | SMC4 structural maintenance of chromosomes 4-like 1 [Homo sapiens] |
| gi\|18375619\|ref\|NP_54 | 5.9 | 7.5 | 5.9 | 7.5 | 9.4 | death inducer-obliterator 1 isoform a [Homo sapiens] |
| gi\|4507457\|ref\|NP_003 | 7.4 | 7.2 | 7.4 | 7.2 | 9.3 | transferrin receptor [Homo sapiens] |
| gi\|7662274\|ref\|NP_055 | 5.8 | 9.2 | 5.8 | 9.2 | 9.2 | epidermal Langerhans cell protein LCP1 [Homo sapiens] |
| gi\|10947135\|ref\|NP_00 | 2.9 | 5.7 | 4.6 | 5.7 | 9 | ATP-binding cassette, sub-family F, member 1 isoform b [Homo sapiens] |
| gi\|116812577\|ref\|NP_0 | 6.6 | 8.9 | 6.6 | 8.9 | 8.9 | LUC7-like 2 [Homo sapiens] |
| gi\|103472005\|ref\|NP_0 | 2.1 | 5.9 | 2.5 | 7 | 8.8 | antigen identified by monoclonal antibody Ki-67 [Homo sapiens] |
| gi\|42518070\|ref\|NP_00 | 2.3 | 6.4 | 2.3 | 8.8 | 8.8 | tight junction protein 2 (zona occludens 2) isoform 1 [Homo sapiens] |
| gi\|38683860\|ref\|NP_00 | 3.1 | 6.2 | 3.1 | 7.5 | 8.7 | insulin receptor substrate 2 [Homo sapiens] |
| gi\|31657094\|ref\|NP_06 | 7 | 4.8 | 7 | 4.8 | 8.6 | anillin, actin binding protein [Homo sapiens] |
| gi\|38044290\|ref\|NP_06 | 4.2 | 6.2 | 4.2 | 8.6 | 8.6 | zinc finger, CCHC domain containing 8 [Homo sapiens] |
| gi\|28559039\|ref\|NP_00 | 2.8 | 5.1 | 2.8 | 7.7 | 8.5 | mediator complex subunit 1 [Homo sapiens] |
| gi\|47519675\|ref\|NP_11 | 3.5 | 6 | 4.4 | 6 | 8.5 | microtubule-associated protein 4 isoform 2 [Homo sapiens] |
| gi\|5454064\|ref\|NP_006 | 4.9 | 4.3 | 4.9 | 6.1 | 7.9 | RNA binding motif protein 14 [Homo sapiens] |
| gi\|98986457\|ref\|NP_00 | 5.7 | 3.9 | 7.2 | 5.4 | 7.9 | host cell factor 1 [Homo sapiens] |
| gi\|21040371\|ref\|NP_00 | 5.6 | 4.2 | 5.6 | 4.2 | 7.5 | DEAD (Asp-Glu-Ala-Asp) box polypeptide 39 [Homo sapiens] |
| gi\|31543983\|ref\|NP_11 | 5.6 | 5.6 | 5.6 | 5.6 | 7.5 | ADP-ribosylation factor GTPase activating protein 2 [Homo sapiens] |
| gi\|4503659\|ref\|NP_001 | 7.5 | 7.5 | 7.5 | 7.5 | 7.5 | ubiquitin-like protein fubi and ribosomal protein S30 precursor [Homo sapiens] |
| gi\|5667633\|ref\|NP_06 | 2.9 | 4.7 | 3.2 | 6 | 7.4 | RAP1 interacting factor 1 [Homo sapiens] |
| gi\|6885193\|ref\|NP_005 | 7.3 | 1.7 | 7.3 | 1.7 | 7.3 | AT rich interactive domain 3A (BRIGHT- like) protein [Homo sapiens] |
| gi\|116256445\|ref\|NP_0 | 3.1 | 4 | 3.1 | 5.8 | 7.2 | nuclear receptor co-repressor 2 isoform 2 [Homo sapiens] |
| gi\|42476299\|ref\|NP_05 | 4.5 | 4.2 | 4.5 | 4.2 | 7.2 | trinucleotide repeat containing 15 isoform b [Homo sapiens] |
| gi\|44888822\|ref\|NP_05 | 2.7 | 6.2 | 2.7 | 6.2 | 7.2 | hypothetical protein LOC23248 [Homo sapiens] |
| gi\|48255889\|ref\|NP_00 | 5.7 | 3.4 | 5.7 | 3.4 | 7.2 | protein kinase C substrate 80K-H isoform 1 [Homo sapiens] |
| gi\|7657385\|ref\|NP_055 | 7.2 | 3 | 7.2 | 5.4 | 7.2 | CCR4-NOT transcription complex, subunit 2 [Homo sapiens] |
| gi\|148277037\|ref\|NP_0 | 3.7 | 3.3 | 3.7 | 3.3 | 7.1 | AP2 associated kinase 1 [Homo sapiens] |
| gi\|5453830\|ref\|NP_006 | 3.6 | 5.4 | 3.6 | 5.4 | 6.8 | origin recognition complex, subunit 2 [Homo sapiens] |
| gi\|31581524\|ref\|NP_05 | 2.9 | 2.7 | 2.9 | 3.8 | 6.7 | condon-bleu homolog [Homo sapiens] |
| gi\|4505101\|ref\|NP_003 | 3.3 | 3.1 | 3.6 | 4.5 | 6.7 | microtubule-associated protein 7 [Homo sapiens] |
| gi\|35493811\|ref\|NP_90 | 6 | 3.2 | 6 | 3.2 | 6.4 | RNA binding motif protein 39 isoform a [Homo sapiens] |
| gi\|40018640\|ref\|NP_07 | 3.8 | 6.4 | 3.8 | 6.4 | 6.4 | parafibromin [Homo sapiens] |
| gi\|14326455\|ref\|NP_00 | 3.1 | 3 | 3.7 | 3.5 | 6.2 | chromodomain helicase DNA binding protein 8 [Homo sapiens] |
| gi\|169168349\|ref\|XP_0 | 4.2 | 3.2 | 4.2 | 3.2 | 6.2 | PREDICTED: similar to RNA-binding protein 27 (RNA-binding motif protein 27) [Homo sapiens] |
| gi\|156652968\|ref\|NP_0 | 2.4 | 6.1 | 2.4 | 6.1 | 6.1 | poly (ADP-ribose) polymerase family, member 1 [Homo sapiens] |
| gi\|7662018\|ref\|NP_055 | 1 | 5.1 | 1 | 6.1 | 6.1 | PHD finger protein 3 [Homo sapiens] |

FIG. 13 (Cont.)

| ID | | | | | | Description |
|---|---|---|---|---|---|---|
| gi\|56549696\|ref\|NP_05 | 3.9 | 2.1 | 3.9 | 3.2 | 6 | E1A binding protein p400 [Homo sapiens] |
| gi\|112382250\|ref\|NP_0 | 2.4 | 3.3 | 2.4 | 3.9 | 5.7 | spectrin, beta, non-erythrocytic 1 isoform 1 [Homo sapiens] |
| gi\|37620163\|ref\|NP_06 | 2.9 | 3.7 | 2.9 | 5 | 5.7 | ANKHD1-EIF4EBP3 protein [Homo sapiens] |
| gi\|57164942\|ref\|NP_00 | 3 | 4 | 3 | 4 | 5.7 | colonic and hepatic tumor over-expressed protein isoform a [Homo sapiens] |
| gi\|14149661\|ref\|NP_05 | 3 | 2.6 | 3 | 3.9 | 5.6 | RAB6-interacting protein 2 isoform alpha [Homo sapiens] |
| gi\|42558279\|ref\|NP_81 | 5.6 | 5.6 | 5.6 | 5.6 | 5.6 | tubulin, beta 8 [Homo sapiens] |
| gi\|48762942\|ref\|NP_00 | 3.5 | 2.3 | 4.4 | 3.6 | 5.6 | huntingtin interacting protein-1-related [Homo sapiens] |
| gi\|76573811\|ref\|NP_055 | 5.2 | 5.6 | 5.2 | 5.6 | 5.6 | PRP19/PSO4 pre-mRNA processing factor 19 homolog [Homo sapiens] |
| gi\|13699824\|ref\|NP_00 | 2.3 | 4.5 | 2.3 | 4.5 | 5.4 | kinesin family member 11 [Homo sapiens] |
| gi\|13491166\|ref\|NP_05 | 2.8 | 5.3 | 2.8 | 5.3 | 5.3 | pontin 1 isoform 2 [Homo sapiens] |
| gi\|57164405\|ref\|NP_20 | 3 | 1.7 | 3 | 3.8 | 5.3 | tetratricopeptide repeat, ankyrin repeat and coiled-coil containing 1 [Homo sapiens] |
| gi\|113430845\|ref\|XP_0 | 1.4 | 3.5 | 2.2 | 3.8 | 5.2 | PREDICTED: similar to DNA dependent protein kinase catalytic subunit [Homo sapiens] |
| gi\|19743813\|ref\|NP_00 | 3 | 3.9 | 3 | 3.9 | 5.1 | integrin beta 1 isoform 1A precursor [Homo sapiens] |
| gi\|115298682\|ref\|NP_0 | 1.2 | 3.7 | 1.2 | 4 | 4.9 | HBxAg transactivated protein 2 [Homo sapiens] |
| gi\|58530842\|ref\|NP_00 | 1.9 | 1.7 | 1.9 | 3.6 | 4.9 | desmoplakin isoform II [Homo sapiens] |
| gi\|14155142\|ref\|NP_0 | 1.3 | 3 | 1.7 | 3 | 4.7 | nuclear pore complex-associated protein TPR [Homo sapiens] |
| gi\|41281521\|ref\|NP_05 | 2.4 | 3.4 | 2.4 | 3.4 | 4.4 | non-SMC condensin I complex, subunit D2 [Homo sapiens] |
| gi\|6317661\|ref\|NP_07 | 1.1 | 4.4 | 1.1 | 4.4 | 4.4 | modulator of estrogen induced transcription isoform a [Homo sapiens] |
| gi\|6678271\|ref\|NP_031 | 4.3 | 4.3 | 4.3 | 4.3 | 4.3 | TAR DNA binding protein [Homo sapiens] |
| gi\|23173757\|ref\|NP_5 | 4.1 | 4.2 | 4.1 | 4.2 | 4.2 | RAVER1 [Homo sapiens] |
| gi\|21237805\|ref\|NP_00 | 1.7 | 4.2 | 1.7 | 4.2 | 4.2 | SWI/SNF-related matrix-associated actin-dependent regulator of chromatin e2 isoform a [Homo sapiens] |
| gi\|116686122\|ref\|NP_0 | 2.2 | 4.1 | 3.3 | 4.1 | 4.1 | kinesin family member 4 [Homo sapiens] |
| gi\|45356151\|ref\|NP_05 | 2.3 | 3 | 3.6 | 3 | 4.1 | non-SMC condensin II complex, subunit D3 [Homo sapiens] |
| gi\|49192855\|ref\|NP_0 | 3.1 | 2.2 | 3.1 | 2.2 | 3.9 | hypothetical protein LOC84726 [Homo sapiens] |
| gi\|150418007\|ref\|NP_0 | 1.4 | 2.9 | 1.4 | 3.5 | 3.9 | RAN binding protein 2 [Homo sapiens] |
| gi\|51479160\|ref\|NP_00 | 2.4 | 2.7 | 2.4 | 2.7 | 3.8 | ataxin 2 [Homo sapiens] |
| gi\|9966881\|ref\|NP_065 | 3.1 | 3.8 | 3.1 | 3.8 | 3.8 | nucleoporin 107kDa [Homo sapiens] |
| gi\|63054866\|ref\|NP_06 | 2.5 | 3 | 2.5 | 3 | 3.7 | leucine rich repeat containing 16 [Homo sapiens] |
| gi\|51747351\|ref\|NP_006 | 3.6 | 3.6 | 3.6 | 3.6 | 3.6 | tubulin, beta, 2 [Homo sapiens] |
| gi\|124378039\|ref\|NP_0 | 2 | 1.2 | 2.4 | 2.2 | 3.4 | SEC16 homolog A [Homo sapiens] |
| gi\|58761546\|ref\|NP_05 | 3.4 | 3.4 | 3.4 | 3.4 | 3.4 | amine oxidase (flavin containing) domain 2 isoform b [Homo sapiens] |
| gi\|8719635\|ref\|NP_00 | 3.3 | 3.3 | 3.3 | 3.3 | 3.3 | DEAD/H (Asp-Glu-Ala-Asp/His) box polypeptide 3 [Homo sapiens] |
| gi\|33946327\|ref\|NP_00 | 1.7 | 1.7 | 1.7 | 2.3 | 3.2 | nucleoporin 214kDa [Homo sapiens] |
| gi\|54607053\|ref\|NP_00 | 1.1 | 3 | 1.1 | 3.1 | 3.1 | GCN1 general control of amino-acid synthesis 1-like 1 [Homo sapiens] |
| gi\|7705373\|ref\|NP_057 | 1.4 | 3 | 1.4 | 3 | 3 | LIM domain and actin binding 1 isoform b [Homo sapiens] |
| gi\|18375630\|ref\|NP_54 | 2.8 | 1.6 | 2.8 | 1.6 | 2.9 | HLA-B associated transcript-3 isoform b [Homo sapiens] |
| gi\|42716275\|ref\|NP_0 | 1.1 | 2.2 | 1.1 | 2.8 | 2.8 | CCR4-NOT transcription complex, subunit 1 isoform a [Homo sapiens] |
| gi\|51599156\|ref\|NP_00 | 1.6 | 2.4 | 2 | 2.4 | 2.8 | chromodomain helicase DNA binding protein 4 [Homo sapiens] |
| gi\|156766050\|ref\|NP_6 | 1.6 | 1.2 | 1.6 | 1.2 | 2.2 | AHNAK nucleoprotein 2 [Homo sapiens] |
| gi\|10225353\|ref\|NP_0 | 1.2 | 1.6 | 1.2 | 1.6 | 1.6 | diaphanous homolog 3 isoform a [Homo sapiens] |
| gi\|61676188\|ref\|NP_11 | 1.6 | 1.3 | 1.6 | 1.1 | 1.6 | HECT, UBA and WWE domain containing 1 [Homo sapiens] |

FIG. 14

| | Normal | | Loose' | | | |
|---|---|---|---|---|---|---|
| Locus | Wild Type 200mM | Mutant 200mM | Wild Type 200mM | Mutant 200mM | Total | Description |
| gi\|28173560\|ref\|NP_77 | | 24.3 | 11.7 | 31.1 | 31.1 | histone cluster 4, H4 [Homo sapiens] |
| gi\|10645195\|ref\|NP_06 | 23.8 | 6.9 | 23.8 | | 23.8 | histone cluster 1, H2ae [Homo sapiens] |
| gi\|38327552\|ref\|NP_93 | | 19.1 | 6 | 19.1 | 19.1 | Ras-GTPase-activating protein SH3-domain-binding protein [Homo sapiens] |
| gi\|169194577\|ref\|XP_0 | | 11 | 16.6 | 16 | 17.2 | PREDICTED: similar to mCG4465, partial [Homo sapiens] |
| gi\|89035540\|ref\|XP_94 | 6.9 | 14.3 | 6.9 | | 14.3 | PREDICTED: similar to 24 kD highly basic protein isoform 1 [Homo sapiens] |
| gi\|41327773\|ref\|NP_05 | 10.1 | 2.1 | 13.2 | | 14.2 | DEAD (Asp-Glu-Ala-Asp) box polypeptide 46 [Homo sapiens] |
| gi\|20127479\|ref\|NP_00 | 11.5 | 2.6 | 11.5 | | 12.8 | RNA binding motif protein 10 isoform 1 [Homo sapiens] |
| gi\|76573649\|ref\|NP_055 | 9.4 | 6.8 | 9.4 | | 12.5 | tropomodulin 3 (ubiquitous) [Homo sapiens] |
| gi\|169170622\|ref\|XP_0 | 12.1 | 12.1 | 12.1 | | 12.1 | PREDICTED: hypothetical protein [Homo sapiens] |
| gi\|14327896\|ref\|NP_11 | 7.9 | 6.5 | 7.9 | | 10.4 | cyclin B1 [Homo sapiens] |
| gi\|21914927\|ref\|NP_06 | 8.2 | 3 | 8.2 | | 9.7 | helicase, lymphoid-specific [Homo sapiens] |
| gi\|10863997\|ref\|NP_00 | 4.9 | 3.6 | 7 | | 8.5 | polypyrimidine tract binding protein 1 [Homo sapiens] |
| gi\|25777671\|ref\|NP_00 | 4.6 | 3.6 | 6 | | 7.9 | protein phosphatase 1, regulatory subunit 10 [Homo sapiens] |
| gi\|31543397\|ref\|NP_62 | 7.9 | 3.6 | 7.9 | | 7.9 | phosphoglycerate kinase 2 [Homo sapiens] |
| gi\|6754472\|ref\|NP_004 | 7.1 | 2.5 | 7.1 | | 7.1 | kinesin family member 23 isoform 2 [Homo sapiens] |
| gi\|11559929\|ref\|NP_05 | 4.2 | 2.6 | 4.2 | | 6.9 | coatomer protein complex, subunit gamma 1 [Homo sapiens] |
| gi\|39725634\|ref\|NP_05 | 4.3 | 2.1 | 5.6 | | 6.8 | la related protein isoform 1 [Homo sapiens] |
| gi\|21493031\|ref\|NP_65 | 3.6 | 3.3 | 4.7 | | 6 | A-kinase anchor protein 13 isoform 3 [Homo sapiens] |
| gi\|15503621\|ref\|NP_0 | 5.6 | 3.3 | 5.6 | | 5.6 | PDS5, regulator of cohesion maintenance, homolog A isoform 2 [Homo sapiens] |
| gi\|100913206\|ref\|NP_0 | 2 | 1.4 | 4.4 | | 5.2 | DEAH (Asp-Glu-Ala-His) box polypeptide 9 [Homo sapiens] |
| gi\|154759259\|ref\|NP_0 | 4.4 | 1 | 4.4 | | 4.9 | spectrin, alpha, non-erythrocytic 1 (alpha-fodrin) [Homo sapiens] |
| gi\|19718731\|ref\|NP_49 | 3.3 | 1.9 | 4.2 | | 4.2 | bromodomain-containing protein 4 isoform long [Homo sapiens] |
| gi\|38372909\|ref\|NP_05 | 2.6 | 1.4 | 2.6 | | 3.9 | jumonji domain containing 1B [Homo sapiens] |
| gi\|38620745\|ref\|NP_05 | 1.9 | 1.8 | 1.9 | | 3.7 | pre-rRNA cleavage complex II protein Pes1 [Homo sapiens] |
| gi\|4505895\|ref\|NP_002 | 3.7 | 3.7 | 3.7 | | 3.7 | pleiotropic regulator 1 (PRL1 homolog, Arabidopsis) [Homo sapiens] |
| gi\|45439327\|ref\|NP_0 | 3 | 1.8 | 3 | | 3.6 | periplakin [Homo sapiens] |
| gi\|41327769\|ref\|NP_05 | 2.7 | 1.6 | 2.7 | | 2.7 | Rho-specific guanine nucleotide exchange factor p114 [Homo sapiens] |
| gi\|31652242\|ref\|NP_85 | 1.2 | 1.1 | 1.2 | | 2.3 | transcription factor 20 isoform 2 [Homo sapiens] |

FIG. 15

| Locus | Normal Wild Type 200mM | Normal Mutant 200mM | Loose' Wild Type 200mM | Loose' Mutant 200mM | Total | Description |
|---|---|---|---|---|---|---|
| gi|45827708|ref|NP_99 | 10 |  | 10 | 14.1 | 19.4 | quaking homolog, KH domain RNA binding isoform HQK-6 [Homo sapiens] |
| gi|88953883|ref|XP_93 | 10.6 |  | 10.6 | 12 | 17.3 | PREDICTED: similar to heterogeneous nuclear ribonucleoprotein A1 [Homo sapiens] |
| gi|58761486|ref|NP_00 | 4 |  | 4 | 10.7 | 14.7 | chaperonin containing TCP1, subunit 3 isoform b [Homo sapiens] |
| gi|4826659|ref|NP_004 | 7.4 |  | 7.4 | 10.7 | 14.3 | F-actin capping protein beta subunit [Homo sapiens] |
| gi|169206894|ref|XP_0 | 6.1 |  | 6.1 | 13.6 | 13.6 | PREDICTED: similar to S19 ribosomal protein [Homo sapiens] |
| gi|24308075|ref|NP_05 | 5.5 |  | 7.5 | 4.7 | 12.3 | RAB11 family interacting protein 5 (class I) [Homo sapiens] |
| gi|44636778|ref|NP_00 | 6 |  | 7.4 | 4.7 | 12.1 | poly(A) binding protein, cytoplasmic 1 [Homo sapiens] |
| gi|17402909|ref|NP_03 | 3.7 |  | 3.7 | 4.3 | 8 | tripartite motif protein TRIM29 [Homo sapiens] |
| gi|7706751|ref|NP_057 | 6 |  | 6 | 6 | 6 | tubulin, gamma 2 [Homo sapiens] |
| gi|105990514|ref|NP_0 | 4.2 |  | 4.7 | 1.9 | 5.5 | filamin B, beta (actin binding protein 278) [Homo sapiens] |
| gi|70166944|ref|NP_05 | 2.8 |  | 2.8 | 2.6 | 5.3 | adenosine deaminase, RNA-specific isoform b [Homo sapiens] |
| gi|4505939|ref|NP_000 | 2 |  | 2 | 3.5 | 4.4 | DNA directed RNA polymerase II polypeptide A [Homo sapiens] |
| gi|16753233|ref|NP_00 | 1.9 |  | 1.9 | 1.2 | 3.1 | talin 1 [Homo sapiens] |
| gi|4758012|ref|NP_004 | 2.1 |  | 2.1 | 1.7 | 3.1 | clathrin heavy chain 1 [Homo sapiens] |
| gi|110349715|ref|NP_0 | 0.1 |  | 0.1 | 0.2 | 0.3 | titin isoform N2-B [Homo sapiens] |

FIG. 16

| Locus | Normal Wild Type 200mM | Normal Mutant 200mM | Loose' Wild Type 200mM | Loose' Mutant 200mM | Total | Description |
|---|---|---|---|---|---|---|
| gi|4506725|ref|NP_000 |  |  | 3.4 | 3.4 | 3.4 | ribosomal protein S4, X-linked X isoform [Homo sapiens] |
| gi|50659095|ref|NP_00 |  |  | 3.7 | 3.7 | 6 | DEAD (Asp-Glu-Ala-Asp) box polypeptide 21 [Homo sapiens] |

FIG. 17

| Locus | Normal Wild Type 200mM | Normal Mutant 200mM | Loose' Wild Type 200mM | Loose' Mutant 200mM | Total | Description |
|---|---|---|---|---|---|---|
| gi|114155148|ref|NP_0 |  | 51.4 |  | 51.4 | 51.4 | tropomyosin 3 isoform 5 [Homo sapiens] |
| gi|169211725|ref|XP_9 |  | 44.3 |  | 44.3 | 44.3 | PREDICTED: similar to 40S ribosomal protein S28 [Homo sapiens] |
| gi|17158044|ref|NP_00 |  | 29.3 |  | 29.3 | 29.3 | ribosomal protein S6 [Homo sapiens] |
| gi|4506901|ref|NP_003 |  | 28.7 |  | 28.7 | 28.7 | splicing factor, arginine/serine-rich 3 [Homo sapiens] |
| gi|4506621|ref|NP_000 |  | 27.6 |  | 27.6 | 27.6 | ribosomal protein L26 [Homo sapiens] |
| gi|4506713|ref|NP_002 |  | 26.9 |  | 26.9 | 26.9 | ubiquitin and ribosomal protein S27a precursor [Homo sapiens] |
| gi|34098946|ref|NP_00 |  | 25 |  | 25 | 25 | nuclease sensitive element binding protein 1 [Homo sapiens] |
| gi|16117796|ref|NP_37 |  | 24.8 |  | 24.8 | 24.8 | ribosomal protein L36 [Homo sapiens] |
| gi|4506693|ref|NP_001 |  | 23 |  | 23 | 23 | ribosomal protein S17 [Homo sapiens] |
| gi|14591909|ref|NP_00 |  | 20.9 |  | 21.2 | 21.2 | ribosomal protein L5 [Homo sapiens] |
| gi|4758950|ref|NP_000 |  | 19.9 |  | 20.8 | 20.8 | peptidylprolyl isomerase B precursor [Homo sapiens] |
| gi|3336163|ref|NP_00 |  | 20.1 |  | 20.1 | 20.1 | eukaryotic translation initiation factor 1A, Y chromosome [Homo sapiens] |
| gi|4506695|ref|NP_001 |  | 15.2 |  | 20 | 20 | ribosomal protein S19 [Homo sapiens] |
| gi|4506685|ref|NP_001 |  | 19.9 |  | 19.9 | 19.9 | ribosomal protein S13 [Homo sapiens] |
| gi|4506613|ref|NP_001 |  | 19.5 |  | 19.5 | 19.5 | ribosomal protein L22 proprotein [Homo sapiens] |
| gi|15811782|ref|NP_05 |  | 19.3 |  | 19.3 | 19.3 | G patch domain and KOW motifs [Homo sapiens] |
| gi|4506669|ref|NP_001 |  | 19.3 |  | 19.3 | 19.3 | ribosomal protein S20 [Homo sapiens] |
| gi|7657176|ref|NP_055 |  | 17.6 |  | 17.6 | 17.6 | canopy 2 homolog [Homo sapiens] |
| gi|4507129|ref|NP_003 |  | 17.4 |  | 17.4 | 17.4 | small nuclear ribonucleoprotein polypeptide E [Homo sapiens] |
| gi|169184561|ref|XP_0 |  | 17.2 |  | 17.2 | 17.2 | PREDICTED: similar to v-fos transformation effector protein isoform 1 [Homo sapiens] |
| gi|4505119|ref|NP_003 |  | 10 |  | 16.8 | 16.8 | methyl-CpG binding domain protein 3 [Homo sapiens] |
| gi|4506623|ref|NP_000 |  | 16.2 |  | 16.2 | 16.2 | ribosomal protein L27 [Homo sapiens] |
| gi|4507651|ref|NP_003 |  | 16.1 |  | 16.1 | 16.1 | tropomyosin 4 [Homo sapiens] |
| gi|169165866|ref|XP_0 |  | 15.8 |  | 15.8 | 15.8 | PREDICTED: similar to ribosomal protein L10a [Homo sapiens] |
| gi|4506691|ref|NP_001 |  | 15.8 |  | 15.8 | 15.8 | ribosomal protein S16 [Homo sapiens] |
| gi|21328448|ref|NP_64 |  | 15.4 |  | 15.4 | 15.4 | tyrosine 3-monooxygenase/tryptophan 5-monooxygenase activation protein, beta polypeptide [Homo sapiens] |
| gi|4502747|ref|NP_001 |  | 14.2 |  | 14.2 | 14.2 | cyclin-dependent kinase 9 [Homo sapiens] |
| gi|38455427|ref|NP_00 |  | 14.1 |  | 14.1 | 14.1 | chaperonin containing TCP1, subunit 4 (delta) [Homo sapiens] |
| gi|51149463|ref|NP_14 |  | 14 |  | 14 | 14 | caldesmon 1 isoform 4 [Homo sapiens] |
| gi|4506669|ref|NP_000 |  | 14 |  | 14 | 14 | ribosomal protein P1 isoform 1 [Homo sapiens] |
| gi|28558998|ref|NP_78 |  | 13.7 |  | 13.7 | 13.7 | polypyrimidine tract-binding protein d isoform d [Homo sapiens] |
| gi|55743159|ref|NP_00 |  | 13.2 |  | 13.2 | 13.2 | WD repeat domain 33 isoform 3 [Homo sapiens] |
| gi|113416101|ref|XP_0 |  | 12.8 |  | 12.8 | 12.8 | PREDICTED: similar to 40S ribosomal protein S12 [Homo sapiens] |
| gi|4502709|ref|NP_001 |  | 12.5 |  | 12.5 | 12.5 | cell division cycle 2 protein isoform 1 [Homo sapiens] |
| gi|15431288|ref|NP_00 |  | 12.4 |  | 12.4 | 12.4 | ribosomal protein L10a [Homo sapiens] |
| gi|42476296|ref|NP_00 |  | 12 |  | 12 | 12 | tropomyosin 2 (beta) isoform 1 [Homo sapiens] |
| gi|148839362|ref|NP_6 |  | 7 |  | 11.9 | 11.9 | LSM14 homolog B [Homo sapiens] |
| gi|88942898|ref|XP_93 |  | 11.8 |  | 11.8 | 11.8 | PREDICTED: similar to beta-actin [Homo sapiens] |
| gi|51477708|ref|NP_00 |  | 11.5 |  | 11.5 | 11.5 | heterogeneous nuclear ribonucleoprotein D isoform d [Homo sapiens] |
| gi|153791431|ref|NP_0 |  | 11.4 |  | 11.4 | 11.4 | processing of precursor 7, ribonuclease P/MRP subunit [Homo sapiens] |
| gi|13259531|ref|NP_07 |  | 11.2 |  | 11.2 | 11.2 | survival of motor neuron 2, centromeric isoform c [Homo sapiens] |
| gi|169215435|ref|NP_0 |  | 11.2 |  | 11.2 | 11.2 | PREDICTED: similar to peptidylprolyl isomerase A-like [Homo sapiens] |
| gi|24308005|ref|NP_05 |  | 6.2 |  | 10.8 | 10.8 | Paf1/RNA polymerase II complex component [Homo sapiens] |
| gi|4758356|ref|NP_004 |  | 10.8 |  | 10.8 | 10.8 | flap structure-specific endonuclease 1 [Homo sapiens] |
| gi|5453565|ref|NP_006 |  | 10.8 |  | 10.8 | 10.8 | BAH-associated protein 2 isoform 3 [Homo sapiens] |
| gi|110347425|ref|NP_0 |  | 9.1 |  | 10.6 | 10.6 | structural maintenance of chromosomes 2-like 1 [Homo sapiens] |
| gi|4759160|ref|NP_004 |  | 10.3 |  | 10.3 | 10.3 | small nuclear ribonucleoprotein polypeptide D3 [Homo sapiens] |
| gi|20127486|ref|NP_00 |  | 10.1 |  | 10.1 | 10.1 | mannose 6 phosphate receptor binding protein 1 [Homo sapiens] |
| gi|40805864|ref|NP_95 |  | 10 |  | 10 | 10 | tumor protein D52-like 2 isoform a [Homo sapiens] |
| gi|4557701|ref|NP_000 |  | 10 |  | 10 | 10 | keratin 17 [Homo sapiens]; keratin 17 [Homo sapiens] |

FIG. 17 (Cont.)

| ID | | Val1 | | Val2 | Val3 | Description |
|---|---|---|---|---|---|---|
| gi|4506243|ref|NP_002 | | 9.9 | | 9.9 | 9.9 | polypyrimidine tract-binding protein 1 isoform a [Homo sapiens] |
| gi|21361809|ref|NP_06 | | 9.7 | | 9.7 | 9.7 | kynurenine aminotransferase III isoform 3 [Homo sapiens] |
| gi|45643135|ref|NP_99 | | 9.4 | | 9.4 | 9.4 | MORF-related gene 15 isoform 2 [Homo sapiens] |
| gi|24308207|ref|NP_06 | | 9.3 | | 9.3 | 9.3 | leucine rich repeat containing 47 [Homo sapiens] |
| gi|40354195|ref|NP_95 | | 9.3 | | 9.3 | 9.3 | keratin 18 [Homo sapiens] keratin 18; cytokeratin 18 [Homo sapiens] |
| gi|4826734|ref|NP_004 | | 9.3 | | 9.3 | 9.3 | fusion (involved in t(12;16) in malignant liposarcoma) [Homo sapiens] |
| gi|4506609|ref|NP_000 | | 9.2 | | 9.2 | 9.2 | ribosomal protein L19 [Homo sapiens] |
| gi|32698730|ref|NP_06 | | 7.6 | | 9.1 | 9.1 | nuclear fragile X mental retardation protein interacting protein 2 [Homo sapiens] |
| gi|9994185|ref|NP_057 | | 9 | | 9 | 9 | RNA binding motif protein 7 [Homo sapiens] |
| gi|5803111|ref|NP_006 | | 8.5 | | 8.5 | 8.5 | EBNA1 binding protein 2 [Homo sapiens] |
| gi|52632383|ref|NP_00 | | 8.3 | | 8.3 | 8.3 | heterogeneous nuclear ribonucleoprotein L isoform a [Homo sapiens] |
| gi|55956788|ref|NP_00 | | 8.2 | | 8.2 | 8.2 | nucleolin [Homo sapiens] |
| gi|4503841|ref|NP_001 | | 8 | | 8 | 8 | ATP-dependent DNA helicase II, 70 kDa subunit [Homo sapiens] |
| gi|16945970|ref|NP_06 | | 7.8 | | 7.8 | 7.8 | PC4 and SFRS1 interacting protein 1 isoform 1 [Homo sapiens] |
| gi|53759148|ref|NP_00 | | 7.8 | | 7.8 | 7.8 | retinoblastoma binding protein 5 [Homo sapiens] |
| gi|32626688|ref|NP_0 | | 6.4 | | 7.7 | 7.7 | mediator of DNA damage checkpoint 1 [Homo sapiens] |
| gi|21361322|ref|NP_06 | | 7.7 | | 7.7 | 7.7 | tubulin, beta 4 [Homo sapiens] |
| gi|30795193|ref|NP_84 | | 7.7 | | 7.7 | 7.7 | septin 10 isoform 2 [Homo sapiens] |
| gi|78000213|ref|NP_00 | | 7.7 | | 7.7 | 7.7 | DNA methyltransferase 1 associated protein 1 [Homo sapiens] |
| gi|6912246|ref|NP_036 | | 7.5 | | 7.5 | 7.5 | CD3E antigen, epsilon polypeptide associated protein [Homo sapiens] |
| gi|5032087|ref|NP_005 | | 7.4 | | 7.4 | 7.4 | splicing factor 3a, subunit 1, 120kDa isoform 1 [Homo sapiens] |
| gi|51479192|ref|NP_00 | | 7.4 | | 7.4 | 7.4 | ring finger protein 1 [Homo sapiens] |
| gi|20070125|ref|NP_00 | | 7.3 | | 7.3 | 7.3 | prolyl 4-hydroxylase, beta subunit precursor [Homo sapiens] |
| gi|7661892|ref|NP_055 | | 7.3 | | 7.3 | 7.3 | REST corepressor 1 [Homo sapiens] |
| gi|19387846|ref|NP_05 | | 7.1 | | 7.1 | 7.1 | melanoma antigen family D, 2 [Homo sapiens] |
| gi|20149594|ref|NP_03 | | 6.9 | | 6.9 | 6.9 | heat shock 90kDa protein 1, beta [Homo sapiens] |
| gi|54873624|ref|NP_11 | | 6.8 | | 6.8 | 6.8 | eukaryotic translation initiation factor 2A [Homo sapiens] |
| gi|11673470|ref|NP_0 | | 6.7 | | 6.7 | 6.7 | interferon regulatory factor 2 binding protein 2 isoform B [Homo sapiens] |
| gi|14210536|ref|NP_11 | | 6.7 | | 6.7 | 6.7 | tubulin, beta 6 [Homo sapiens] |
| gi|27262651|ref|NP_68 | | 4.1 | | 6.5 | 6.5 | ataxin 2 related protein isoform D [Homo sapiens] |
| gi|12789562|ref|NP_0 | | 4.7 | | 6.4 | 6.4 | interferon, gamma-inducible protein 16 [Homo sapiens] |
| gi|15431310|ref|NP_00 | | 6.4 | | 6.4 | 6.4 | keratin 14 [Homo sapiens] keratin 14; cytokeratin 14 [Homo sapiens] |
| gi|4758304|ref|NP_004 | | 6.4 | | 6.4 | 6.4 | protein disulfide isomerase-associated 4 [Homo sapiens] |
| gi|4758958|ref|NP_004 | | 6.4 | | 6.4 | 6.4 | cAMP-dependent protein kinase, regulatory subunit alpha 2 [Homo sapiens] |
| gi|7657387|ref|NP_055 | | 5.3 | | 6.4 | 6.4 | CCR4-NOT transcription complex, subunit 3 [Homo sapiens] |
| gi|40548332|ref|NP_95 | | 6.2 | | 6.2 | 6.2 | coiled-coil domain containing 137 [Homo sapiens] |
| gi|5031753|ref|NP_005 | | 6.2 | | 6.2 | 6.2 | heterogeneous nuclear ribonucleoprotein H1 [Homo sapiens] |
| gi|24307879|ref|NP_00 | | 6 | | 6 | 6 | dynein, cytoplasmic 1, intermediate chain 2 [Homo sapiens] |
| gi|5031839|ref|NP_005 | | 5.9 | | 5.9 | 5.9 | keratin 6A [Homo sapiens] keratin 6A; keratin, epidermal type II, K6A; cytokeratin 6A; 56 cytoskeletal type II keratin [Homo sapiens] |
| gi|110431354|ref|NP_0 | | 5.8 | | 5.8 | 5.8 | transducer of regulated CREB protein 3 isoform a [Homo sapiens] |
| gi|34101288|ref|NP_05 | | 5.8 | | 5.8 | 5.8 | cleavage and polyadenylation specific factor 2 [Homo sapiens] |
| gi|73623035|ref|NP_00 | | 5.8 | | 5.8 | 5.8 | sperm associated antigen 5 [Homo sapiens] |
| gi|11863154|ref|NP_00 | | 5.7 | | 5.7 | 5.7 | archain [Homo sapiens] |
| gi|14249678|ref|NP_11 | | 5.7 | | 5.7 | 5.7 | RNA binding motif protein 17 [Homo sapiens] |
| gi|44921615|ref|NP_78 | | 3.7 | | 5.7 | 5.7 | exocyst complex 84-kDa subunit [Homo sapiens] |
| gi|5174751|ref|NP_006 | | 5.7 | | 5.7 | 5.7 | Yes-associated protein 1, 65 kD [Homo sapiens] |
| gi|41281612|ref|NP_11 | | 5.5 | | 5.5 | 5.5 | hypothetical protein LOC283489 [Homo sapiens] |
| gi|7657015|ref|NP_055 | | 5.5 | | 5.5 | 5.5 | hypothetical protein LOC51493 [Homo sapiens] |
| gi|19923142|ref|NP_00 | | 5.4 | | 5.4 | 5.4 | karyopherin beta 1 [Homo sapiens] |
| gi|44955929|ref|NP_98 | | 5.4 | | 5.4 | 5.4 | calmodulin regulated spectrin-associated protein 1-like 1 [Homo sapiens] |
| gi|7669492|ref|NP_002 | | 5.4 | | 5.4 | 5.4 | glyceraldehyde-3-phosphate dehydrogenase [Homo sapiens] |
| gi|19913406|ref|NP_00 | | 5.3 | | 5.3 | 5.3 | DNA topoisomerase II, alpha isozyme [Homo sapiens] |
| gi|23308577|ref|NP_00 | | 5.3 | | 5.3 | 5.3 | phosphoglycerate dehydrogenase [Homo sapiens] |
| gi|11225260|ref|NP_00 | | 5.2 | | 5.2 | 5.2 | DNA topoisomerase I [Homo sapiens] |
| gi|86990441|ref|NP_05 | | 5.2 | | 5.2 | 5.2 | MAP/microtubule affinity-regulating kinase 2 isoform a [Homo sapiens] |
| gi|8922886|ref|NP_060 | | 5.2 | | 5.2 | 5.2 | DDX19-like protein [Homo sapiens] |
| gi|116875767|ref|NP_0 | | 5.1 | | 5.1 | 5.1 | tight junction protein 1 isoform a [Homo sapiens] |
| gi|126723060|ref|NP_0 | | 4.2 | | 5.1 | 5.1 | zinc finger CCCH-type containing 4 [Homo sapiens] |
| gi|38202257|ref|NP_93 | | 2.5 | | 5.1 | 5.1 | alpha glucosidase II alpha subunit isoform 2 [Homo sapiens] |
| gi|41281437|ref|NP_05 | | 5.1 | | 5.1 | 5.1 | nucleoporin 93kDa [Homo sapiens] |
| gi|13375809|ref|NP_07 | | 4.8 | | 4.8 | 4.8 | RNA polymerase II associated protein 3 [Homo sapiens] |
| gi|21361144|ref|NP_00 | | 4.8 | | 4.8 | 4.8 | proteasome 26S ATPase subunit 3 [Homo sapiens] |
| gi|4759258|ref|NP_004 | | 4.8 | | 4.8 | 4.8 | Ac-like transposable element [Homo sapiens] |
| gi|31652236|ref|NP_00 | | 4.7 | | 4.7 | 4.7 | cut-like homeobox 1 isoform b [Homo sapiens] |
| gi|169171969|ref|XP_0 | | 4.5 | | 4.5 | 4.5 | PREDICTED: similar to hCG2014184 [Homo sapiens] |
| gi|48854099|ref|NP_005 | | 4.5 | | 4.5 | 4.5 | high density lipoprotein binding protein [Homo sapiens] |
| gi|49158690|ref|NP_5 | | 4.4 | | 4.4 | 4.4 | HLA-B associated transcript-2 [Homo sapiens] |
| gi|4505917|ref|NP_002 | | 2.8 | | 4.4 | 4.4 | exosome component 10 isoform 2 [Homo sapiens] |
| gi|12056468|ref|NP_06 | | 4.3 | | 4.3 | 4.3 | junction plakoglobin [Homo sapiens] |
| gi|29568103|ref|NP_05 | | 4.3 | | 4.3 | 4.3 | U1 small nuclear ribonucleoprotein 70 kDa [Homo sapiens] |
| gi|4507507|ref|NP_003 | | 4.3 | | 4.3 | 4.3 | timeless homolog [Homo sapiens] |
| gi|7549809|ref|NP_005 | | 4.3 | | 4.3 | 4.3 | plastin 3 [Homo sapiens] |
| gi|55749531|ref|NP_00 | | 4.2 | | 4.2 | 4.2 | splicing factor 3B subunit 2 [Homo sapiens] |
| gi|13786127|ref|NP_03 | | 3.9 | | 3.9 | 3.9 | Cdc42 effector protein 4 [Homo sapiens] |
| gi|59814411|ref|NP_05 | | 2.4 | | 3.9 | 3.9 | hypothetical protein LOC253725 [Homo sapiens] |
| gi|148612835|ref|NP_0 | | 2.8 | | 3.8 | 3.8 | zinc finger protein 207 isoform c [Homo sapiens] |
| gi|157671927|ref|NP_6 | | 3.8 | | 3.8 | 3.8 | spermatogenesis associated 5 [Homo sapiens] |
| gi|169216615|ref|XP_0 | | 3.8 | | 3.8 | 3.8 | PREDICTED: similar to translation elongation factor 1 alpha 1-like 14 [Homo sapiens] |
| gi|21626468|ref|NP_05 | | 3.1 | | 3.8 | 3.8 | zinc finger protein 638 [Homo sapiens] |
| gi|5031923|ref|NP_005 | | 3.8 | | 3.8 | 3.8 | meiotic recombination 11 homolog A isoform 1 [Homo sapiens] |
| gi|5032031|ref|NP_005 | | 3.8 | | 3.8 | 3.8 | RNA binding motif protein 5 [Homo sapiens] |
| gi|66348045|ref|NP_05 | | 3.8 | | 3.8 | 3.8 | zinc finger, C3HC type 1 [Homo sapiens] |
| gi|118498359|ref|NP_0 | | 3.7 | | 3.7 | 3.7 | ribosomal L1 domain containing 1 [Homo sapiens] |

FIG. 17 (Cont.)

| Locus | | | | Description |
|---|---|---|---|---|
| gi|40353738|ref|NP_44 | 3.7 | 3.7 | 3.7 | c-Mpl binding protein isoform a [Homo sapiens] |
| gi|54112317|ref|NP_03 | 3.7 | 3.7 | 3.7 | splicing factor 3b, subunit 1 isoform 1 [Homo sapiens] |
| gi|118601081|ref|NP_0 | 3.5 | 3.5 | 3.5 | heterogeneous nuclear ribonucleoprotein U-like 2 [Homo sapiens] |
| gi|18378731|ref|NP_06 | 3.5 | 3.5 | 3.5 | HMG-BOX transcription factor BBX [Homo sapiens] |
| gi|31543535|ref|NP_05 | 3.5 | 3.5 | 3.5 | R3H domain containing 1 [Homo sapiens] |
| gi|59086624|ref|NP_29 | 3.4 | 3.5 | 3.5 | integrator complex subunit 4 [Homo sapiens] |
| gi|124494238|ref|NP_0 | 3.4 | 3.4 | 3.4 | myosin IC isoform a [Homo sapiens] |
| gi|13690868|ref|NP_00 | 3.4 | 3.4 | 3.4 | methylenetetrahydrofolate dehydrogenase 1 [Homo sapiens] |
| gi|154813201|ref|NP_0 | 3.4 | 3.4 | 3.4 | cartilage paired-class homeoprotein 1 [Homo sapiens] |
| gi|24234753|ref|NP_00 | 3.4 | 3.4 | 3.4 | interleukin enhancer binding factor 3 isoform b [Homo sapiens] |
| gi|119703744|ref|NP_0 | 3.3 | 3.3 | 3.3 | desmoglein 1 preproprotein [Homo sapiens] |
| gi|47519639|ref|NP_00 | 3.3 | 3.3 | 3.3 | microtubule-associated protein 4 isoform 1 [Homo sapiens] |
| gi|148536855|ref|NP_0 | 3.2 | 3.2 | 3.2 | coatomer protein complex, subunit alpha isoform 1 [Homo sapiens] |
| gi|32528306|ref|NP_00 | 3.2 | 3.2 | 3.2 | replication factor C large subunit [Homo sapiens] |
| gi|41327771|ref|NP_00 | 3.2 | 3.2 | 3.2 | DEAD (Asp-Glu-Ala-Asp) box polypeptide 23 [Homo sapiens] |
| gi|4557365|ref|NP_000 | 3.2 | 3.2 | 3.2 | Bloom syndrome protein [Homo sapiens] |
| gi|84043963|ref|NP_05 | 3.1 | 3.1 | 3.1 | eukaryotic translation initiation factor 5B [Homo sapiens] |
| gi|147903302|ref|NP_0 | 3 | 3 | 3 | MAP7 domain containing 3 [Homo sapiens] |
| gi|154448888|ref|NP_0 | 3 | 3 | 3 | RNA binding motif protein 33 isoform 1 [Homo sapiens] |
| gi|4503509|ref|NP_003 | 3 | 3 | 3 | eukaryotic translation initiation factor 3, subunit 10 theta, 150/170kDa [Homo sapiens] |
| gi|20587019|ref|NP_0 | 2.9 | 2.9 | 2.9 | zinc finger protein 318 [Homo sapiens] |
| gi|147904340|ref|NP_0 | 2.9 | 2.9 | 2.9 | WD repeat domain 82 [Homo sapiens] |
| gi|55770844|ref|NP_00 | 2.9 | 2.9 | 2.9 | catenin, alpha 1 [Homo sapiens] |
| gi|7669490|ref|NP_053 | 2.9 | 2.9 | 2.9 | Ewing sarcoma breakpoint region 1 isoform EWS-b [Homo sapiens] |
| gi|157739942|ref|NP_0 | 2.8 | 2.8 | 2.8 | gemin 5 [Homo sapiens] |
| gi|4503351|ref|NP_001 | 1.8 | 2.8 | 2.8 | DNA (cytosine-5-)-methyltransferase 1 [Homo sapiens] |
| gi|71725360|ref|NP_05 | 2.8 | 2.8 | 2.8 | zinc finger protein 609 [Homo sapiens] |
| gi|153792074|ref|NP_0 | 2.7 | 2.7 | 2.7 | proline rich 12 [Homo sapiens] |
| gi|16306568|ref|NP_07 | 2.7 | 2.7 | 2.7 | poly(A) polymerase gamma [Homo sapiens] |
| gi|18375673|ref|NP_00 | 2.7 | 2.7 | 2.7 | regulator of nonsense transcripts 1 [Homo sapiens] |
| gi|50010552|ref|NP_0 | 2.6 | 2.6 | 2.6 | FK506 binding protein 15, 133kDa [Homo sapiens] |
| gi|169218238|ref|XP_0 | 1.8 | 2.6 | 2.6 | PREDICTED: hypothetical protein, partial [Homo sapiens] |
| gi|145309300|ref|NP_1 | 2.5 | 2.5 | 2.5 | cell division cycle 2-like 5 isoform 2 [Homo sapiens] |
| gi|32698688|ref|NP_00 | 2.5 | 2.5 | 2.5 | citron [Homo sapiens] |
| gi|32698936|ref|NP_87 | 2.5 | 2.5 | 2.5 | B-cell CLL/lymphoma 9-like [Homo sapiens] |
| gi|21237802|ref|NP_00 | 2.4 | 2.4 | 2.4 | SWI/SNF-related matrix-associated actin-dependent regulator of chromatin c1 [Homo sapiens] |
| gi|4507243|ref|NP_003 | 2.4 | 2.4 | 2.4 | structure specific recognition protein 1 [Homo sapiens] |
| gi|157739945|ref|NP_0 | 1.5 | 2.1 | 2.1 | tetratricopeptide repeat, ankyrin repeat and coiled-coil containing 2 [Homo sapiens] |
| gi|14790190|ref|NP_05 | 1 | 2 | 2 | spen homolog, transcriptional regulator [Homo sapiens] |
| gi|56550039|ref|NP_00 | 1.6 | 2 | 2 | myeloid/lymphoid or mixed-lineage leukemia (trithorax homolog, Drosophila) [Homo sapiens] |
| gi|169169783|ref|XP_0 | 1.9 | 1.9 | 1.9 | PREDICTED: similar to hCG18281 [Homo sapiens] |
| gi|25121987|ref|NP_05 | 1.9 | 1.9 | 1.9 | non-SMC condensin I complex, subunit H [Homo sapiens] |
| gi|62241042|ref|NP_00 | 1.9 | 1.9 | 1.9 | glutaminyl-prolyl tRNA synthetase [Homo sapiens] |
| gi|19913408|ref|NP_00 | 1.7 | 1.7 | 1.7 | DNA topoisomerase II, beta isozyme [Homo sapiens] |
| gi|17190342|ref|NP_0 | 1.6 | 1.6 | 1.6 | PHD finger protein 2 [Homo sapiens] |
| gi|50959191|ref|NP_00 | 1.6 | 1.6 | 1.6 | rho guanine nucleotide exchange factor 5 [Homo sapiens] |
| gi|53759122|ref|NP_00 | 1.6 | 1.6 | 1.6 | adenomatous polyposis coli [Homo sapiens] |
| gi|50170649|ref|NP_00 | 1.5 | 1.5 | 1.5 | kinesin family member 26A [Homo sapiens] |
| gi|33620769|ref|NP_00 | 1.5 | 1.5 | 1.5 | retinoblastoma-binding protein 6 isoform 1 [Homo sapiens] |
| gi|71044479|ref|NP_14 | 1.5 | 1.5 | 1.5 | death inducer-obliterator 1 isoform c [Homo sapiens] |
| gi|51226124|ref|NP_05 | 1.4 | 1.4 | 1.4 | GTPase activating Rap/RanGAP domain-like 1 isoform 1 [Homo sapiens] |
| gi|4826730|ref|NP_004 | 1.3 | 1.3 | 1.3 | FK506 binding protein 12-rapamycin associated protein 1 [Homo sapiens] |
| gi|146219843|ref|NP_0 | 1.1 | 1.1 | 1.1 | Snf2-related CBP activator protein [Homo sapiens] |
| gi|38788260|ref|NP_00 | 1.1 | 1.1 | 1.1 | bromodomain PHD finger transcription factor isoform 2 [Homo sapiens] |
| gi|33350932|ref|NP_00 | 0.7 | 0.7 | 0.7 | dynein, cytoplasmic, heavy polypeptide 1 [Homo sapiens] |
| gi|91208426|ref|NP_00 | 0.7 | 0.7 | 0.7 | U5 snRNP-specific protein [Homo sapiens] |
| gi|33188443|ref|NP_14 | 0.5 | 0.5 | 0.5 | microfilament and actin filament cross-linker protein isoform b [Homo sapiens] |

FIG. 18

| | Normal | | Loose | | | |
|---|---|---|---|---|---|---|
| Locus | Wild Type 200mM | Mutant 200mM | Wild Type 200mM | Mutant 200mM | Total | Description |
| gi|4506631|ref|NP_000 | 24.3 | | 24.3 | | 24.3 | ribosomal protein L30 [Homo sapiens] |
| gi|14999961|ref|NP_0 | 22.8 | | 22.8 | | 22.8 | signal recognition particle 14kDa (homologous Alu RNA binding protein) [Homo sapiens] |
| gi|46094070|ref|NP_07 | 22.8 | | 22.8 | | 22.8 | hypothetical protein LOC80097 [Homo sapiens] |
| gi|5454106|ref|NP_006 | 20.6 | | 20.6 | | 20.6 | TBP-related factor 10 [Homo sapiens] |
| gi|27734727|ref|NP_77 | 19.7 | | 19.7 | | 19.7 | coiled-coil domain containing 95 [Homo sapiens] |
| gi|4506629|ref|NP_000 | 17.9 | | 17 | | 17 | ribosomal protein L29 [Homo sapiens] |
| gi|113430469|ref|XP_9 | 15 | | 15 | | 15 | PREDICTED: similar to ribosomal protein S23 [Homo sapiens] |
| gi|4506605|ref|NP_000 | 14.3 | | 14.3 | | 14.3 | ribosomal protein L23 [Homo sapiens] |
| gi|5803013|ref|NP_006 | 14.2 | | 14.2 | | 14.2 | endoplasmic reticulum protein 29 isoform 1 precursor [Homo sapiens] |
| gi|30795231|ref|NP_00 | 12.8 | | 12.8 | | 12.8 | brain abundant, membrane attached signal protein 1 [Homo sapiens] |
| gi|1644542|ref|NP_44 | 10.6 | | 10.6 | | 10.6 | secretory carrier membrane protein 3 isoform 2 [Homo sapiens] |
| gi|5729939|ref|NP_006 | 10 | | 10 | | 10 | cleavage and polyadenylation specific factor 4, 30kDa isoform 1 [Homo sapiens] |
| gi|31542947|ref|NP_00 | 9.4 | | 9.4 | | 9.4 | chaperonin [Homo sapiens] |
| gi|38372925|ref|NP_94 | 9.3 | | 9.3 | | 9.3 | basigin isoform 2 [Homo sapiens] |
| gi|17190192|ref|NP_0 | 9.2 | | 9.2 | | 9.2 | heterogeneous nuclear ribonucleoprotein C isoform a [Homo sapiens] |

FIG. 18 (Cont.)

| Locus | | | | | Description |
|---|---|---|---|---|---|
| gi\|46807450\|ref\|NP_95 | 8.9 | | 8.9 | 8.9 | papillary renal cell carcinoma translocation-associated gene product isoform 2 [Homo sapiens] |
| gi\|42544172\|ref\|NP_97 | 8.8 | | 8.8 | 8.8 | E74-like factor 2 (ets domain transcription factor) isoform 1 [Homo sapiens] |
| gi\|100816392\|ref\|NP_0 | 8.7 | | 8.7 | 8.7 | far upstream element (FUSE) binding protein 3 [Homo sapiens] |
| gi\|75052234\|ref\|NP_06 | 8.6 | | 8.6 | 8.6 | nucleolar and spindle associated protein 1 isoform 2 [Homo sapiens] |
| gi\|15055539\|ref\|NP_00 | 8.5 | | 8.5 | 8.5 | ribosomal protein S2 [Homo sapiens] |
| gi\|20127556\|ref\|NP_05 | 6.7 | | 8.2 | 8.2 | G-2 and S-phase expressed 1 [Homo sapiens] |
| gi\|169203958\|ref\|XP_0 | 7.5 | | 7.5 | 7.5 | PREDICTED: hypothetical protein [Homo sapiens] |
| gi\|8837290\|ref\|NP_61 | 7.5 | | 7.5 | 7.5 | Sp1 transcription factor [Homo sapiens] |
| gi\|31742536\|ref\|NP_07 | 4.9 | | 7.3 | 7.3 | fidgetin-like 1 [Homo sapiens] |
| gi\|5730023\|ref\|NP_006 | 7.3 | | 7.3 | 7.3 | RuvB-like 2 [Homo sapiens] |
| gi\|33356652\|ref\|NP_05 | 6.7 | | 6.7 | 6.7 | G patch domain containing 4 isoform 1 [Homo sapiens] |
| gi\|8923040\|ref\|NP_060 | 6.7 | | 6.7 | 6.7 | CDKN2A interacting protein [Homo sapiens] |
| gi\|40254861\|ref\|NP_05 | 4.1 | | 6.5 | 6.5 | ubiquitin associated protein 2-like [Homo sapiens] |
| gi\|20127499\|ref\|NP_00 | 6.4 | | 6.4 | 6.4 | arginine/serine-rich splicing factor 6 [Homo sapiens] |
| gi\|30795212\|ref\|NP_00 | 6.2 | | 6.2 | 6.2 | insulin-like growth factor 2 mRNA binding protein 3 [Homo sapiens] |
| gi\|7657307\|ref\|NP_055 | 5.5 | | 5.5 | 5.5 | LIM domains containing 1 [Homo sapiens] |
| gi\|62865614\|ref\|NP_00 | 5.3 | | 5.3 | 5.3 | TAF9 RNA polymerase II isoform a [Homo sapiens] |
| gi\|10863899\|ref\|NP_00 | 4.8 | | 4.8 | 4.8 | numb homolog (Drosophila)-like [Homo sapiens] |
| gi\|63003907\|ref\|NP_00 | 4.5 | | 4.5 | 4.5 | protein phosphatase 1, regulatory (inhibitor) subunit 13 like [Homo sapiens] |
| gi\|48762682\|ref\|NP_00 | 4.3 | | 4.3 | 4.3 | Na+/K+ -ATPase alpha 1 subunit isoform b preprotein [Homo sapiens] |
| gi\|9257207\|ref\|NP_057 | 4.3 | | 4.3 | 4.3 | folate receptor 1 precursor [Homo sapiens] |
| gi\|156105703\|ref\|NP_0 | 4.1 | | 4.1 | 4.1 | SUMO1/sentrin specific peptidase 6 isoform 2 [Homo sapiens] |
| gi\|33620735\|ref\|NP_06 | 4.1 | | 4.1 | 4.1 | YEATS domain containing 2 [Homo sapiens] |
| gi\|40548408\|ref\|NP_95 | 4.1 | | 4.1 | 4.1 | p30 DBC protein [Homo sapiens] |
| gi\|5730037\|ref\|NP_006 | 4 | | 4 | 4 | SEC10 protein [Homo sapiens] |
| gi\|54144625\|ref\|NP_00 | 3.8 | | 3.8 | 3.8 | numb homolog isoform 1 [Homo sapiens] |
| gi\|50345873\|ref\|NP_06 | 3.7 | | 3.7 | 3.7 | zinc finger protein 295 [Homo sapiens] |
| gi\|5453607\|ref\|NP_006 | 3.7 | | 3.7 | 3.7 | chaperonin containing TCP1, subunit 7 isoform a [Homo sapiens] |
| gi\|31563537\|ref\|NP_05 | 1.9 | | 3.6 | 3.6 | CUP-associating protein 1 [Homo sapiens] |
| gi\|40068047\|ref\|NP_95 | 3.5 | | 3.5 | 3.5 | cyclin M3 isoform 2 [Homo sapiens] |
| gi\|4557495\|ref\|NP_001 | 3.5 | | 3.5 | 3.5 | cleavage stimulation factor subunit 3 isoform 1 [Homo sapiens] |
| gi\|48613886\|ref\|NP_0 | 3.4 | | 3.4 | 3.4 | regulatory factor X domain containing 2 [Homo sapiens] |
| gi\|55956916\|ref\|NP_00 | 2.2 | | 3.4 | 3.4 | myosin IE [Homo sapiens] |
| gi\|21071052\|ref\|NP_00 | 3.3 | | 3.3 | 3.3 | helicase-like transcription factor [Homo sapiens] |
| gi\|4503483\|ref\|NP_001 | 3.3 | | 3.3 | 3.3 | eukaryotic translation elongation factor 2 [Homo sapiens] |
| gi\|6453818\|ref\|NP_015 | 3.3 | | 3.3 | 3.3 | kinesin family member 22 [Homo sapiens] |
| gi\|125988409\|ref\|NP_0 | 3.1 | | 3.1 | 3.1 | RED protein [Homo sapiens] |
| gi\|33598968\|ref\|NP_00 | 3 | | 3 | 3 | LIM domain only 7 [Homo sapiens] |
| gi\|57164975\|ref\|NP_00 | 2.8 | | 2.8 | 2.8 | Treacher Collins-Franceschetti syndrome 1 isoform b [Homo sapiens] |
| gi\|39777606\|ref\|NP_94 | 2.7 | | 2.7 | 2.7 | Rho guanine nucleotide exchange factor 1 isoform 1 [Homo sapiens] |
| gi\|134142826\|ref\|NP_0 | 2.5 | | 2.5 | 2.5 | pericentriolar material 1 [Homo sapiens] |
| gi\|41281683\|ref\|NP_61 | 2.4 | | 2.4 | 2.4 | disabled homolog 2 interacting protein isoform 2 [Homo sapiens] |
| gi\|89227675\|ref\|NP_00 | 2.4 | | 2.4 | 2.4 | serine/threonine-protein kinase PRP4K [Homo sapiens] |
| gi\|46852388\|ref\|NP_06 | 2.3 | | 2.3 | 2.3 | cell-cycle and apoptosis regulatory protein 1 [Homo sapiens] |
| gi\|44955926\|ref\|NP_05 | 2.1 | | 2.1 | 2.1 | genetic suppressor element 1 [Homo sapiens] |
| gi\|20256780\|ref\|NP_00 | 1.9 | | 1.9 | 1.9 | actinin, alpha 4 [Homo sapiens] |
| gi\|13128860\|ref\|NP_00 | 1.9 | | 1.9 | 1.9 | histone deacetylase 1 [Homo sapiens] |
| gi\|24430146\|ref\|NP_00 | 1.9 | | 1.9 | 1.9 | nucleoporin 153kDa [Homo sapiens] |
| gi\|4755142\|ref\|NP_001 | 1.9 | | 1.9 | 1.9 | inositol polyphosphate phosphatase-like 1 [Homo sapiens] |
| gi\|41322908\|ref\|NP_95 | 1.3 | | 1.8 | 1.8 | plectin 1 isoform 3 [Homo sapiens] |
| gi\|21071056\|ref\|NP_00 | 1.6 | | 1.6 | 1.6 | SWI/SNF-related matrix-associated actin-dependent regulator of chromatin a4 [Homo sapiens] |
| gi\|38708321\|ref\|NP_06 | 1.3 | | 1.3 | 1.3 | INO80 complex homolog 1 [Homo sapiens] |
| gi\|112382252\|ref\|NP_8 | 1.2 | | 1.2 | 1.2 | spectrin, beta, non-erythrocytic 1 isoform 2 [Homo sapiens] |

FIG. 19

| Locus | Normal | | 'Loose' | | Total | Description |
|---|---|---|---|---|---|---|
| | Wild Type 200mM | Mutant 200mM | Wild Type 200mM | Mutant 200mM | | |
| gi\|4150139\|ref\|NP_11 | | | | 19.1 | 19.1 | within bgcn homolog [Homo sapiens] |
| gi\|4758616\|ref\|NP_002 | | | | 14.2 | 14.2 | jun oncogene [Homo sapiens] |
| gi\|15718687\|ref\|NP_00 | | | | 14 | 14 | ribosomal protein S3 [Homo sapiens] |
| gi\|40805825\|ref\|NP_00 | | | | 13.6 | 13.6 | epsilon subunit of coatomer protein complex isoform b [Homo sapiens] |
| gi\|4502901\|ref\|NP_001 | | | | 12.8 | 12.8 | clathrin, light polypeptide isoform a [Homo sapiens] |
| gi\|169216289\|ref\|XP_0 | | | | 12.3 | 12.3 | PREDICTED: similar to mCG49427, partial [Homo sapiens] |
| gi\|28882049\|ref\|NP_00 | | | | 10.9 | 10.9 | replication factor C 2 isoform 2 [Homo sapiens] |
| gi\|4503507\|ref\|NP_001 | | | | 9.3 | 9.3 | eukaryotic translation initiation factor 2, subunit 3 gamma, 52kDa [Homo sapiens] |
| gi\|4506439\|ref\|NP_002 | | | | 9.2 | 9.2 | retinoblastoma binding protein 7 [Homo sapiens] |
| gi\|83281438\|ref\|NP_00 | | | | 8.5 | 8.5 | eukaryotic translation initiation factor 3, subunit 1 alpha, 35kDa [Homo sapiens] |
| gi\|16117791\|ref\|NP_00 | | | | 7.3 | 7.3 | ribosomal protein L35a [Homo sapiens] |
| gi\|39930517\|ref\|NP_61 | | | | 7.1 | 7.1 | sterile alpha motif domain containing 1 [Homo sapiens] |
| gi\|11386183\|ref\|NP_00 | | | | 7 | 7 | WAS protein family, member 2 [Homo sapiens] |
| gi\|58331185\|ref\|NP_00 | | | | 6.8 | 6.8 | chaperonin containing TCP1, subunit 7 isoform b [Homo sapiens] |
| gi\|21361706\|ref\|NP_06 | | | | 6.7 | 6.7 | centrosomal protein 55kDa [Homo sapiens] |
| gi\|4554542\|ref\|NP_84 | | | | 6.1 | 6.1 | ectonucleotide pyrophosphatase/phosphodiesterase 7 [Homo sapiens] |
| gi\|4557757\|ref\|NP_000 | | | | 5.8 | 5.8 | MutL protein homolog 1 [Homo sapiens] |
| gi\|38569466\|ref\|NP_00 | | | | 5.6 | 5.6 | ROD1 regulator of differentiation 1 [Homo sapiens] |
| gi\|14149825\|ref\|NP_11 | | | | 5.5 | 5.5 | MYST histone acetyltransferase 1 isoform 1 [Homo sapiens] |
| gi\|56550053\|ref\|NP_00 | | | | 5.4 | 5.4 | CGG triplet repeat binding protein 1 [Homo sapiens] |
| gi\|124494254\|ref\|NP_0 | | | | 5.1 | 5.1 | ErbB3-binding protein 1 [Homo sapiens] |
| gi\|18860916\|ref\|NP_03 | | | | 5.1 | 5.1 | 5'-3' exoribonuclease 2 [Homo sapiens] |

FIG. 19 (Cont.)

| Locus | | | | | | Description |
|---|---|---|---|---|---|---|
| gi\|5174457\|ref\|NP_006 | | | 5.1 | 5.1 | | kinetochore associated 2 [Homo sapiens] |
| gi\|32129199\|ref\|NP_14 | | | 4.8 | 4.8 | | cytokine induced protein 29 kDa [Homo sapiens] |
| gi\|5802980\|ref\|NP_006 | | | 4.8 | 4.8 | | activating transcription factor 7 [Homo sapiens] |
| gi\|28482617\|ref\|NP_00 | | | 4.8 | 4.8 | | general transcription factor IIIC, polypeptide 2, beta 110kDa [Homo sapiens] |
| gi\|148746220\|ref\|NP_0 | | | 4.6 | 4.6 | | spermatogenesis associated, serine-rich 2 [Homo sapiens] |
| gi\|110431336\|ref\|NP_8 | | | 4.4 | 4.4 | | zinc finger and SCAN domain containing 1 [Homo sapiens] |
| gi\|4503539\|ref\|NP_001 | | | 4.4 | 4.4 | | eukaryotic translation initiation factor 4 gamma, 2 isoform 1 [Homo sapiens] |
| gi\|5902076\|ref\|NP_008 | | | 4.4 | 4.4 | | splicing factor, arginine/serine-rich 1 isoform 1 [Homo sapiens] |
| gi\|27705284\|ref\|NP_057 | | | 4.4 | 4.4 | | anaphase-promoting complex subunit 7 [Homo sapiens] |
| gi\|122937227\|ref\|NP_0 | | | 4.3 | 4.3 | | U2-associated SR140 protein [Homo sapiens] |
| gi\|46447582\|ref\|NP_11 | | | 4.3 | 4.3 | | nuclear factor of activated T-cells, cytoplasmic, calcineurin-dependent 2 interacting protein [Homo sapiens] |
| gi\|7108349\|ref\|NP_036 | | | 4.1 | 4.1 | | hyaluronan-mediated motility receptor isoform a [Homo sapiens] |
| gi\|10863889\|ref\|NP_00 | | | 4 | 4 | | squamous cell carcinoma antigen recognized by T cells 1 [Homo sapiens] |
| gi\|22325364\|ref\|NP_06 | | | 4 | 4 | | ubiquitin associated protein 2 [Homo sapiens] |
| gi\|94538370\|ref\|NP_05 | | | 4 | 4 | | zwotin related factor 1 [Homo sapiens] |
| gi\|69112478\|ref\|NP_036 | | | 3.5 | 3.5 | | karyopherin alpha 6 [Homo sapiens] |
| gi\|4758032\|ref\|NP_004 | | | 3.4 | 3.4 | | coatomer protein complex, subunit beta (beta prime) [Homo sapiens] |
| gi\|5174669\|ref\|NP_006 | | | 3.4 | 3.4 | | sex comb on midleg-like 2 [Homo sapiens] |
| gi\|31563503\|ref\|NP_85 | | | 3.3 | 3.3 | | activity-dependent neuroprotector [Homo sapiens] |
| gi\|28872812\|ref\|NP_05 | | | 3.2 | 3.2 | | MORC family CW-type zinc finger 3 [Homo sapiens] |
| gi\|7662230\|ref\|NP_055 | | | 2.9 | 2.9 | | ring finger protein 40 [Homo sapiens] |
| gi\|110832843\|ref\|NP_0 | | | 2.7 | 2.7 | | TBP-associated factor 4 [Homo sapiens] |
| gi\|13399322\|ref\|NP_07 | | | 2.7 | 2.7 | | N-acetyltransferase 10 [Homo sapiens] |
| gi\|21264343\|ref\|NP_00 | | | 2.7 | 2.7 | | scaffold attachment factor B [Homo sapiens] |
| gi\|4505781\|ref\|NP_000 | | | 2.6 | 2.6 | | phosphorylase kinase, alpha 2 (liver) [Homo sapiens] |
| gi\|42476022\|ref\|NP_06 | | | 2.5 | 2.5 | | tetratricopeptide repeat domain 27 [Homo sapiens] |
| gi\|118493362\|ref\|NP_0 | | | 2.4 | 2.4 | | kinectin 1 isoform b [Homo sapiens] |
| gi\|122937255\|ref\|NP_0 | | | 2.4 | 2.4 | | hypothetical protein LOC57662 isoform 1 [Homo sapiens] |
| gi\|21361794\|ref\|NP_06 | | | 2.4 | 2.4 | | TIP120 protein [Homo sapiens] |
| gi\|39812492\|ref\|NP_94 | | | 2.4 | 2.4 | | TH1-like protein [Homo sapiens] |
| gi\|71044477\|ref\|NP_54 | | | 2.1 | 2.1 | | death inducer-obliterator 1 isoform b [Homo sapiens] |
| gi\|54112429\|ref\|NP_21 | | | 1.9 | 1.9 | | dedicator of cytokinesis 7 [Homo sapiens] |
| gi\|112382257\|ref\|NP_7 | | | 1.8 | 1.8 | | InaD-like protein [Homo sapiens] |
| gi\|116805342\|ref\|NP_0 | | | 1.8 | 1.8 | | human immunodeficiency virus type 1 enhancer binding protein 1 [Homo sapiens] |
| gi\|40807477\|ref\|NP_10 | | | 1.7 | 1.7 | | retinoic acid induced 1 [Homo sapiens] |
| gi\|85797660\|ref\|NP_05 | | | 1.7 | 1.7 | | lunkain b1 [Homo sapiens] |
| gi\|153251865\|ref\|NP_1 | | | 1.4 | 1.4 | | hypothetical protein LOC84226 [Homo sapiens] |
| gi\|81295805\|ref\|NP_00 | | | 1 | 1 | | pericentrin [Homo sapiens] |

FIG. 20

| Locus | Normal | | Loose' | | Total | Description |
|---|---|---|---|---|---|---|
| | Wild Type 200mM | Mutant 200 mM | Wild Type 200mM | Mutant 200mM | | |
| gi\|4507801\|ref\|NP_003 | | | 18.8 | | 18.8 | SMT3 suppressor of mif two 3 homolog 1 isoform a precursor [Homo sapiens] |
| gi\|4506707\|ref\|NP_001 | | | 15.2 | | 15.2 | ribosomal protein S25 [Homo sapiens] |
| gi\|4758086\|ref\|NP_004 | | | 13 | | 13 | cysteine and glycine-rich protein 1 [Homo sapiens] |
| gi\|13390863\|ref\|NP_6 | | | 9.7 | | 9.7 | SWI/SNF-related matrix-associated actin-dependent regulator of chromatin d1 isoform b [Homo sapiens] |
| gi\|4506649\|ref\|NP_000 | | | 7.9 | | 7.9 | ribosomal protein L3 isoform a [Homo sapiens] |
| gi\|62414289\|ref\|NP_00 | | | 6.4 | | 6.4 | vimentin [Homo sapiens] |
| gi\|34577110\|ref\|NP_90 | | | 6 | | 6 | aldolase A [Homo sapiens] |
| gi\|5174545\|ref\|NP_005 | | | 5.2 | | 5.2 | myocyte enhancer factor 2D [Homo sapiens] |
| gi\|4557843\|ref\|NP_000 | | | 4.9 | | 4.9 | regulatory factor X, 5 [Homo sapiens] |
| gi\|31563338\|ref\|NP_00 | | | 4.5 | | 4.5 | forkhead box K2 [Homo sapiens] |
| gi\|6005942\|ref\|NP_009 | | | 4.5 | | 4.5 | valosin-containing protein [Homo sapiens] |
| gi\|4885237\|ref\|NP_005 | | | 4.4 | | 4.4 | forkhead box C2 [Homo sapiens] |
| gi\|33457336\|ref\|NP_07 | | | 4.3 | | 4.3 | chromosome 14 open reading frame 4 [Homo sapiens] |
| gi\|62243332\|ref\|NP_00 | | | 4.2 | | 4.2 | MAD1-like 1 protein [Homo sapiens] |
| gi\|37655183\|ref\|NP_00 | | | 3.8 | | 3.8 | N-myc downstream regulated gene 1 [Homo sapiens] |
| gi\|148806928\|ref\|NP_0 | | | 3.5 | | 3.5 | hypothetical protein LOC57482 [Homo sapiens] |
| gi\|31077211\|ref\|NP_85 | | | 3.4 | | 3.4 | hypoxia-inducible factor 1, alpha subunit isoform 2 [Homo sapiens] |
| gi\|70608155\|ref\|NP_00 | | | 3.3 | | 3.3 | phosphodiesterase 3A, cGMP-inhibited [Homo sapiens] |
| gi\|96974985\|ref\|NP_06 | | | 3.2 | | 3.2 | coiled-coil and C2 domain containing 1A [Homo sapiens] |
| gi\|13514809\|ref\|NP_00 | | | 3 | | 3 | DEAD (Asp-Glu-Ala-Asp) box polypeptide 3, Y-linked [Homo sapiens] |
| gi\|38424073\|ref\|NP_05 | | | 2.9 | | 2.9 | pleckstrin homology-like domain, family B, member 1 [Homo sapiens] |
| gi\|32489879\|ref\|NP_00 | | | 2.2 | | 2.2 | adaptor-related protein complex 3, beta 1 subunit [Homo sapiens] |
| gi\|24430149\|ref\|NP_70 | | | 2.1 | | 2.1 | nucleoporin 155kDa isoform 1 [Homo sapiens] |
| gi\|45007007\|ref\|NP_00 | | | 2 | | 2 | 2'-5'oligoadenylate synthetase 3 [Homo sapiens] |
| gi\|7661878\|ref\|NP_055 | | | 1.5 | | 1.5 | kinesin family member 14 [Homo sapiens] |
| gi\|157817073\|ref\|NP_0 | | | 1.4 | | 1.4 | Cdc2-related kinase, arginine/serine-rich isoform 2 [Homo sapiens] |
| gi\|117553586\|ref\|NP_0 | | | 1.3 | | 1.3 | dedicator of cytokinesis 5 [Homo sapiens] |
| gi\|82830428\|ref\|NP_11 | | | 1.2 | | 1.2 | jmo-4-like isoform b [Homo sapiens] |
| gi\|118572613\|ref\|NP_0 | | | 1 | | 1 | splicing coactivator subunit SRm300 [Homo sapiens] |
| gi\|38230498\|ref\|NP_05 | | | 0.4 | | 0.4 | sacsin [Homo sapiens] |

FIG. 21

| Locus | Normal | | Loose' | | Total | Description |
|---|---|---|---|---|---|---|
| | Wild Type 200mM | Mutant 200mM | Wild Type 200mM | Mutant 200mM | | |
| gi|4505763|ref|NP_000 | 14.9 | 64.3 | 18.7 | 73.1 | 74.8 | phosphoglycerate kinase 1 [Homo sapiens] |
| gi|29788785|ref|NP_82 | 15.3 | 48.2 | 15.3 | 54.5 | 54.5 | tubulin, beta [Homo sapiens] |
| gi|4504517|ref|NP_001 | 13.2 | 37.1 | 13.2 | 37.1 | 45.4 | heat shock 27kDa protein 1 [Homo sapiens] |
| gi|4757756|ref|NP_004 | 7.1 | 41.3 | 7.1 | 43.4 | 43.7 | annexin A2 isoform 2 [Homo sapiens] |
| gi|4506695|ref|NP_001 | 16.6 | 40.7 | 16.6 | 40.7 | 40.7 | ribosomal protein S19 [Homo sapiens] |
| gi|5453854|ref|NP_006 | 7.6 | 28.4 | 7.6 | 38.8 | 38.8 | poly(rC) binding protein 1 [Homo sapiens] |
| gi|4506661|ref|NP_000 | 18.4 | 35 | 23.7 | 35.3 | 38 | ribosomal protein L7a [Homo sapiens] |
| gi|4504147|ref|NP_002 | 19.9 | 29.6 | 19.9 | 36.7 | 36.7 | heterogeneous nuclear ribonucleoprotein A2/B1 isoform A2 [Homo sapiens] |
| gi|33286422|ref|NP_87 | 5.5 | 30.1 | 5.5 | 31.6 | 34.7 | pyruvate kinase, muscle isoform 2 [Homo sapiens] |
| gi|16507237|ref|NP_00 | 10.4 | 28.1 | 10.4 | 28.1 | 34.1 | heat shock 70kDa protein 5 [Homo sapiens] |
| gi|4506629|ref|NP_000 | 24.5 | 25.2 | 29.6 | 25.2 | 32.1 | ribosomal protein L29 [Homo sapiens] |
| gi|17105394|ref|NP_00 | 31.4 | 23.1 | 31.4 | 23.1 | 31.4 | ribosomal protein L23a [Homo sapiens] |
| gi|4885049|ref|NP_005 | 15.1 | 30.5 | 17.8 | 30.5 | 30.5 | cardiac muscle alpha actin 1 proprotein [Homo sapiens] |
| gi|40354192|ref|NP_00 | 6.7 | 28.8 | 6.7 | 30.3 | 30.3 | keratin 10 [Homo sapiens] keratin 10; cytokeratin 10 [Homo sapiens] |
| gi|16579885|ref|NP_00 | 9.1 | 27.2 | 9.1 | 27.2 | 29.7 | ribosomal protein L4 [Homo sapiens] |
| gi|10835063|ref|NP_00 | 17.7 | 28.9 | 27.2 | 28.9 | 28.9 | nucleophosmin 1 isoform 1 [Homo sapiens] |
| gi|4885379|ref|NP_005 | 28.8 | 28.3 | 28.8 | 28.3 | 28.8 | histone cluster 1, H1e [Homo sapiens] |
| gi|46409270|ref|NP_99 | 8.4 | 25.8 | 8.4 | 28.7 | 28.7 | tubulin, alpha 3c [Homo sapiens] |
| gi|67189747|ref|NP_00 | 15.3 | 22.9 | 15.3 | 22.9 | 28.5 | ribosomal protein L6 [Homo sapiens] |
| gi|5729877|ref|NP_006 | 5.1 | 25.1 | 5.1 | 28.3 | 28.3 | heat shock 70kDa protein 8 isoform 1 [Homo sapiens] |
| gi|34932414|ref|NP_03 | 20.8 | 19.3 | 20.8 | 19.3 | 27.4 | non-POU domain containing, octamer-binding [Homo sapiens] |
| gi|119395750|ref|NP_0 | 10.7 | 26.7 | 12.1 | 26.7 | 26.7 | keratin 1 [Homo sapiens] |
| gi|148833484|ref|NP_0 | 8.2 | 21.8 | 8.2 | 26.6 | 26.6 | poly(rC)-binding protein 2 isoform c [Homo sapiens] |
| gi|4506663|ref|NP_000 | 23.3 | 21.8 | 23.3 | 21.8 | 26.1 | ribosomal protein L8 [Homo sapiens] |
| gi|14670356|ref|NP_00 | 7.7 | 23.1 | 8.7 | 23.1 | 26 | general transcription factor II, i isoform 4 [Homo sapiens] |
| gi|4503471|ref|NP_001 | 6.9 | 25.5 | 6.9 | 25.5 | 25.5 | eukaryotic translation elongation factor 1 alpha 1 [Homo sapiens] |
| gi|55956899|ref|NP_00 | 5.1 | 25 | 6.7 | 25 | 25 | keratin 9 [Homo sapiens] |
| gi|78000183|ref|NP_00 | 9.8 | 20.5 | 9.8 | 24.2 | 24.2 | ribosomal protein L14 [Homo sapiens] |
| gi|10645195|ref|NP_06 | 21.5 | 23.8 | 21.5 | 23.8 | 23.8 | histone cluster 1, H2ae [Homo sapiens] |
| gi|4506649|ref|NP_000 | 5.7 | 17.9 | 5.7 | 19.9 | 22.8 | ribosomal protein L3 isoform a [Homo sapiens] |
| gi|4506741|ref|NP_001 | 16 | 14.4 | 16 | 14.4 | 22.7 | ribosomal protein S7 [Homo sapiens] |
| gi|47132620|ref|NP_00 | 11.9 | 22.4 | 13.3 | 22.4 | 22.4 | keratin 2 [Homo sapiens] |
| gi|4506619|ref|NP_000 | 8.9 | 22.3 | 8.9 | 22.3 | 22.3 | ribosomal protein L24 [Homo sapiens] |
| gi|5123454|ref|NP_005 | 7 | 18.9 | 7 | 22 | 22 | heat shock 70kDa protein 1A [Homo sapiens] |
| gi|14165439|ref|NP_00 | 6.5 | 17.2 | 12.7 | 17.2 | 21.6 | heterogeneous nuclear ribonucleoprotein K isoform a [Homo sapiens] |
| gi|4506743|ref|NP_001 | 12 | 15.9 | 12 | 15.9 | 21.6 | ribosomal protein S8 [Homo sapiens] |
| gi|116256489|ref|NP_0 | 11.4 | 14.6 | 11.4 | 18.5 | 21.1 | septin 9 isoform c [Homo sapiens] |
| gi|4501887|ref|NP_001 | 10.4 | 21.1 | 10.4 | 21.1 | 21.1 | actin, gamma 1 propeptide [Homo sapiens] |
| gi|71361682|ref|NP_00 | 4.8 | 16.9 | 5.2 | 19.4 | 21.1 | nuclear mitotic apparatus protein 1 [Homo sapiens] |
| gi|4826998|ref|NP_005 | 7.9 | 19.8 | 7.9 | 19.9 | 20.4 | splicing factor proline/glutamine rich (polypyrimidine tract binding protein associated) [Homo sapiens] |
| gi|74136883|ref|NP_11 | 5.5 | 17.6 | 6.3 | 18.2 | 20.4 | heterogeneous nuclear ribonucleoprotein U isoform a [Homo sapiens] |
| gi|4503249|ref|NP_003 | 9.6 | 16.5 | 9.6 | 16.5 | 20.3 | DEK oncogene [Homo sapiens] |
| gi|37760401|ref|NP_00 | 8.4 | 20 | 8.4 | 20 | 20 | thymopoietin isoform gamma [Homo sapiens] |
| gi|30089919|ref|NP_83 | 7.7 | 19.9 | 7.7 | 19.9 | 19.9 | DNA polymerase delta interacting protein 3 isoform 2 [Homo sapiens] |
| gi|61743954|ref|NP_00 | 2.2 | 14.2 | 2.9 | 17.4 | 18.3 | AHNAK nucleoprotein isoform 1 [Homo sapiens] |
| gi|9845502|ref|NP_002 | 10.2 | 9.5 | 10.2 | 12.2 | 18 | ribosomal protein SA [Homo sapiens] |
| gi|48596949|ref|NP_0 | 2.9 | 14.9 | 4 | 17.9 | 17.9 | nucleolar and coiled-body phosphoprotein 1 [Homo sapiens] |
| gi|114155148|ref|NP_0 | 10.9 | 12.1 | 10.9 | 12.1 | 17.4 | tropomyosin 3 isoform 5 [Homo sapiens] |
| gi|14141152|ref|NP_00 | 7.3 | 15.5 | 7.3 | 15.5 | 17.1 | heterogeneous nuclear ribonucleoprotein M isoform a [Homo sapiens] |
| gi|4506597|ref|NP_000 | 6.1 | 16.4 | 6.1 | 16.4 | 17 | ribosomal protein L12 [Homo sapiens] |
| gi|4758138|ref|NP_004 | 5.4 | 15.3 | 5.4 | 15.8 | 15.8 | DEAD (Asp-Glu-Ala-Asp) box polypeptide 5 [Homo sapiens] |
| gi|14389309|ref|NP_11 | 6 | 15.4 | 6 | 15.4 | 15.6 | tubulin alpha 6 [Homo sapiens] |
| gi|38201730|ref|NP_00 | 4 | 13.3 | 4 | 13.3 | 15.2 | DEAD box polypeptide 17 isoform 1 [Homo sapiens] |
| gi|30581135|ref|NP_00 | 2.2 | 10.9 | 2.2 | 13.1 | 14.2 | structural maintenance of chromosomes 1A [Homo sapiens] |
| gi|62750354|ref|NP_95 | 3.8 | 14.2 | 5.9 | 14.2 | 14.2 | matrin 3 [Homo sapiens] |
| gi|4507457|ref|NP_003 | 5.3 | 10.3 | 7 | 12.2 | 13.9 | transferrin receptor [Homo sapiens] |
| gi|5453555|ref|NP_006 | 5.6 | 13.4 | 5.6 | 13.4 | 13.4 | ran-related nuclear protein [Homo sapiens] |
| gi|4885399|ref|NP_005 | 4.1 | 8.1 | 6.2 | 9.4 | 13.3 | structural maintenance of chromosomes 3 [Homo sapiens] |
| gi|31543397|ref|NP_62 | 7.9 | 13.2 | 7.9 | 13.2 | 13.2 | phosphoglycerate kinase 2 [Homo sapiens] |
| gi|4506491|ref|NP_002 | 10.5 | 6.1 | 10.5 | 6.1 | 12.9 | replication factor C 4 [Homo sapiens] |
| gi|5730027|ref|NP_006 | 7.9 | 11.1 | 9.3 | 12.4 | 12.4 | KH domain containing, RNA binding, signal transduction associated 1 [Homo sapiens] |
| gi|6912676|ref|NP_036 | 5.2 | 9.5 | 5.2 | 9.5 | 12.3 | SKI-interacting protein [Homo sapiens] |
| gi|100816392|ref|NP_0 | 3.5 | 5.8 | 3.5 | 10.1 | 11.5 | far upstream element (FUSE) binding protein 3 [Homo sapiens] |
| gi|40548408|ref|NP_95 | 2.8 | 9.4 | 2.8 | 10.3 | 11.5 | p30 DBC protein [Homo sapiens] |
| gi|10677479|ref|NP_00 | 2.4 | 10.1 | 2.4 | 11.2 | 11.2 | CDC5-like [Homo sapiens] |
| gi|88953883|ref|XP_93 | 10.6 | 11 | 10.6 | 11 | 11 | PREDICTED: similar to heterogeneous nuclear ribonucleoprotein A1 [Homo sapiens] |
| gi|57164977|ref|NP_00 | 4 | 7.9 | 4.6 | 7.9 | 9.6 | Treacher Collins-Franceschetti syndrome 1 isoform a [Homo sapiens] |
| gi|116063573|ref|NP_0 | 2.3 | 7.1 | 2.3 | 8.3 | 9.3 | filamin A, alpha isoform 1 [Homo sapiens] |
| gi|5729730|ref|NP_006 | 4 | 6.9 | 4 | 6.9 | 9.3 | apoptosis inhibitor 5 [Homo sapiens] |
| gi|4506621|ref|NP_000 | 9 | 9 | 9 | 9 | 9 | ribosomal protein L26 [Homo sapiens] |
| gi|98986457|ref|NP_00 | 2.4 | 6.2 | 2.4 | 8.4 | 8.8 | host cell factor 1 [Homo sapiens] |
| gi|54607053|ref|NP_00 | 1.2 | 6.9 | 1.2 | 8.3 | 8.3 | GCN1 general control of amino-acid synthesis 1-like 1 [Homo sapiens] |
| gi|4557495|ref|NP_001 | 5.7 | 4 | 5.7 | 4 | 7.7 | cleavage stimulation factor subunit 3 isoform 1 [Homo sapiens] |
| gi|119395754|ref|NP_0 | 3.6 | 5.6 | 3.6 | 5.6 | 7.3 | keratin 5 [Homo sapiens] |
| gi|69217303|ref|XP_0 | 3.3 | 5.7 | 3.3 | 5.7 | 7.3 | PREDICTED: hypothetical LOC389901 [Homo sapiens] |
| gi|113430845|ref|XP_0 | 0.9 | 5.9 | 0.9 | 6.4 | 6.4 | PREDICTED: similar to DNA dependent protein kinase catalytic subunit [Homo sapiens] |
| gi|39930353|ref|NP_05 | 2.9 | 3.4 | 2.9 | 4.4 | 5.7 | superkiller viralicidic activity 2-like 2 [Homo sapiens] |
| gi|38201625|ref|NP_93 | 2.5 | 3.2 | 2.5 | 4.4 | 4.4 | eukaryotic translation initiation factor 4 gamma, 1 isoform 3 [Homo sapiens] |
| gi|6678271|ref|NP_031 | 4.3 | 4.3 | 4.3 | 4.3 | 4.3 | TAR DNA binding protein [Homo sapiens] |
| gi|19913406|ref|NP_00 | 1.5 | 2.6 | 1.5 | 2.6 | 3.3 | DNA topoisomerase II, alpha isozyme [Homo sapiens] |

FIG. 22

| Locus | Normal | | Loose' | | Total | Description |
|---|---|---|---|---|---|---|
| | Wild Type 200nM | Mutant 200mM | Wild Type 200nM | Mutant 200mM | | |
| gi|28173560|ref|NP_77 | | 37.9 | 11.7 | 44.7 | 44.7 | histone cluster 4, H4 [Homo sapiens] |
| gi|5032051|ref|NP_005 | | 36.4 | 8.6 | 36.4 | 37.7 | ribosomal protein S14 [Homo sapiens] |
| gi|4506623|ref|NP_000 | | 23.6 | 8.8 | 31.8 | 31.8 | ribosomal protein L27a [Homo sapiens] |
| gi|14670268|ref|NP_00 | | 17.1 | 9.5 | 21.6 | 26.3 | RD RNA-binding protein [Homo sapiens] |
| gi|67944630|ref|NP_00 | | 26 | 13.5 | 26 | 26 | ribosomal protein L9 [Homo sapiens] |
| gi|4506243|ref|NP_002 | | 21 | 6.3 | 21 | 23.2 | polypyrimidine tract-binding protein 1 isoform a [Homo sapiens] |
| gi|20357552|ref|NP_00 | | 17.8 | 5.1 | 22.5 | 22.5 | cortactin isoform a [Homo sapiens] |
| gi|5995678|ref|NP_00 | | 15.8 | 1.4 | 16.2 | 16.2 | nucleolin [Homo sapiens] |
| gi|10863945|ref|NP_06 | | 11.1 | 4.2 | 15.3 | 15.3 | ATP-dependent DNA helicase II [Homo sapiens] |
| gi|156523968|ref|NP_0 | | 11.4 | 3.2 | 11.4 | 14.6 | poly (ADP-ribose) polymerase family, member 1 [Homo sapiens] |
| gi|169206894|ref|XP_0 | | 13.6 | 6.1 | 13.6 | 13.6 | PREDICTED: similar to S19 ribosomal protein [Homo sapiens] |
| gi|169211155|ref|XP_0 | | 9.5 | 7.9 | 9.5 | 9.5 | PREDICTED: similar to Karyopherin alpha 2 (RAG cohort 1, importin alpha 1) isoform 1 [Homo sapiens] |
| gi|115298682|ref|NP_0 | | 1.5 | 0.9 | 3.3 | 3.7 | HBxAg transactivated protein 2 [Homo sapiens] |

FIG. 23

| Locus | Normal | | Loose' | | Total | Description |
|---|---|---|---|---|---|---|
| | Wild Type 200nM | Mutant 200mM | Wild Type 200nM | Mutant 200mM | | |
| gi|28558998|ref|NP_78 | 15.2 | | 15.2 | 14.2 | 19.3 | polypyrimidine tract-binding protein 1 isoform d [Homo sapiens] |

FIG. 24

| Locus | Normal | | Loose' | | Total | Description |
|---|---|---|---|---|---|---|
| | Wild Type 200nM | Mutant 200mM | Wild Type 200nM | Mutant 200mM | | |
| gi|66346685|ref|NP_05 | | | 7.5 | 7 | 12.4 | SERPINE1 mRNA binding protein 1 isoform 4 [Homo sapiens] |

FIG. 25

| Locus | Normal | | Loose' | | Total | Description |
|---|---|---|---|---|---|---|
| | Wild Type 200nM | Mutant 200mM | Wild Type 200nM | Mutant 200mM | | |
| gi|15718687|ref|NP_00 | | 39.9 | | 39.9 | 39.9 | ribosomal protein S3 [Homo sapiens] |
| gi|4506667|ref|NP_000 | | 36.5 | | 36.5 | 36.5 | ribosomal protein P2 [Homo sapiens] |
| gi|4504277|ref|NP_003 | | 35.7 | | 35.7 | 35.7 | histone cluster 2, H2be [Homo sapiens] |
| gi|4506613|ref|NP_000 | | 25.8 | | 35.2 | 35.2 | ribosomal protein L22 proprotein [Homo sapiens] |
| gi|78214522|ref|NP_00 | | 34.3 | | 34.3 | 34.3 | ribosomal protein L38 [Homo sapiens] |
| gi|4758950|ref|NP_000 | | 33.8 | | 33.8 | 33.8 | peptidylprolyl isomerase B precursor [Homo sapiens] |
| gi|14999961|ref|NP_0 | | 33.1 | | 33.1 | 33.1 | signal recognition particle 14kDa (homologous Alu RNA binding protein) [Homo sapiens] |
| gi|4506607|ref|NP_000 | | 20.2 | | 31.4 | 31.4 | ribosomal protein L18 [Homo sapiens] |
| gi|4506623|ref|NP_000 | | 16.2 | | 30.9 | 30.9 | ribosomal protein L27 [Homo sapiens] |
| gi|17158044|ref|NP_00 | | 25.7 | | 30.1 | 30.1 | ribosomal protein S6 [Homo sapiens] |
| gi|4507129|ref|NP_003 | | 17.4 | | 29.3 | 29.3 | small nuclear ribonucleoprotein polypeptide E [Homo sapiens] |
| gi|4503571|ref|NP_001 | | 23.7 | | 28.6 | 28.6 | enolase 1 [Homo sapiens] |
| gi|169215435|ref|XP_0 | | 26 | | 26 | 26 | PREDICTED: similar to peptidylprolyl isomerase A-like [Homo sapiens] |
| gi|29294624|ref|NP_80 | | 24.6 | | 24.6 | 24.6 | small nuclear ribonucleoprotein polypeptide D2 [Homo sapiens] |
| gi|38455427|ref|NP_00 | | 19.9 | | 23.9 | 23.9 | chaperonin containing TCP1, subunit 4 (delta) [Homo sapiens] |
| gi|114796640|ref|NP_0 | | 12.4 | | 23.8 | 23.8 | regulator of chromosome condensation 1 [Homo sapiens] |
| gi|14916501|ref|NP_14 | | 23.8 | | 23.8 | 23.8 | ribosomal protein S24 isoform a [Homo sapiens] |
| gi|75709220|ref|NP_00 | | 23.7 | | 23.7 | 23.7 | cleavage stimulation factor subunit 1 [Homo sapiens] |
| gi|4506713|ref|NP_002 | | 19.2 | | 23.1 | 23.1 | ubiquitin and ribosomal protein S27a precursor [Homo sapiens] |
| gi|4506693|ref|NP_001 | | 23 | | 23 | 23 | ribosomal protein S17 [Homo sapiens] |
| gi|4826898|ref|NP_005 | | 22.9 | | 22.9 | 22.9 | profilin 1 [Homo sapiens] |
| gi|55770864|ref|NP_00 | | 22.6 | | 22.6 | 22.6 | THO complex 4 [Homo sapiens] |
| gi|4506667|ref|NP_000 | | 10.7 | | 21.8 | 21.8 | ribosomal protein P0 [Homo sapiens] |
| gi|169184561|ref|XP_0 | | 17.2 | | 21.5 | 21.5 | PREDICTED: similar to v-fos transformation effector protein isoform 1 [Homo sapiens] |
| gi|169211550|ref|XP_0 | | 17.9 | | 21 | 21 | PREDICTED: similar to septin 9 [Homo sapiens] |
| gi|41150665|ref|XP_37 | | 11.4 | | 20.9 | 20.9 | PREDICTED: similar to RPL13 protein isoform 1 [Homo sapiens] |
| gi|5454106|ref|NP_006 | | 20.6 | | 20.6 | 20.6 | TBP-related factor 10 [Homo sapiens] |
| gi|34577110|ref|NP_90 | | 20.3 | | 20.3 | 20.3 | aldolase A [Homo sapiens] |
| gi|4506697|ref|NP_001 | | 10.9 | | 20.2 | 20.2 | ribosomal protein S20 [Homo sapiens] |
| gi|16117796|ref|NP_37 | | 20 | | 20 | 20 | ribosomal protein L36 [Homo sapiens] |
| gi|20127519|ref|NP_03 | | 14.2 | | 19.8 | 19.8 | TPX2, microtubule-associated protein homolog [Homo sapiens] |
| gi|4506723|ref|NP_000 | | 19.7 | | 19.7 | 19.7 | ribosomal protein S3a [Homo sapiens] |
| gi|62865614|ref|NP_00 | | 19.7 | | 19.7 | 19.7 | TAF9 RNA polymerase II isoform a [Homo sapiens] |
| gi|4504919|ref|NP_002 | | 19.3 | | 19.3 | 19.3 | keratin 8 [Homo sapiens]; keratin 8; cytokeratin 8; keratin, type II cytoskeletal 8 [Homo sapiens] |
| gi|4506707|ref|NP_001 | | 19.2 | | 19.2 | 19.2 | ribosomal protein S25 [Homo sapiens] |
| gi|89033540|ref|XP_94 | | 15.3 | | 19.2 | 19.2 | PREDICTED: similar to 23 kD highly basic protein isoform 1 [Homo sapiens] |
| gi|56549640|ref|NP_00 | | 18.3 | | 19.1 | 19.1 | septin 2 [Homo sapiens] |
| gi|4503841|ref|NP_001 | | 12 | | 18.7 | 18.7 | ATP-dependent DNA helicase II, 70 kDa subunit [Homo sapiens] |
| gi|15431290|ref|NP_00 | | 18.5 | | 18.5 | 18.5 | ribosomal protein L11 [Homo sapiens] |
| gi|46218913|ref|NP_00 | | 18.4 | | 18.4 | 18.4 | calcyclin binding protein isoform 2 [Homo sapiens] |
| gi|5901926|ref|NP_008 | | 17.6 | | 17.6 | 17.6 | cleavage and polyadenylation specific factor 5 [Homo sapiens] |
| gi|4759160|ref|NP_004 | | 10.3 | | 17.5 | 17.5 | small nuclear ribonucleoprotein polypeptide D3 [Homo sapiens] |
| gi|46367787|ref|NP_00 | | 12.6 | | 17.3 | 17.3 | poly(A) binding protein, cytoplasmic 1 [Homo sapiens] |
| gi|38327552|ref|NP_93 | | 13.5 | | 16.7 | 16.7 | Ras-GTPase-activating protein SH3-domain-binding protein [Homo sapiens] |

FIG. 25 (Cont.)

| | | | | |
|---|---|---|---|---|
| gi|4506725|ref|NP_000 | 16.7 | 16.7 | 16.7 | ribosomal protein S4, X-linked X isoform [Homo sapiens] |
| gi|4507555|ref|NP_003 | 16.6 | 16.6 | 16.6 | thymopoietin isoform alpha [Homo sapiens] |
| gi|4557493|ref|NP_001 | 16.6 | 16.6 | 16.6 | cleavage stimulation factor subunit 2 [Homo sapiens] |
| gi|113430469|ref|XP_9 | 16.3 | 16.3 | 16.3 | PREDICTED: similar to ribosomal protein S23 [Homo sapiens] |
| gi|15431295|ref|NP_15 | 10.9 | 16.1 | 16.1 | ribosomal protein L13 [Homo sapiens] |
| gi|5031973|ref|NP_005 | 16.1 | 16.1 | 16.1 | protein disulfide isomerase-associated 6 [Homo sapiens] |
| gi|23308577|ref|NP_00 | 9.8 | 15.9 | 15.9 | phosphoglycerate dehydrogenase [Homo sapiens] |
| gi|4506901|ref|NP_003 | 15.9 | 15.9 | 15.9 | splicing factor, arginine/serine-rich 3 [Homo sapiens] |
| gi|169168866|ref|XP_0 | 15.8 | 15.8 | 15.8 | PREDICTED: similar to ribosomal protein L10a [Homo sapiens] |
| gi|4506669|ref|NP_001 | 15.8 | 15.8 | 15.8 | ribosomal protein S16 [Homo sapiens] |
| gi|169214231|ref|XP_0 | 15.7 | 15.7 | 15.7 | PREDICTED: similar to hCG2027326 [Homo sapiens] |
| gi|4503507|ref|NP_001 | 15.5 | 15.5 | 15.5 | eukaryotic translation initiation factor 2, subunit 3 gamma, 52kDa [Homo sapiens] |
| gi|58331185|ref|NP_00 | 9.4 | 15.3 | 15.3 | chaperonin containing TCP1, subunit 7 isoform b [Homo sapiens] |
| gi|14591909|ref|NP_00 | 15.2 | 15.2 | 15.2 | ribosomal protein L5 [Homo sapiens] |
| gi|32189392|ref|NP_00 | 15.2 | 15.2 | 15.2 | peroxiredoxin 2 isoform a [Homo sapiens] |
| gi|5730023|ref|NP_006 | 14.9 | 14.9 | 14.9 | RuvB-like 2 [Homo sapiens] |
| gi|22035579|ref|NP_66 | 12.6 | 14.8 | 14.8 | septin 6 isoform A [Homo sapiens] |
| gi|580311|ref|NP_006 | 10.1 | 14.7 | 14.7 | EBNA1 binding protein 2 [Homo sapiens] |
| gi|4506668|ref|NP_001 | 14.6 | 14.6 | 14.6 | ribosomal protein S11 [Homo sapiens] |
| gi|4506411|ref|NP_002 | 10.9 | 14.5 | 14.5 | Ran GTPase activating protein 1 [Homo sapiens] |
| gi|4506753|ref|NP_003 | 14.5 | 14.5 | 14.5 | RuvB-like 1 [Homo sapiens] |
| gi|113429532|ref|XP_9 | 14 | 14 | 14 | PREDICTED: similar to ribosomal protein S10 [Homo sapiens] |
| gi|4504285|ref|NP_003 | 14 | 14 | 14 | histone cluster 1, H3c [Homo sapiens] |
| gi|4506669|ref|NP_000 | 14 | 14 | 14 | ribosomal protein P1 isoform 1 [Homo sapiens] |
| gi|13904866|ref|NP_00 | 13.9 | 13.9 | 13.9 | ribosomal protein L28 [Homo sapiens] |
| gi|169209212|ref|XP_0 | 13.9 | 13.9 | 13.9 | PREDICTED: hypothetical protein [Homo sapiens] |
| gi|5031755|ref|NP_005 | 11.8 | 13.9 | 13.9 | heterogeneous nuclear ribonucleoprotein R isoform 2 [Homo sapiens] |
| gi|32129199|ref|NP_14 | 9.5 | 13.8 | 13.8 | cytokine induced protein 29 kDa [Homo sapiens] |
| gi|40354195|ref|NP_95 | 13.5 | 13.5 | 13.5 | keratin 18 [Homo sapiens] keratin 18, cytokeratin 18 [Homo sapiens] |
| gi|4503529|ref|NP_001 | 9.9 | 13.5 | 13.5 | eukaryotic translation initiation factor 4A isoform 1 [Homo sapiens] |
| gi|42544172|ref|NP_97 | 13.4 | 13.4 | 13.4 | E74-like factor 2 (ets domain transcription factor) isoform 1 [Homo sapiens] |
| gi|5729939|ref|NP_006 | 13.4 | 13.4 | 13.4 | cleavage and polyadenylation specific factor 4, 30kDa isoform 1 [Homo sapiens] |
| gi|27436948|ref|NP_73 | 13.2 | 13.2 | 13.2 | lamin A/C isoform 3 [Homo sapiens] |
| gi|2104037|ref|NP_00 | 13.1 | 13.1 | 13.1 | DEAD (Asp-Glu-Ala-Asp) box polypeptide 39 [Homo sapiens] |
| gi|113416101|ref|XP_0 | 12.8 | 12.8 | 12.8 | PREDICTED: similar to 40S ribosomal protein S12 [Homo sapiens] |
| gi|4757718|ref|NP_004 | 12.8 | 12.8 | 12.8 | actin-like 6A isoform 1 [Homo sapiens] |
| gi|21361657|ref|NP_00 | 10.3 | 12.7 | 12.7 | protein disulfide isomerase-associated 3 precursor [Homo sapiens] |
| gi|110347425|ref|NP_0 | 7.9 | 12.4 | 12.4 | structural maintenance of chromosomes 2-like 1 [Homo sapiens] |
| gi|42558279|ref|NP_81 | 9.7 | 12.4 | 12.4 | tubulin, beta 8 [Homo sapiens] |
| gi|67782365|ref|NP_00 | 7.7 | 12.4 | 12.4 | keratin 7 [Homo sapiens] |
| gi|24234747|ref|NP_00 | 12.3 | 12.3 | 12.3 | interleukin enhancer binding factor 2 [Homo sapiens] |
| gi|146231942|ref|NP_0 | 7.4 | 12.2 | 12.2 | catenin, delta 1 isoform 1A [Homo sapiens] |
| gi|4502643|ref|NP_001 | 12.2 | 12.2 | 12.2 | chaperonin containing TCP1, subunit 6A isoform a [Homo sapiens] |
| gi|19913363|ref|NP_00 | 12.1 | 12.1 | 12.1 | Wolf-Hirschhorn syndrome candidate 2 protein [Homo sapiens] |
| gi|169165117|ref|XP_0 | 12 | 12 | 12 | PREDICTED: hypothetical protein [Homo sapiens] |
| gi|4507677|ref|NP_003 | 9.6 | 12 | 12 | tumor rejection antigen (gp96) 1 [Homo sapiens] |
| gi|62243332|ref|NP_00 | 9.1 | 11.7 | 11.7 | MAD1-like 1 protein [Homo sapiens] |
| gi|13540586|ref|NP_11 | 11.6 | 11.6 | 11.6 | hypothetical protein LOC81556 [Homo sapiens] |
| gi|12317375|ref|NP_5 | 10.1 | 11.4 | 11.4 | RAVER1 [Homo sapiens] |
| gi|19923502|ref|NP_06 | 11.4 | 11.4 | 11.4 | GATA zinc finger domain containing 2A [Homo sapiens] |
| gi|4505117|ref|NP_003 | 11.4 | 11.4 | 11.4 | methyl-CpG binding domain protein 2 isoform 1 [Homo sapiens] |
| gi|41327773|ref|NP_05 | 10.1 | 11.3 | 11.3 | DEAD (Asp-Glu-Ala-Asp) box polypeptide 46 [Homo sapiens] |
| gi|21704269|ref|NP_66 | 11.2 | 11.2 | 11.2 | MAX protein isoform e [Homo sapiens] |
| gi|4502009|ref|NP_003 | 11.2 | 11.2 | 11.2 | aryl hydrocarbon receptor interacting protein [Homo sapiens] |
| gi|4504809|ref|NP_002 | 11.2 | 11.2 | 11.2 | jun B proto-oncogene [Homo sapiens] |
| gi|89057301|ref|XP_94 | 11.1 | 11.1 | 11.1 | PREDICTED: ribosomal protein L34-like [Homo sapiens] |
| gi|116812577|ref|NP_0 | 11 | 11 | 11 | LUC7-like 2 [Homo sapiens] |
| gi|82546824|ref|NP_06 | 10.9 | 10.9 | 10.9 | forkhead box K1 [Homo sapiens] |
| gi|30795193|ref|NP_84 | 10.7 | 10.7 | 10.7 | septin 10 isoform 2 [Homo sapiens] |
| gi|1644542|ref|NP_44 | 10.6 | 10.6 | 10.6 | secretory carrier membrane protein 3 isoform 2 [Homo sapiens] |
| gi|14835233|ref|NP_0 | 8.5 | 10.5 | 10.5 | cell division cycle 10 isoform 1 [Homo sapiens] |
| gi|155969680|ref|NP_0 | 10.5 | 10.5 | 10.5 | thymidine kinase 1, soluble [Homo sapiens] |
| gi|5031753|ref|NP_005 | 10.5 | 10.5 | 10.5 | heterogeneous nuclear ribonucleoprotein H1 [Homo sapiens] |
| gi|20127556|ref|NP_05 | 6.8 | 10.4 | 10.4 | G-2 and S-phase expressed 1 [Homo sapiens] |
| gi|40018640|ref|NP_07 | 7.5 | 10.4 | 10.4 | parafibromin [Homo sapiens] |
| gi|40254978|ref|NP_11 | 7.4 | 10.3 | 10.3 | FIP1-like 1 [Homo sapiens] |
| gi|20070125|ref|NP_00 | 7.7 | 10.2 | 10.2 | prolyl 4-hydroxylase, beta subunit precursor [Homo sapiens] |
| gi|4503193|ref|NP_001 | 10.1 | 10.1 | 10.1 | general transcription factor IIB [Homo sapiens] |
| gi|29171753|ref|NP_80 | 8 | 10 | 10 | PTPRF interacting protein alpha 1 isoform a [Homo sapiens] |
| gi|88976655|ref|XP_93 | 10 | 10 | 10 | PREDICTED: hypothetical protein [Homo sapiens] |
| gi|58761486|ref|NP_00 | 7.9 | 9.9 | 9.9 | chaperonin containing TCP1, subunit 3 isoform b [Homo sapiens] |
| gi|113418061|ref|XP_9 | 9.7 | 9.7 | 9.7 | PREDICTED: similar to ribosomal protein L12 [Homo sapiens] |
| gi|14210536|ref|NP_11 | 9.6 | 9.6 | 9.6 | tubulin, beta 6 [Homo sapiens] |
| gi|4885073|ref|NP_005 | 9.6 | 9.6 | 9.6 | activating transcription factor 1 [Homo sapiens] |
| gi|7669492|ref|NP_002 | 9.6 | 9.6 | 9.6 | glyceraldehyde-3-phosphate dehydrogenase [Homo sapiens] |
| gi|4757880|ref|NP_004 | 9.5 | 9.5 | 9.5 | BUB3 budding uninhibited by benzimidazoles 3 isoform a [Homo sapiens] |
| gi|5032159|ref|NP_005 | 9.4 | 9.4 | 9.4 | transducin beta-like 1X [Homo sapiens] |
| gi|153792590|ref|NP_0 | 9.3 | 9.3 | 9.3 | heat shock protein 90kDa alpha (cytosolic), class A member 1 isoform 1 [Homo sapiens] |
| gi|38201714|ref|NP_00 | 9.2 | 9.2 | 9.2 | ELAV-like 1 [Homo sapiens] |
| gi|62632765|ref|NP_00 | 9.2 | 9.2 | 9.2 | N-methylpurine-DNA glycosylase isoform b [Homo sapiens] |
| gi|24308207|ref|NP_06 | 5.5 | 9.1 | 9.1 | leucine rich repeat containing 47 [Homo sapiens] |
| gi|46447823|ref|NP_11 | 9.1 | 9.1 | 9.1 | nuclear factor of activated T-cells, cytoplasmic, calcineurin-dependent 2 interacting protein [Homo sapiens] |

FIG. 25 (Cont.)

| ID | Val1 | Val2 | Val3 | Description |
|---|---|---|---|---|
| gi|55749531|ref|NP_00 | 9.1 | 9.1 | 9.1 | splicing factor 3B subunit 2 [Homo sapiens] |
| gi|4503659|ref|NP_001 | | 9 | 9 | ubiquitin-like protein fubi and ribosomal protein S30 precursor [Homo sapiens] |
| gi|56676330|ref|NP_05 | 6.7 | 9 | 9 | HP1-BP74 [Homo sapiens] |
| gi|32454741|ref|NP_00 | 8.9 | 8.9 | 8.9 | serine (or cysteine) proteinase inhibitor, clade H, member 1 precursor [Homo sapiens] |
| gi|40807450|ref|NP_95 | 8.9 | 8.9 | 8.9 | papillary renal cell carcinoma translocation-associated gene product isoform 2 [Homo sapiens] |
| gi|16256458|ref|NP_6 | 8.6 | 8.6 | 8.6 | hypothetical protein LOC121053 [Homo sapiens] |
| gi|4506583|ref|NP_002 | 8.6 | 8.6 | 8.6 | replication protein A1, 70kDa [Homo sapiens] |
| gi|53759148|ref|NP_00 | 8.6 | 8.6 | 8.6 | retinoblastoma binding protein 5 [Homo sapiens] |
| gi|4885193|ref|NP_005 | 6.7 | 8.4 | 8.4 | AT rich interactive domain 3A (BRIGHT- like) protein [Homo sapiens] |
| gi|50659095|ref|NP_00 | 8.4 | 8.4 | 8.4 | DEAD (Asp-Glu-Ala-Asp) box polypeptide 21 [Homo sapiens] |
| gi|5803013|ref|NP_006 | 8.4 | 8.4 | 8.4 | endoplasmic reticulum protein 29 isoform 1 precursor [Homo sapiens] |
| gi|7705369|ref|NP_057 | 8.4 | 8.4 | 8.4 | coatomer protein complex, subunit beta [Homo sapiens] |
| gi|14836864|ref|NP_0 | 5.1 | 8.3 | 8.3 | SWI/SNF-related matrix-associated actin-dependent regulator of chromatin d2 isoform 1 [Homo sapiens] |
| gi|20149594|ref|NP_63 | 8.1 | 8.3 | 8.3 | heat shock 90kDa protein 1, beta [Homo sapiens] |
| gi|4507521|ref|NP_001 | 7.1 | 8.3 | 8.3 | transketolase [Homo sapiens] |
| gi|7657015|ref|NP_055 | 8.3 | 8.3 | 8.3 | hypothetical protein LOC51493 [Homo sapiens] |
| gi|54355000|ref|NP_0 | 8.2 | 8.2 | 8.2 | KH-type splicing regulatory protein (FUSE binding protein 2) [Homo sapiens] |
| gi|4758356|ref|NP_004 | 8.2 | 8.2 | 8.2 | flap structure-specific endonuclease 1 [Homo sapiens] |
| gi|56788366|ref|NP_00 | 8.1 | 8.1 | 8.1 | phosphatidylinositol-binding clathrin assembly protein isoform 1 [Homo sapiens] |
| gi|57222565|ref|NP_00 | 8.1 | 8.1 | 8.1 | protein phosphatase 2, catalytic subunit, beta isoform [Homo sapiens] |
| gi|11252260|ref|NP_00 | 6.8 | 8 | 8 | DNA topoisomerase I [Homo sapiens] |
| gi|19913371|ref|NP_07 | 8 | 8 | 8 | nuclear receptor co-repressor/HDAC3 complex subunit [Homo sapiens] |
| gi|14327896|ref|NP_11 | 7.9 | 7.9 | 7.9 | cyclin B1 [Homo sapiens] |
| gi|30795212|ref|NP_00 | 5 | 7.9 | 7.9 | insulin-like growth factor 2 mRNA binding protein 3 [Homo sapiens] |
| gi|44868822|ref|NP_05 | 6.6 | 7.9 | 7.9 | hypothetical protein LOC23248 [Homo sapiens] |
| gi|19924131|ref|NP_59 | 5.7 | 7.8 | 7.8 | RAD50 homolog isoform 2 [Homo sapiens] |
| gi|27363484|ref|NP_75 | 7.8 | 7.8 | 7.8 | E74-like factor 1 (ets domain transcription factor) [Homo sapiens] |
| gi|21361322|ref|NP_00 | 7.7 | 7.7 | 7.7 | tubulin, beta 4 [Homo sapiens] |
| gi|5453603|ref|NP_006 | 7.7 | 7.7 | 7.7 | chaperonin containing TCP1, subunit 2 [Homo sapiens] |
| gi|41393573|ref|NP_05 | 7.6 | 7.6 | 7.6 | G protein-coupled receptor kinase interactor 1 isoform 2 [Homo sapiens] |
| gi|16920395|ref|XP_0 | 7.5 | 7.5 | 7.5 | PREDICTED: hypothetical protein [Homo sapiens] |
| gi|56549119|ref|NP_00 | 7.5 | 7.5 | 7.5 | dynamin 2 isoform 3 [Homo sapiens] |
| gi|15503018|ref|NP_0 | 3.5 | 7.4 | 7.4 | hypothetical protein LOC55726 [Homo sapiens] |
| gi|17921989|ref|NP_00 | 6.7 | 7.4 | 7.4 | tubulin, alpha 4a [Homo sapiens] |
| gi|25121987|ref|NP_05 | 4.2 | 7.4 | 7.4 | non-SMC condensin I complex, subunit H [Homo sapiens] |
| gi|6005942|ref|NP_009 | 5.6 | 7.4 | 7.4 | valosin-containing protein [Homo sapiens] |
| gi|14853685|ref|NP_0 | 5.8 | 7.3 | 7.3 | coatomer protein complex, subunit alpha isoform 1 [Homo sapiens] |
| gi|2443015|ref|NP_00 | 7.3 | 7.3 | 7.3 | proteasome 26S ATPase subunit 1 [Homo sapiens] |
| gi|4503483|ref|NP_001 | 6.4 | 7.3 | 7.3 | eukaryotic translation elongation factor 2 [Homo sapiens] |
| gi|57863301|ref|NP_05 | 5.1 | 7.2 | 7.2 | CLIP-associating protein 2 [Homo sapiens] |
| gi|21264355|ref|NP_00 | 7.1 | 7.1 | 7.1 | SWI/SNF-related matrix-associated actin-dependent regulator of chromatin e1 [Homo sapiens] |
| gi|31543983|ref|NP_11 | 7.1 | 7.1 | 7.1 | ADP-ribosylation factor GTPase activating protein 2 [Homo sapiens] |
| gi|38569466|ref|NP_00 | 4.9 | 7.1 | 7.1 | ROD1 regulator of differentiation 1 [Homo sapiens] |
| gi|52632383|ref|NP_00 | 7.1 | 7.1 | 7.1 | heterogeneous nuclear ribonucleoprotein L isoform a [Homo sapiens] |
| gi|6005757|ref|NP_009 | 7 | 7 | 7 | chromatin-specific transcription elongation factor large subunit [Homo sapiens] |
| gi|7549809|ref|NP_005 | 2.2 | 7 | 7 | plastin 3 [Homo sapiens] |
| gi|14141170|ref|NP_00 | 6.9 | 6.9 | 6.9 | metastasis-associated protein 2 [Homo sapiens] |
| gi|15011974|ref|NP_00 | 5.6 | 6.9 | 6.9 | rho/rac guanine nucleotide exchange factor 2 [Homo sapiens] |
| gi|16916230|ref|XP_0 | 6.9 | 6.9 | 6.9 | PREDICTED: similar to hCG2040301 [Homo sapiens] |
| gi|47519675|ref|NP_11 | 5.7 | 6.9 | 6.9 | microtubule-associated protein 2 isoform 2 [Homo sapiens] |
| gi|4758304|ref|NP_004 | 6.8 | 6.8 | 6.8 | protein disulfide isomerase-associated 4 [Homo sapiens] |
| gi|10347200|ref|NP_0 | 5.6 | 6.7 | 6.7 | antigen identified by monoclonal antibody Ki-67 [Homo sapiens] |
| gi|21493031|ref|NP_65 | 5 | 6.6 | 6.6 | A-kinase anchor protein 13 isoform 3 [Homo sapiens] |
| gi|4505101|ref|NP_003 | 6.5 | 6.5 | 6.5 | microtubule-associated protein 7 [Homo sapiens] |
| gi|4505917|ref|NP_002 | 3.3 | 6.5 | 6.5 | exosome component 10 isoform 2 [Homo sapiens] |
| gi|21914927|ref|NP_06 | 4.7 | 6.4 | 6.4 | helicase, lymphoid-specific [Homo sapiens] |
| gi|4759046|ref|NP_004 | 6.4 | 6.4 | 6.4 | RNA polymerase I subunit isoform 2 [Homo sapiens] |
| gi|11939571|ref|NP_0 | 6.3 | 6.3 | 6.3 | forkhead box C1 [Homo sapiens] |
| gi|13390863|ref|NP_6 | 6.3 | 6.3 | 6.3 | SWI/SNF-related matrix-associated actin-dependent regulator of chromatin d1 isoform b [Homo sapiens] |
| gi|24308179|ref|NP_06 | 6.3 | 6.3 | 6.3 | CTTNBP2 N-terminal like [Homo sapiens] |
| gi|38372909|ref|NP_05 | 6.3 | 6.3 | 6.3 | jumonji domain containing 1B [Homo sapiens] |
| gi|17190192|ref|NP_0 | 5.2 | 6.2 | 6.2 | heterogeneous nuclear ribonucleoprotein C isoform a [Homo sapiens] |
| gi|17978466|ref|NP_00 | 6.2 | 6.2 | 6.2 | cyclin T1 [Homo sapiens] |
| gi|21735596|ref|NP_05 | 6.2 | 6.2 | 6.2 | programmed cell death 4 isoform 1 [Homo sapiens] |
| gi|4505317|ref|NP_002 | 2.9 | 6.2 | 6.2 | protein phosphatase 1, regulatory (inhibitor) subunit 12A [Homo sapiens] |
| gi|19743813|ref|NP_00 | 6.1 | 6.1 | 6.1 | integrin beta 1 isoform 1A precursor [Homo sapiens] |
| gi|24234753|ref|NP_00 | 1.6 | 6.1 | 6.1 | interleukin enhancer binding factor 3 isoform b [Homo sapiens] |
| gi|4502027|ref|NP_000 | 6.1 | 6.1 | 6.1 | albumin precursor [Homo sapiens] |
| gi|15475925|ref|NP_0 | 4.7 | 6 | 6 | spectrin, alpha, non-erythrocytic 1 (alpha-fodrin) [Homo sapiens] |
| gi|40254861|ref|NP_05 | 6 | 6 | 6 | ubiquitin associated protein 2-like [Homo sapiens] |
| gi|55770844|ref|NP_00 | 3.5 | 6 | 6 | catenin, alpha 1 [Homo sapiens] |
| gi|77404397|ref|NP_05 | 5.3 | 6 | 6 | staphylococcal nuclease domain containing 1 [Homo sapiens] |
| gi|21218438|ref|NP_06 | 5.9 | 5.9 | 5.9 | GATA zinc finger domain containing 2B [Homo sapiens] |
| gi|5453629|ref|NP_006 | 5.9 | 5.9 | 5.9 | dynactin 2 [Homo sapiens] |
| gi|10431354|ref|NP_0 | 5.8 | 5.8 | 5.8 | transducer of regulated CREB protein 3 isoform a [Homo sapiens] |
| gi|10566636|ref|NP_2 | 5.1 | 5.8 | 5.8 | tankyrase 1-binding protein 1 [Homo sapiens] |
| gi|7662274|ref|NP_055 | 5.8 | 5.8 | 5.8 | epidermal Langerhans cell protein LCP1 [Homo sapiens] |
| gi|14538656|ref|NP_0 | 5.7 | 5.7 | 5.7 | zinc finger protein 148 [Homo sapiens] |

FIG. 25 (Cont.)

| ID | | Val1 | | Val2 | Val3 | Description |
|---|---|---|---|---|---|---|
| gi|22538461|ref|NP_00 | | 4.6 | | 5.7 | 5.7 | nuclear receptor co-repressor 1 [Homo sapiens] |
| gi|35493811|ref|NP_90 | | 5.7 | | 5.7 | 5.7 | RNA binding motif protein 39 isoform a [Homo sapiens] |
| gi|112807226|ref|NP_0 | | 3.7 | | 5.6 | 5.6 | hypothetical protein LOC91748 [Homo sapiens] |
| gi|34251212|ref|NP_00 | | 5.6 | | 5.6 | 5.6 | DEAD (Asp-Glu-Ala-Asp) box polypeptide 20 [Homo sapiens] |
| gi|124028529|ref|NP_0 | | 3.3 | | 5.5 | 5.5 | symplekin [Homo sapiens] |
| gi|42734503|ref|NP_97 | | 5.5 | | 5.5 | 5.5 | membrane component chromosome 11 surface marker 1 isoform 2 [Homo sapiens] |
| gi|38044290|ref|NP_06 | | 5.4 | | 5.4 | 5.4 | zinc finger, CCHC domain containing 8 [Homo sapiens] |
| gi|50658063|ref|NP_00 | | 4.3 | | 5.4 | 5.4 | SMC4 structural maintenance of chromosomes 4-like 1 [Homo sapiens] |
| gi|57164942|ref|NP_00 | | 5.4 | | 5.4 | 5.4 | colonic and hepatic tumor over-expressed protein isoform a [Homo sapiens] |
| gi|12025678|ref|NP_00 | | 5.3 | | 5.3 | 5.3 | actinin, alpha 4 [Homo sapiens] |
| gi|21237802|ref|NP_00 | | 5.3 | | 5.3 | 5.3 | SWI/SNF-related matrix-associated actin-dependent regulator of chromatin c1 [Homo sapiens] |
| gi|42476169|ref|NP_06 | | 5.3 | | 5.3 | 5.3 | Paf1, RNA polymerase II associated factor, homolog [Homo sapiens] |
| gi|45034811|ref|NP_001 | | 5.3 | | 5.3 | 5.3 | eukaryotic translation elongation factor 1 gamma [Homo sapiens] |
| gi|10448546|ref|NP_6 | | 5.2 | | 5.2 | 5.2 | TBP-associated factor 8 [Homo sapiens] |
| gi|18378731|ref|NP_06 | | 3.4 | | 5.2 | 5.2 | HMG-BOX transcription factor BBX [Homo sapiens] |
| gi|4582777|ref|NP_05 | | 3.8 | | 5.2 | 5.2 | autoantigen RCD8 [Homo sapiens] |
| gi|115529449|ref|NP_0 | | 5.1 | | 5.1 | 5.1 | upstream binding transcription factor, RNA polymerase I isoform b [Homo sapiens] |
| gi|116256445|ref|NP_0 | | 5.1 | | 5.1 | 5.1 | nuclear receptor co-repressor 2 isoform 2 [Homo sapiens] |
| gi|124494254|ref|NP_0 | | 5.1 | | 5.1 | 5.1 | ErbB3-binding protein 1 [Homo sapiens] |
| gi|6754472|ref|NP_004 | | 5.1 | | 5.1 | 5.1 | kinesin family member 23 isoform 2 [Homo sapiens] |
| gi|6912246|ref|NP_036 | | 5.1 | | 5.1 | 5.1 | CD3E antigen, epsilon polypeptide associated protein [Homo sapiens] |
| gi|14958928|ref|NP_0 | | 5 | | 5 | 5 | SLAIN motif family, member 2 [Homo sapiens] |
| gi|19923142|ref|NP_00 | | 3.4 | | 5 | 5 | karyopherin beta 1 [Homo sapiens] |
| gi|34101288|ref|NP_05 | | 5 | | 5 | 5 | cleavage and polyadenylation specific factor 2 [Homo sapiens] |
| gi|169170622|ref|XP_0 | | 4.9 | | 4.9 | 4.9 | PREDICTED: hypothetical protein [Homo sapiens] |
| gi|31742536|ref|NP_07 | | 4.9 | | 4.9 | 4.9 | fidgetin-like 1 [Homo sapiens] |
| gi|45035399|ref|NP_001 | | 4.9 | | 4.9 | 4.9 | eukaryotic translation initiation factor 4 gamma, 2 isoform 1 [Homo sapiens] |
| gi|13514809|ref|NP_00 | | 4.8 | | 4.8 | 4.8 | DEAD (Asp-Glu-Ala-Asp) box polypeptide 3, Y-linked [Homo sapiens] |
| gi|25470890|ref|NP_73 | | 4.8 | | 4.8 | 4.8 | DAZ associated protein 1 isoform a [Homo sapiens] |
| gi|13375809|ref|NP_07 | | 4.7 | | 4.7 | 4.7 | RNA polymerase II associated protein 3 [Homo sapiens] |
| gi|27501458|ref|NP_07 | | 4.7 | | 4.7 | 4.7 | CTF18, chromosome transmission fidelity factor 18 homolog [Homo sapiens] |
| gi|28559039|ref|NP_00 | | 4.6 | | 4.7 | 4.7 | mediator complex subunit 1 [Homo sapiens] |
| gi|5032027|ref|NP_005 | | 4.7 | | 4.7 | 4.7 | retinoblastoma binding protein 4 [Homo sapiens] |
| gi|6453818|ref|NP_015 | | 4.7 | | 4.7 | 4.7 | kinesin family member 22 [Homo sapiens] |
| gi|63003907|ref|NP_00 | | 4.5 | | 4.5 | 4.5 | protein phosphatase 1, regulatory (inhibitor) subunit 13 like [Homo sapiens] |
| gi|112382250|ref|NP_0 | | 4.4 | | 4.4 | 4.4 | spectrin, beta, non-erythrocytic 1 isoform 1 [Homo sapiens] |
| gi|5453607|ref|NP_006 | | 4.4 | | 4.4 | 4.4 | chaperonin containing TCP1, subunit 7 isoform a [Homo sapiens] |
| gi|58530842|ref|NP_00 | | 4.4 | | 4.4 | 4.4 | desmoplakin isoform II [Homo sapiens] |
| gi|7705284|ref|NP_057 | | 4.4 | | 4.4 | 4.4 | anaphase-promoting complex subunit 7 [Homo sapiens] |
| gi|56676335|ref|NP_06 | | 4.3 | | 4.3 | 4.3 | RAP1 interacting factor 1 [Homo sapiens] |
| gi|84043963|ref|NP_05 | | 4.3 | | 4.3 | 4.3 | eukaryotic translation initiation factor 5B [Homo sapiens] |
| gi|18426904|ref|NP_56 | | 4.2 | | 4.2 | 4.2 | Werner helicase interacting protein isoform 1 [Homo sapiens] |
| gi|4758958|ref|NP_004 | | 4.2 | | 4.2 | 4.2 | cAMP-dependent protein kinase, regulatory subunit alpha 2 [Homo sapiens] |
| gi|6317661|ref|NP_67 | | 2.4 | | 4.2 | 4.2 | modulator of estrogen induced transcription isoform a [Homo sapiens] |
| gi|13129006|ref|NP_07 | | 4.1 | | 4.1 | 4.1 | nucleolar protein GU2 [Homo sapiens] |
| gi|31563537|ref|NP_05 | | 4.1 | | 4.1 | 4.1 | CLIP-associating protein 1 [Homo sapiens] |
| gi|4758556|ref|NP_004 | | 4.1 | | 4.1 | 4.1 | PRP3 pre-mRNA processing factor 3 homolog [Homo sapiens] |
| gi|50321791|ref|NP_005 | | 4.1 | | 4.1 | 4.1 | tripartite motif-containing 28 protein [Homo sapiens] |
| gi|31581524|ref|NP_65 | | 2.9 | | 4 | 4 | cordon-bleu homolog [Homo sapiens] |
| gi|5453660|ref|NP_006 | | 4 | | 4 | 4 | tubulin, gamma complex associated protein 3 [Homo sapiens] |
| gi|13123772|ref|NP_05 | | 3.9 | | 3.9 | 3.9 | CCR4-NOT transcription complex, subunit 10 [Homo sapiens] |
| gi|22027538|ref|NP_03 | | 3.8 | | 3.9 | 3.9 | programmed cell death 6 interacting protein [Homo sapiens] |
| gi|62241042|ref|NP_00 | | 3 | | 3.9 | 3.9 | glutamyl-prolyl tRNA synthetase [Homo sapiens] |
| gi|68509926|ref|NP_00 | | 3.9 | | 3.9 | 3.9 | DEAH (Asp-Glu-Ala-His) box polypeptide 15 [Homo sapiens] |
| gi|10863889|ref|NP_00 | | 3.8 | | 3.8 | 3.8 | squamous cell carcinoma antigen recognized by T cells 1 [Homo sapiens] |
| gi|12789562|ref|NP_0 | | 3.8 | | 3.8 | 3.8 | interferon, gamma-inducible protein 16 [Homo sapiens] |
| gi|21237805|ref|NP_00 | | 3.8 | | 3.8 | 3.8 | SWI/SNF-related matrix-associated actin-dependent regulator of chromatin c2 isoform a [Homo sapiens] |
| gi|21361625|ref|NP_06 | | 3.8 | | 3.8 | 3.8 | Sec5 protein [Homo sapiens] |
| gi|148277037|ref|NP_0 | | 3.7 | | 3.7 | 3.7 | AP2 associated kinase 1 [Homo sapiens] |
| gi|4505895|ref|NP_002 | | 3.7 | | 3.7 | 3.7 | pleiotropic regulator 1 (PRL1 homolog, Arabidopsis) [Homo sapiens] |
| gi|45446747|ref|NP_98 | | 3.7 | | 3.7 | 3.7 | DEAD box polypeptide 42 protein [Homo sapiens] |
| gi|46852388|ref|NP_06 | | 2.3 | | 3.7 | 3.7 | cell-cycle and apoptosis regulatory protein 1 [Homo sapiens] |
| gi|4758012|ref|NP_004 | | 3.7 | | 3.7 | 3.7 | clathrin heavy chain 1 [Homo sapiens] |
| gi|5031839|ref|NP_005 | | 3.7 | | 3.7 | 3.7 | keratin 6A [Homo sapiens]; keratin 6A; keratin, epidermal type II, K6A; cytokeratin 6A; 56 cytoskeletal type II keratin [Homo sapiens] |
| gi|11067749|ref|NP_03 | | 3.6 | | 3.6 | 3.6 | bromodomain containing protein 3 [Homo sapiens] |
| gi|157671927|ref|NP_6 | | 3.6 | | 3.6 | 3.6 | spermatogenesis associated 5 [Homo sapiens] |
| gi|41281612|ref|NP_11 | | 3.6 | | 3.6 | 3.6 | hypothetical protein LOC283489 [Homo sapiens] |
| gi|45047315|ref|NP_003 | | 3.6 | | 3.6 | 3.6 | poly A binding protein, cytoplasmic 4 [Homo sapiens] |
| gi|45356151|ref|NP_05 | | 3.6 | | 3.6 | 3.6 | non-SMC condensin II complex, subunit D3 [Homo sapiens] |
| gi|5174735|ref|NP_006 | | 3.6 | | 3.6 | 3.6 | tubulin, beta, 2 [Homo sapiens] |
| gi|14915869|ref|NP_5 | | 3.5 | | 3.5 | 3.5 | HLA-B associated transcript-2 [Homo sapiens] |
| gi|114326455|ref|NP_0 | | 3.4 | | 3.4 | 3.4 | chromodomain helicase DNA binding protein 8 [Homo sapiens] |
| gi|27477136|ref|NP_06 | | 3.4 | | 3.4 | 3.4 | zinc finger antiviral protein isoform 1 [Homo sapiens] |
| gi|57761546|ref|NP_05 | | 3.4 | | 3.4 | 3.4 | amine oxidase (flavin containing) domain 2 isoform b [Homo sapiens] |
| gi|169168349|ref|XP_0 | | 3.3 | | 3.3 | 3.3 | PREDICTED: similar to RNA-binding protein 27 (RNA-binding motif protein 27) [Homo sapiens] |
| gi|18105007|ref|NP_00 | | 1.4 | | 3.3 | 3.3 | carbamoylphosphate synthetase 2/aspartate transcarbamylase/dihydroorotase [Homo sapiens] |
| gi|18860916|ref|NP_03 | | 3.3 | | 3.3 | 3.3 | 5'-3' exoribonuclease 2 [Homo sapiens] |
| gi|21264369|ref|NP_62 | | 3.3 | | 3.3 | 3.3 | nucleoporin 98kD isoform 2 [Homo sapiens] |
| gi|42518070|ref|NP_00 | | 2.3 | | 3.3 | 3.3 | tight junction protein 2 (zona occludens 2) isoform 1 [Homo sapiens] |

FIG. 25 (Cont.)

| ID | | | | Description |
|---|---|---|---|---|
| gi\|56549696\|ref\|NP_05 | 3.3 | | 3.3 | 3.3 | E1A binding protein p400 [Homo sapiens] |
| gi\|87196351\|ref\|NP_00 | 2.1 | | 3.3 | 3.3 | DEAD/H (Asp-Glu-Ala-Asp/His) box polypeptide 3 [Homo sapiens] |
| gi\|7657381\|ref\|NP_055 | 3.2 | | 3.2 | 3.2 | PRP19/PSO4 pre-mRNA processing factor 19 homolog [Homo sapiens] |
| gi\|7662230\|ref\|NP_055 | 3.2 | | 3.2 | 3.2 | ring finger protein 40 [Homo sapiens] |
| gi\|110227615\|ref\|NP_6 | 3.1 | | 3.1 | 3.1 | echinoderm microtubule associated protein like 3 [Homo sapiens] |
| gi\|13491166\|ref\|NP_05 | 3.1 | | 3.1 | 3.1 | pumilio 1 isoform 2 [Homo sapiens] |
| gi\|42716275\|ref\|NP_05 | 2.6 | | 3.1 | 3.1 | CCR4-NOT transcription complex, subunit 1 isoform a [Homo sapiens] |
| gi\|4501891\|ref\|NP_001 | 3.1 | | 3.1 | 3.1 | actinin, alpha 1 [Homo sapiens] |
| gi\|4505913\|ref\|NP_000 | 3.1 | | 3.1 | 3.1 | PMS2 postmeiotic segregation increased 2 isoform a [Homo sapiens] |
| gi\|51599156\|ref\|NP_00 | 3 | | 3 | 3 | chromodomain helicase DNA binding protein 4 [Homo sapiens] |
| gi\|63054866\|ref\|NP_06 | 3 | | 3 | 3 | leucine rich repeat containing 16 [Homo sapiens] |
| gi\|7657013\|ref\|NP_036 | 3 | | 3 | 3 | apoptosis antagonizing transcription factor [Homo sapiens] |
| gi\|89276756\|ref\|NP_00 | 3 | | 3 | 3 | serine/threonine-protein kinase PRP4K [Homo sapiens] |
| gi\|149904340\|ref\|NP_0 | 2.9 | | 2.9 | 2.9 | WD repeat domain 82 [Homo sapiens] |
| gi\|44771201\|ref\|NP_08 | 2.9 | | 2.9 | 2.9 | integrator complex subunit 5 [Homo sapiens] |
| gi\|7305053\|ref\|NP_038 | 1.6 | | 2.9 | 2.9 | myoferlin isoform a [Homo sapiens] |
| gi\|113413150\|ref\|XP_0 | 1.6 | | 2.8 | 2.8 | PREDICTED: hypothetical protein isoform 6 [Homo sapiens] |
| gi\|22325364\|ref\|NP_06 | 2.8 | | 2.8 | 2.8 | ubiquitin associated protein 2 [Homo sapiens] |
| gi\|37620163\|ref\|NP_06 | 2.6 | | 2.7 | 2.7 | ANKHD1-EIF4EBP3 protein [Homo sapiens] |
| gi\|39725938\|ref\|NP_00 | 2.7 | | 2.7 | 2.7 | polymerase (RNA) III (DNA directed) polypeptide A, 155kDa [Homo sapiens] |
| gi\|4505939\|ref\|NP_000 | 2.7 | | 2.7 | 2.7 | DNA directed RNA polymerase II polypeptide A [Homo sapiens] |
| gi\|4557719\|ref\|NP_000 | 2.7 | | 2.7 | 2.7 | DNA ligase I [Homo sapiens] |
| gi\|57863257\|ref\|NP_11 | 2.7 | | 2.7 | 2.7 | T-complex protein 1 isoform a [Homo sapiens] |
| gi\|59814247\|ref\|NP_00 | 2.7 | | 2.7 | 2.7 | BUB1 budding uninhibited by benzimidazoles 1 homolog beta [Homo sapiens] |
| gi\|132626688\|ref\|NP_0 | 2.6 | | 2.6 | 2.6 | mediator of DNA damage checkpoint 1 [Homo sapiens] |
| gi\|157817073\|ref\|NP_0 | 2.1 | | 2.6 | 2.6 | Cdc2-related kinase, arginine/serine-rich isoform 2 [Homo sapiens] |
| gi\|16753233\|ref\|NP_00 | 2.6 | | 2.6 | 2.6 | talin 1 [Homo sapiens] |
| gi\|21264575\|ref\|NP_62 | 1.6 | | 2.6 | 2.6 | AT rich interactive domain 1A isoform b [Homo sapiens] |
| gi\|33620755\|ref\|NP_06 | 2.6 | | 2.6 | 2.6 | YEATS domain containing 2 [Homo sapiens] |
| gi\|50053795\|ref\|NP_00 | 2.6 | | 2.6 | 2.6 | eukaryotic translation initiation factor 4B [Homo sapiens] |
| gi\|56556086\|ref\|NP_00 | 2.6 | | 2.6 | 2.6 | WD repeat and HMG-box DNA binding protein 1 isoform 2 [Homo sapiens] |
| gi\|71044477\|ref\|NP_54 | 2.6 | | 2.6 | 2.6 | death inducer-obliterator 1 isoform b [Homo sapiens] |
| gi\|38202257\|ref\|NP_93 | 2.5 | | 2.5 | 2.5 | alpha glucosidase II alpha subunit isoform 2 [Homo sapiens] |
| gi\|116734694\|ref\|NP_0 | 2.4 | | 2.4 | 2.4 | RNA binding motif protein 23 isoform 2 [Homo sapiens] |
| gi\|4506787\|ref\|NP_003 | 1.8 | | 2.4 | 2.4 | IQ motif containing GTPase activating protein 1 [Homo sapiens] |
| gi\|55741557\|ref\|NP_05 | 2.4 | | 2.4 | 2.4 | mitogen-activated protein kinase binding protein 1 [Homo sapiens] |
| gi\|57164405\|ref\|NP_20 | 1.5 | | 2.4 | 2.4 | tetratricopeptide repeat, ankyrin repeat and coiled-coil containing 1 [Homo sapiens] |
| gi\|47933339\|ref\|NP_07 | 2.3 | | 2.3 | 2.3 | RNA binding motif protein 15 [Homo sapiens] |
| gi\|10225351\|ref\|NP_0 | 2.2 | | 2.2 | 2.2 | diaphanous homolog 3 isoform a [Homo sapiens] |
| gi\|14155142\|ref\|NP_0 | 2.2 | | 2.2 | 2.2 | nuclear pore complex-associated protein TPR [Homo sapiens] |
| gi\|120587019\|ref\|NP_0 | 2.2 | | 2.2 | 2.2 | zinc finger protein 318 [Homo sapiens] |
| gi\|24308005\|ref\|NP_05 | 2.2 | | 2.2 | 2.2 | Paf1/RNA polymerase II complex component [Homo sapiens] |
| gi\|40217847\|ref\|NP_05 | 1.5 | | 2.2 | 2.2 | activating signal cointegrator 1 complex subunit 3-like 1 [Homo sapiens] |
| gi\|50409903\|ref\|NP_06 | 2.2 | | 2.2 | 2.2 | aftiphilin protein isoform b [Homo sapiens] |
| gi\|150418007\|ref\|NP_0 | 1.9 | | 2.1 | 2.1 | RAN binding protein 2 [Homo sapiens] |
| gi\|41281521\|ref\|NP_05 | 2.1 | | 2.1 | 2.1 | non-SMC condensin I complex, subunit D2 [Homo sapiens] |
| gi\|18572613\|ref\|NP_0 | 2 | | 2 | 2 | splicing coactivator subunit SRm300 [Homo sapiens] |
| gi\|61676188\|ref\|NP_11 | 2 | | 2 | 2 | HECT, UBA and WWE domain containing 1 [Homo sapiens] |
| gi\|62955803\|ref\|NP_05 | 2 | | 2 | 2 | nucleoporin 188kDa [Homo sapiens] |
| gi\|15147337\|ref\|NP_05 | 0.9 | | 1.9 | 1.9 | ubiquitin protein ligase E3 component n-recognin 5 [Homo sapiens] |
| gi\|21361331\|ref\|NP_00 | 1.9 | | 1.9 | 1.9 | carbamoyl-phosphate synthetase 1, mitochondrial [Homo sapiens] |
| gi\|33350932\|ref\|NP_00 | 1.9 | | 1.9 | 1.9 | dynein, cytoplasmic, heavy polypeptide 1 [Homo sapiens] |
| gi\|105996514\|ref\|NP_0 | 1.8 | | 1.8 | 1.8 | filamin B, beta (actin binding protein 278) [Homo sapiens] |
| gi\|103471997\|ref\|NP_0 | 1.7 | | 1.7 | 1.7 | polymerase (RNA) I polypeptide A, 194kDa [Homo sapiens] |
| gi\|149192855\|ref\|NP_0 | 1.7 | | 1.7 | 1.7 | hypothetical protein LOC84726 [Homo sapiens] |
| gi\|33946327\|ref\|NP_00 | 1.7 | | 1.7 | 1.7 | nucleoporin 214kDa [Homo sapiens] |
| gi\|10347429\|ref\|NP_0 | 1.6 | | 1.6 | 1.6 | mediator of RNA polymerase II transcription, subunit 12 homolog [Homo sapiens] |
| gi\|124378039\|ref\|NP_0 | 1.6 | | 1.6 | 1.6 | SEC16 homolog A [Homo sapiens] |
| gi\|21071056\|ref\|NP_00 | 1.6 | | 1.6 | 1.6 | SWI/SNF-related matrix-associated actin-dependent regulator of chromatin a4 [Homo sapiens] |
| gi\|7662018\|ref\|NP_055 | 1.6 | | 1.6 | 1.6 | PHD finger protein 3 [Homo sapiens] |
| gi\|21264365\|ref\|NP_05 | 1.5 | | 1.5 | 1.5 | nucleoporin 98kD isoform 1 [Homo sapiens] |
| gi\|54112403\|ref\|NP_06 | 1.5 | | 1.5 | 1.5 | chromodomain helicase DNA binding protein 7 [Homo sapiens] |
| gi\|71044479\|ref\|NP_14 | 1.5 | | 1.5 | 1.5 | death inducer-obliterator 1 isoform c [Homo sapiens] |
| gi\|156766050\|ref\|NP_6 | 1.1 | | 1.4 | 1.4 | AHNAK nucleoprotein 2 [Homo sapiens] |
| gi\|21493029\|ref\|NP_00 | 1.4 | | 1.4 | 1.4 | A-kinase anchor protein 13 isoform 2 [Homo sapiens] |
| gi\|112382252\|ref\|NP_8 | 1.2 | | 1.2 | 1.2 | spectrin, beta, non-erythrocytic 1 isoform 2 [Homo sapiens] |
| gi\|56550039\|ref\|NP_00 | 0.9 | | 0.9 | 0.9 | myeloid/lymphoid or mixed-lineage leukemia (trithorax homolog, Drosophila) [Homo sapiens] |
| gi\|126116565\|ref\|NP_0 | 0.7 | | 0.7 | 0.7 | MYC binding protein 2 [Homo sapiens] |
| gi\|30794372\|ref\|NP_06 | 0.6 | | 0.6 | 0.6 | polybromo 1 isoform 1 [Homo sapiens] |
| gi\|169164207\|ref\|XP_0 | 0.4 | | 0.4 | 0.4 | PREDICTED: hypothetical protein [Homo sapiens] |

FIG. 26

| Locus | Normal | | Loose' | | Total | Description |
|---|---|---|---|---|---|---|
| | Wild Type 200mM | Mutant 200mM | Wild Type 200mM | Mutant 200mM | | |
| gi\|3079523\|ref\|NP_00 | 28.2 | | 28.2 | | 28.2 | brain abundant, membrane attached signal protein 1 [Homo sapiens] |
| gi\|4506609\|ref\|NP_000 | 12.8 | | 12.8 | | 12.8 | ribosomal protein L19 [Homo sapiens] |
| gi\|89027564\|ref\|XP_94 | 8.8 | | 8.8 | | 8.8 | PREDICTED: similar to Ribosomal protein L6 isoform 7 [Homo sapiens] |
| gi\|169168181\|ref\|XP_0 | 8.1 | | 8.1 | | 8.1 | PREDICTED: hypothetical protein LOC648000 [Homo sapiens] |
| gi\|10947135\|ref\|NP_00 | 3.6 | | 3.6 | | 3.6 | ATP-binding cassette, sub-family F, member 1 isoform b [Homo sapiens] |
| gi\|18375673\|ref\|NP_00 | 2.1 | | 2.1 | | 2.1 | regulator of nonsense transcripts 1 [Homo sapiens] |

FIG. 27

| Locus | Normal | | Loose' | | Total | Description |
|---|---|---|---|---|---|---|
| | Wild Type 200mM | Mutant 200mM | Wild Type 200mM | Mutant 200mM | | |
| gi\|148746199\|ref\|NP_0 | | | | 25 | 25 | ribosomal protein L31 isoform 2 [Homo sapiens] |
| gi\|5803137\|ref\|NP_006 | | | | 21 | 21 | RNA binding motif protein 3 [Homo sapiens] |
| gi\|40806164\|ref\|NP_06 | | | | 18.8 | 18.8 | ubiquitin-conjugating enzyme E2 variant 1 isoform a [Homo sapiens] |
| gi\|34098946\|ref\|NP_00 | | | | 18.2 | 18.2 | nuclease sensitive element binding protein 1 [Homo sapiens] |
| gi\|169194577\|ref\|XP_0 | | | | 17.8 | 17.8 | PREDICTED: similar to mCG4465, partial [Homo sapiens] |
| gi\|4504347\|ref\|NP_000 | | | | 17.6 | 17.6 | alpha 1 globin [Homo sapiens] |
| gi\|38146109\|ref\|NP_93 | | | | 16.3 | 16.3 | arginine/serine-rich coiled-coil 2 isoform c [Homo sapiens] |
| gi\|169163567\|ref\|XP_0 | | | | 15.4 | 15.4 | PREDICTED: hypothetical protein [Homo sapiens] |
| gi\|18490987\|ref\|NP_05 | | | | 15.1 | 15.1 | ribosomal protein P0-like protein [Homo sapiens] |
| gi\|169171969\|ref\|XP_0 | | | | 13.2 | 13.2 | PREDICTED: similar to bCG2014184 [Homo sapiens] |
| gi\|27734727\|ref\|NP_77 | | | | 11.9 | 11.9 | coiled-coil domain containing 95 [Homo sapiens] |
| gi\|6005860\|ref\|NP_009 | | | | 11.4 | 11.4 | ribosomal protein L35 [Homo sapiens] |
| gi\|5453597\|ref\|NP_006 | | | | 9.8 | 9.8 | F-actin capping protein alpha-1 subunit [Homo sapiens] |
| gi\|5032087\|ref\|NP_005 | | | | 9.3 | 9.3 | splicing factor 3a, subunit 1, 120kDa isoform 1 [Homo sapiens] |
| gi\|4506455\|ref\|NP_002 | | | | 8.8 | 8.8 | reticulocalbin 1 precursor [Homo sapiens] |
| gi\|149193321\|ref\|NP_0 | | | | 8.3 | 8.3 | G-rich RNA sequence binding factor 1 isoform 1 [Homo sapiens] |
| gi\|18379332\|ref\|NP_56 | | | | 8.1 | 8.1 | WW domain-containing adapter with a coiled-coil region isoform 3 [Homo sapiens] |
| gi\|4759264\|ref\|NP_004 | | | | 7.9 | 7.9 | COP9 constitutive photomorphogenic homolog subunit 2 [Homo sapiens] |
| gi\|83715964\|ref\|NP_00 | | | | 7.9 | 7.9 | high-mobility group 20B [Homo sapiens] |
| gi\|14277700\|ref\|NP_00 | | | | 7.6 | 7.6 | ribosomal protein S12 [Homo sapiens] |
| gi\|151301215\|ref\|NP_0 | | | | 7.2 | 7.2 | widely-interspaced zinc finger motifs [Homo sapiens] |
| gi\|4759100\|ref\|NP_004 | | | | 7 | 7 | splicing factor, arginine/serine-rich 11 [Homo sapiens] |
| gi\|45643135\|ref\|NP_99 | | | | 6.9 | 6.9 | MORF-related gene 15 isoform 2 [Homo sapiens] |
| gi\|17978512\|ref\|NP_51 | | | | 6.8 | 6.8 | poly-U binding splicing factor 60KDa isoform a [Homo sapiens] |
| gi\|13027630\|ref\|NP_07 | | | | 6.7 | 6.7 | DiGeorge syndrome critical region protein 14 [Homo sapiens] |
| gi\|29789090\|ref\|NP_06 | | | | 6.5 | 6.5 | regulator of chromosome condensation 2 [Homo sapiens] |
| gi\|7705853\|ref\|NP_057 | | | | 6.5 | 6.5 | dynein, cytoplasmic 1, light intermediate chain 1 [Homo sapiens] |
| gi\|4826734\|ref\|NP_004 | | | | 6.3 | 6.3 | fusion (involved in t(12;16) in malignant liposarcoma) [Homo sapiens] |
| gi\|4758256\|ref\|NP_004 | | | | 6 | 6 | eukaryotic translation initiation factor 2, subunit 1 alpha, 35kDa [Homo sapiens] |
| gi\|169165559\|ref\|XP_0 | | | | 5.9 | 5.9 | PREDICTED: hypothetical protein [Homo sapiens] |
| gi\|23397427\|ref\|NP_00 | | | | 5.9 | 5.9 | synaptotagmin binding, cytoplasmic RNA interacting protein [Homo sapiens] |
| gi\|41327771\|ref\|NP_00 | | | | 5.9 | 5.9 | DEAD (Asp-Glu-Ala-Asp) box polypeptide 23 [Homo sapiens] |
| gi\|4506675\|ref\|NP_002 | | | | 5.9 | 5.9 | ribophorin 1 precursor [Homo sapiens] |
| gi\|169169393\|ref\|XP_0 | | | | 5.7 | 5.7 | PREDICTED: similar to ribosomal protein L18a isoform 1 [Homo sapiens] |
| gi\|36950991\|ref\|NP_00 | | | | 5.7 | 5.7 | nuclear receptor subfamily 2, group C, member 2 [Homo sapiens] |
| gi\|11863154\|ref\|NP_00 | | | | 5.3 | 5.3 | archain [Homo sapiens] |
| gi\|5901928\|ref\|NP_008 | | | | 5.3 | 5.3 | cleavage and polyadenylation specific factor 6, 68 kD subunit [Homo sapiens] |
| gi\|15149463\|ref\|NP_14 | | | | 5.2 | 5.2 | caldesmon 1 isoform 4 [Homo sapiens] |
| gi\|8922686\|ref\|NP_060 | | | | 5.2 | 5.2 | DDX19-like protein [Homo sapiens] |
| gi\|13994151\|ref\|NP_06 | | | | 4.9 | 4.9 | PDZ and LIM domain 1 [Homo sapiens] |
| gi\|4506449\|ref\|NP_002 | | | | 4.9 | 4.9 | RNA binding motif, single stranded interacting protein 2 [Homo sapiens] |
| gi\|24307939\|ref\|NP_03 | | | | 4.8 | 4.8 | chaperonin containing TCP1, subunit 5 (epsilon) [Homo sapiens] |
| gi\|4872920\|ref\|NP_00 | | | | 4.7 | 4.7 | liver phosphofructokinase isoform b [Homo sapiens] |
| gi\|61744481\|ref\|NP_00 | | | | 4.6 | 4.6 | solute carrier family 3 (activators of dibasic and neutral amino acid transport), member 2 isoform c [Homo sapiens] |
| gi\|5453549\|ref\|NP_006 | | | | 4.4 | 4.4 | thioredoxin peroxidase [Homo sapiens] |
| gi\|21361397\|ref\|NP_00 | | | | 4.3 | 4.3 | Rac GTPase activating protein 1 [Homo sapiens] |
| gi\|8875861\|ref\|NP_00 | | | | 4.3 | 4.3 | karyopherin alpha 1 [Homo sapiens] |
| gi\|78042577\|ref\|NP_06 | | | | 4.2 | 4.2 | MAP7 domain containing 1 [Homo sapiens] |
| gi\|15055539\|ref\|NP_00 | | | | 4.1 | 4.1 | ribosomal protein S2 [Homo sapiens] |
| gi\|5031923\|ref\|NP_005 | | | | 4 | 4 | meiotic recombination 11 homolog A isoform 1 [Homo sapiens] |
| gi\|31652236\|ref\|NP_00 | | | | 3.8 | 3.8 | cut-like homeobox 1 isoform b [Homo sapiens] |
| gi\|25777621\|ref\|NP_00 | | | | 3.6 | 3.6 | protein phosphatase 1, regulatory subunit 10 [Homo sapiens] |
| gi\|39780588\|ref\|NP_06 | | | | 3.4 | 3.4 | TSR1, 20S rRNA accumulation [Homo sapiens] |
| gi\|55770830\|ref\|NP_00 | | | | 3.4 | 3.4 | chromobox homolog 4 [Homo sapiens] |
| gi\|5981441\|ref\|NP_05 | | | | 3.3 | 3.3 | hypothetical protein LOC253725 [Homo sapiens] |
| gi\|154488858\|ref\|NP_0 | | | | 3.2 | 3.2 | RNA binding motif protein 33 isoform 1 [Homo sapiens] |
| gi\|31657094\|ref\|NP_00 | | | | 3.2 | 3.2 | anillin, actin binding protein [Homo sapiens] |
| gi\|124494238\|ref\|NP_0 | | | | 3.1 | 3.1 | myosin IC isoform a [Homo sapiens] |
| gi\|31652264\|ref\|NP_07 | | | | 3.1 | 3.1 | RNA binding motif protein 26 [Homo sapiens] |
| gi\|5454064\|ref\|NP_006 | | | | 3.1 | 3.1 | RNA binding motif protein 14 [Homo sapiens] |
| gi\|4507389\|ref\|NP_003 | | | | 3 | 3 | elongin A [Homo sapiens] |
| gi\|7669490\|ref\|NP_053 | | | | 2.9 | 2.9 | Ewing sarcoma breakpoint region 1 isoform EWS-b [Homo sapiens] |
| gi\|21071052\|ref\|NP_00 | | | | 2.8 | 2.8 | helicase-like transcription factor [Homo sapiens] |
| gi\|27886529\|ref\|NP_77 | | | | 2.8 | 2.8 | ATPase, Ca++ transporting, fast twitch 1 isoform a [Homo sapiens] |
| gi\|33620769\|ref\|NP_00 | | | | 2.8 | 2.8 | retinoblastoma-binding protein 6 isoform 1 [Homo sapiens] |
| gi\|24430146\|ref\|NP_00 | | | | 2.7 | 2.7 | nucleoporin 153kDa [Homo sapiens] |
| gi\|41152056\|ref\|NP_00 | | | | 2.7 | 2.7 | elongation factor Tu GTP binding domain containing 2 [Homo sapiens] |

FIG. 27 (Cont.)

| Locus | | | | | Description |
|---|---|---|---|---|---|
| gi|4507943|ref|NP_003 | | | 2.7 | 2.7 | exportin 1 [Homo sapiens] |
| gi|62422563|ref|NP_00 | | | 2.7 | 2.7 | p21-activated kinase 4 isoform 2 [Homo sapiens] |
| gi|11559929|ref|NP_05 | | | 2.6 | 2.6 | coatomer protein complex, subunit gamma 1 [Homo sapiens] |
| gi|147903302|ref|NP_0 | | | 2.5 | 2.5 | MAP7 domain containing 3 [Homo sapiens] |
| gi|169205613|ref|XP_0 | | | 2.5 | 2.5 | PREDICTED: similar to hCG2041215 [Homo sapiens] |
| gi|169217020|ref|XP_0 | | | 2.4 | 2.4 | PREDICTED: hypothetical protein [Homo sapiens] |
| gi|33620763|ref|NP_06 | | | 2.4 | 2.4 | sno, strawberry notch homolog 1 [Homo sapiens] |
| gi|5453832|ref|NP_006 | | | 2.4 | 2.4 | hypoxia up-regulated 1 precursor [Homo sapiens] |
| gi|55956916|ref|NP_00 | | | 2.3 | 2.3 | myosin IE [Homo sapiens] |
| gi|76572691|ref|NP_055 | | | 2.3 | 2.3 | PDS5, regulator of cohesion maintenance, homolog B [Homo sapiens] |
| gi|285589773|ref|NP_00 | | | 2.2 | 2.2 | mediator complex subunit 14 [Homo sapiens] |
| gi|70166944|ref|NP_05 | | | 2.2 | 2.2 | adenosine deaminase, RNA-specific isoform b [Homo sapiens] |
| gi|112421108|ref|NP_0 | | | 1.9 | 1.9 | capicua homolog [Homo sapiens] |
| gi|116686122|ref|NP_0 | | | 1.9 | 1.9 | kinesin family member 4 [Homo sapiens] |
| gi|117553586|ref|NP_0 | | | 1.8 | 1.8 | dedicator of cytokinesis 5 [Homo sapiens] |
| gi|115647981|ref|NP_0 | | | 1.7 | 1.7 | glutamine and serine rich 1 [Homo sapiens] |
| gi|145309300|ref|NP_1 | | | 1.7 | 1.7 | cell division cycle 2-like 5 isoform 2 [Homo sapiens] |
| gi|385569484|ref|NP_06 | | | 1.7 | 1.7 | kinesin family member 21A [Homo sapiens] |
| gi|149955929|ref|NP_98 | | | 1.7 | 1.7 | calmodulin regulated spectrin-associated protein 1-like 1 [Homo sapiens] |
| gi|123656165|ref|NP_0 | | | 1.5 | 1.5 | THO complex 2 isoform 1 [Homo sapiens] |
| gi|157739945|ref|NP_0 | | | 1.5 | 1.5 | tetratricopeptide repeat, ankyrin repeat and coiled-coil containing 2 [Homo sapiens] |
| gi|32698700|ref|NP_05 | | | 1.4 | 1.4 | PHD finger protein 8 [Homo sapiens] |
| gi|387882601|ref|NP_00 | | | 1.4 | 1.4 | bromodomain PHD finger transcription factor isoform 2 [Homo sapiens] |
| gi|85797660|ref|NP_05 | | | 1.3 | 1.3 | lirakain b1 [Homo sapiens] |
| gi|148233596|ref|NP_0 | | | 1.1 | 1.1 | LPS-responsive vesicle trafficking, beach and anchor containing [Homo sapiens] |
| gi|110349715|ref|NP_0 | | | 0.1 | 0.1 | titin isoform N2-B [Homo sapiens] |

FIG. 28

| Locus | Normal | | Loose' | | Total | Description |
|---|---|---|---|---|---|---|
| | Wild Type 200mM | Mutant 200mM | Wild Type 200mM | Mutant 200mM | | |
| gi|162844404|ref|NP_2 | | | 1.5 | | 1.5 | cell recognition protein CASPR4 isoform 1 [Homo sapiens] |
| gi|155030218|ref|NP_0 | | | 4.1 | | 4.1 | PDS5, regulator of cohesion maintenance, homolog A isoform 2 [Homo sapiens] |
| gi|4507241|ref|NP_003 | | | 2.5 | | 2.5 | structure specific recognition protein 1 [Homo sapiens] |
| gi|51745451|ref|NP_005 | | | 5.2 | | 5.2 | myocyte enhancer factor 2D [Homo sapiens] |

FIG. 29

| normal (-1 1.8 -2 2.2 -3 3.5) | | loose (-1 1.5 -2 2.0 -3 3.0) | |
|---|---|---|---|
| TRUE | Use criteria | TRUE | Use criteria |
| 1.8 | Minimum +1 XCorr | 1.5 | Minimum +1 XCorr |
| 2.2 | Minimum +2 XCorr | 2 | Minimum +2 XCorr |
| 3.5 | Minimum +3 XCorr | 3 | Minimum +3 XCorr |
| 4.5 | Minimum +4 XCorr | 4.5 | Minimum +4 XCorr |
| 0.08 | Minimum DeltCN | 0.08 | Minimum DeltCN |
| 1 | Minimum charge state | 1 | Minimum charge state |
| 4 | Maximum charge state | 4 | Maximum charge state |
| 0 | Minimum ion proportion | 0 | Minimum ion proportion |
| 1000 | Maximum Sp rank | 1000 | Maximum Sp rank |
| -1 | Minimum Sp score | -1 | Minimum Sp score |
| Include | Modified peptide inclusion | Include | Modified peptide inclusion |
| Any | Tryptic status requirement | Any | Tryptic status requirement |
| TRUE | Multiple, ambiguous IDs allowed | TRUE | Multiple, ambiguous IDs allowed |
| Ignore | Peptide validation handling | Ignore | Peptide validation handling |
| XCorr | Purge duplicate peptides by protein | XCorr | Purge duplicate peptides by protein |
| FALSE | Include only loci with unique peptide | FALSE | Include only loci with unique peptide |
| FALSE | Remove subset proteins | FALSE | Remove subset proteins |
| Ignore | Locus validation handling | Ignore | Locus validation handling |
| 0 | Minimum modified peptides per locus | 0 | Minimum modified peptides per locus |
| 10 | Minimum redundancy for low coverage loci | 10 | Minimum redundancy for low coverage loci |
| 2 | Minimum peptides per locus | 2 | Minimum peptides per locus |

FIG. 30

| Identifier | Antisense Olignonucleotide | Target Hexamer | Disease Gene |
|---|---|---|---|
| SEQ ID NO:1 | 5'- CCTAGTAAGTCAACAAGCACC -3' | ACTAGG | *OPA1* |
| SEQ ID NO:2 | 5'- TAGTAAGTCAACAAGCACC -3' | ACTAGG | *OPA1* |
| SEQ ID NO:3 | 5'- CTAGTAAGTCAACAAGCACC -3' | ACTAGG | *OPA1* |
| SEQ ID NO:4 | 5'- CCTAGTAAGTCAACAAGCAC -3' | ACTAGG | *OPA1* |
| SEQ ID NO:5 | 5'- CCTAGTAAGTCAACAAGCA -3' | ACTAGG | *OPA1* |
| SEQ ID NO:6 | 5'- CCTCCTTTCCTAAGTTCTGTT -3' | CTTAGG | *RPS6KA3* |
| SEQ ID NO:7 | 5'- CTCCTTTCCTAAGTTCTGT -3' | CTTAGG | *RPS6KA3* |
| SEQ ID NO:8 | 5'- CCTCCTTTCCTAAGTTCTGT -3' | CTTAGG | *RPS6KA3* |
| SEQ ID NO:9 | 5'- ACCTCCTTTCCTAAGTTCTGT -3' | CTTAGG | *RPS6KA3* |
| SEQ ID NO:10 | 5'- CCTCCTTTCCTAAGTTCTG -3' | CTTAGG | *RPS6KA3* |
| SEQ ID NO:11 | 5'- CCTGTGGTCCTAATTTGTAGC -3' | ATTAGG | *APC* |
| SEQ ID NO:12 | 5'- CTGTGGTCCTAATTTGTAGCT -3' | ATTAGG | *APC* |
| SEQ ID NO:13 | 5'- CTGTGGTCCTAATTTGTAGC -3' | ATTAGG | *APC* |
| SEQ ID NO:14 | 5'- CCTGTGGTCCTAATTTGTAG -3' | ATTAGG | *APC* |
| SEQ ID NO:15 | 5'- CCTGTGGTCCTAATTTGTA -3' | ATTAGG | *APC* |
| SEQ ID NO:16 | 5'- CAGCTTTAGATACCTACACAG -3' | TAGGTA | *SLC5A1* |
| SEQ ID NO:17 | 5'- GCTTTAGATACCTACACAG -3' | TAGGTA | *SLC5A1* |
| SEQ ID NO:18 | 5'- GATACCTACACAGGATGCAGC -3' | TAGGTA | *SLC5A1* |
| SEQ ID NO:19 | 5'- GCTTTAGATACCTACACAGG -3' | TAGGTA | *SLC5A1* |
| SEQ ID NO:20 | 5'- AGCTTTAGATACCTACACAGG -3' | TAGGTA | *SLC5A1* |
| SEQ ID NO:21 | 5'- CCATCAACTACTGGGATTCC -3' | GTAGTT | *COL4A3* |
| SEQ ID NO:22 | 5'- CCATCAACTACTGGGATTCCT -3' | GTAGTT | *COL4A3* |
| SEQ ID NO:23 | 5'- CCATCAACTACTGGGATTC -3' | GTAGTT | *COL4A3* |
| SEQ ID NO:24 | 5'- ATCAACTACTGGGATTCCTGG -3' | GTAGTT | *COL4A3* |
| SEQ ID NO:25 | 5'- TCAACTACTGGGATTCCTGG -3' | GTAGTT | *COL4A3* |

SEQUENCE LISTING

<160> NUMBER OF SEQ ID NOS: 32

<210> SEQ ID NO 1
<211> LENGTH: 21
<212> TYPE: DNA
<213> ORGANISM: Artificial
<220> FEATURE:
<223> OTHER INFORMATION: designed antisense oligonucleotide

```
<400> SEQUENCE: 1
cctagtaagt caacaagcac c                                              21

<210> SEQ ID NO 2
<211> LENGTH: 19
<212> TYPE: DNA
<213> ORGANISM: Artificial
<220> FEATURE:
<223> OTHER INFORMATION: designed antisense oligonucleotide

<400> SEQUENCE: 2
tagtaagtca acaagcacc                                                 19

<210> SEQ ID NO 3
<211> LENGTH: 20
<212> TYPE: DNA
<213> ORGANISM: Artificial
<220> FEATURE:
<223> OTHER INFORMATION: designed antisense oligonucleotide

<400> SEQUENCE: 3
ctagtaagtc aacaagcacc                                                20

<210> SEQ ID NO 4
<211> LENGTH: 20
<212> TYPE: DNA
<213> ORGANISM: Artificial
<220> FEATURE:
<223> OTHER INFORMATION: designed antisense oligonucleotide

<400> SEQUENCE: 4
cctagtaagt caacaagcac                                                20

<210> SEQ ID NO 5
<211> LENGTH: 19
<212> TYPE: DNA
<213> ORGANISM: Artificial
<220> FEATURE:
<223> OTHER INFORMATION: designed antisense oligonucleotide

<400> SEQUENCE: 5
cctagtaagt caacaagca                                                 19

<210> SEQ ID NO 6
<211> LENGTH: 21
<212> TYPE: DNA
<213> ORGANISM: Artificial
<220> FEATURE:
<223> OTHER INFORMATION: designed antisense oligonucleotide

<400> SEQUENCE: 6
cctcctttcc taagttctgt t                                              21

<210> SEQ ID NO 7
<211> LENGTH: 19
<212> TYPE: DNA
<213> ORGANISM: Artificial
<220> FEATURE:
<223> OTHER INFORMATION: designed antisense oligonucleotide

<400> SEQUENCE: 7
ctcctttcct aagttctgt                                                 19

<210> SEQ ID NO 8
<211> LENGTH: 20
```

```
<212> TYPE: DNA
<213> ORGANISM: Artificial
<220> FEATURE:
<223> OTHER INFORMATION: designed antisense oligonucleotide

<400> SEQUENCE: 8
cctcctttcc taagttctgt                                                  20

<210> SEQ ID NO 9
<211> LENGTH: 21
<212> TYPE: DNA
<213> ORGANISM: Artificial
<220> FEATURE:
<223> OTHER INFORMATION: designed antisense oligonucleotide

<400> SEQUENCE: 9
acctcctttc ctaagttctg t                                                21

<210> SEQ ID NO 10
<211> LENGTH: 19
<212> TYPE: DNA
<213> ORGANISM: Artificial
<220> FEATURE:
<223> OTHER INFORMATION: designed antisense oligonucleotide

<400> SEQUENCE: 10
cctcctttcc taagttctg                                                   19

<210> SEQ ID NO 11
<211> LENGTH: 21
<212> TYPE: DNA
<213> ORGANISM: Artificial
<220> FEATURE:
<223> OTHER INFORMATION: designed antisense oligonucleotide

<400> SEQUENCE: 11
cctgtggtcc taatttgtag c                                                21

<210> SEQ ID NO 12
<211> LENGTH: 21
<212> TYPE: DNA
<213> ORGANISM: Artificial
<220> FEATURE:
<223> OTHER INFORMATION: designed antisense oligonucleotide

<400> SEQUENCE: 12
ctgtggtcct aatttgtagc t                                                21

<210> SEQ ID NO 13
<211> LENGTH: 20
<212> TYPE: DNA
<213> ORGANISM: Artificial
<220> FEATURE:
<223> OTHER INFORMATION: designed antisense oligonucleotide

<400> SEQUENCE: 13
ctgtggtcct aatttgtagc                                                  20

<210> SEQ ID NO 14
<211> LENGTH: 20
<212> TYPE: DNA
<213> ORGANISM: Artificial
<220> FEATURE:
<223> OTHER INFORMATION: designed antisense oligonucleotide

<400> SEQUENCE: 14
```
cctgtggtcc taatttgtag                                           20

<210> SEQ ID NO 15
<211> LENGTH: 19
<212> TYPE: DNA
<213> ORGANISM: Artificial
<220> FEATURE:
<223> OTHER INFORMATION: designed antisense oligonucleotide

<400> SEQUENCE: 15
cctgtggtcc taatttgta                                            19

<210> SEQ ID NO 16
<211> LENGTH: 21
<212> TYPE: DNA
<213> ORGANISM: Artificial
<220> FEATURE:
<223> OTHER INFORMATION: designed antisense oligonucleotide

<400> SEQUENCE: 16
cagctttaga tacctacaca g                                         21

<210> SEQ ID NO 17
<211> LENGTH: 19
<212> TYPE: DNA
<213> ORGANISM: Artificial
<220> FEATURE:
<223> OTHER INFORMATION: designed antisense oligonucleotide

<400> SEQUENCE: 17
gctttagata cctacacag                                            19

<210> SEQ ID NO 18
<211> LENGTH: 21
<212> TYPE: DNA
<213> ORGANISM: Artificial
<220> FEATURE:
<223> OTHER INFORMATION: designed antisense oligonucleotide

<400> SEQUENCE: 18
gatacctaca caggatgcag c                                         21

<210> SEQ ID NO 19
<211> LENGTH: 20
<212> TYPE: DNA
<213> ORGANISM: Artificial
<220> FEATURE:
<223> OTHER INFORMATION: designed antisense oligonucleotide

<400> SEQUENCE: 19
gctttagata cctacacagg                                           20

<210> SEQ ID NO 20
<211> LENGTH: 21
<212> TYPE: DNA
<213> ORGANISM: Artificial
<220> FEATURE:
<223> OTHER INFORMATION: designed antisense oligonucleotide

<400> SEQUENCE: 20
agctttagat acctacacag g                                         21

<210> SEQ ID NO 21
<211> LENGTH: 20
<212> TYPE: DNA
<213> ORGANISM: Artificial

```
<220> FEATURE:
<223> OTHER INFORMATION: designed antisense oligonucleotide

<400> SEQUENCE: 21
ccatcaacta ctgggattcc                                                  20

<210> SEQ ID NO 22
<211> LENGTH: 21
<212> TYPE: DNA
<213> ORGANISM: Artificial
<220> FEATURE:
<223> OTHER INFORMATION: designed antisense oligonucleotide

<400> SEQUENCE: 22
ccatcaacta ctgggattcc t                                                21

<210> SEQ ID NO 23
<211> LENGTH: 19
<212> TYPE: DNA
<213> ORGANISM: Artificial
<220> FEATURE:
<223> OTHER INFORMATION: designed antisense oligonucleotide

<400> SEQUENCE: 23
ccatcaacta ctgggattc                                                   19

<210> SEQ ID NO 24
<211> LENGTH: 21
<212> TYPE: DNA
<213> ORGANISM: Artificial
<220> FEATURE:
<223> OTHER INFORMATION: designed antisense oligonucleotide

<400> SEQUENCE: 24
atcaactact gggattcctg g                                                21

<210> SEQ ID NO 25
<211> LENGTH: 20
<212> TYPE: DNA
<213> ORGANISM: Artificial
<220> FEATURE:
<223> OTHER INFORMATION: designed antisense oligonucleotide

<400> SEQUENCE: 25
tcaactactg ggattcctgg                                                  20

<210> SEQ ID NO 26
<211> LENGTH: 22
<212> TYPE: DNA
<213> ORGANISM: Artificial
<220> FEATURE:
<223> OTHER INFORMATION: Reporter Forward PCR primer

<400> SEQUENCE: 26
caaacagaca ccatggtgca cc                                               22

<210> SEQ ID NO 27
<211> LENGTH: 24
<212> TYPE: DNA
<213> ORGANISM: Artificial
<220> FEATURE:
<223> OTHER INFORMATION: Reporter Reverse PCR primer

<400> SEQUENCE: 27
aacagcatca ggagtggaca gatc                                             24
```

```
<210> SEQ ID NO 28
<211> LENGTH: 21
<212> TYPE: DNA
<213> ORGANISM: Artificial
<220> FEATURE:
<223> OTHER INFORMATION: SRSF6 Forward PCR primer

<400> SEQUENCE: 28
tacggcttcg tggagttcga g                                              21

<210> SEQ ID NO 29
<211> LENGTH: 22
<212> TYPE: DNA
<213> ORGANISM: Artificial
<220> FEATURE:
<223> OTHER INFORMATION: SRSF6 Reverse PCR primer

<400> SEQUENCE: 29
tcttgccaac tgcaccgact ag                                             22

<210> SEQ ID NO 30
<211> LENGTH: 25
<212> TYPE: DNA
<213> ORGANISM: Homo sapiens

<400> SEQUENCE: 30
cttaccaggt gtgattaatg taagt                                          25

<210> SEQ ID NO 31
<211> LENGTH: 19
<212> TYPE: DNA
<213> ORGANISM: Homo sapiens

<400> SEQUENCE: 31
ggactgggac aaggtgggc                                                 19

<210> SEQ ID NO 32
<211> LENGTH: 33
<212> TYPE: DNA
<213> ORGANISM: Homo sapiens

<400> SEQUENCE: 32
ccccagggag agctggtgta cgcccactac ggg                                 33
```

EXONIC SPLICING ENHANCERS AND EXONIC SPLICING SILENCERS

RELATIONSHIP TO OTHER APPLICATIONS

This application claims priority to and the benefit of U.S. provisional application No. 61/512,827 filed 28 Jul. 2011, the entirety of which is fully incorporated by reference herein.

GOVERNMENT SUPPORT CLAUSE

This invention was made with Government support under grant No. R01GM085121 from the National Institutes of Health. The Government has certain rights in this invention.

FIELD OF THE INVENTION

The invention relates to exonic splicing enhancers (ESE) and exonic splicing silencers (ESS), ESE and ESS related to disease, methods for regulating ESE and ESS, compounds for regulating ESE and ESS, methods for diagnosing disease by identifying aberrant ESE and ESS, and methods for treating disease by regulating ESE and ESS.

BACKGROUND OF THE INVENTION

The sequences of mammalian exons perform at least two overlapping roles in gene expression. First, exons are encoded with the primary sequence determinants of proteins. This information is decoded by the ribosome and translated into functional polypeptides. Secondly, exonic sequences contribute to pre-mRNA splicing through both sequence and local structure. This is not surprising given the organization of mammalian genes, which typically contain small exons (~140 bp) flanked by thousands of base-pairs of intronic DNA sequence. The large size of many mammalian genes, and the apparent degeneracy of mammalian splice sites marking the 5' and 3' termini of introns, are also suggestive of a requirement for auxiliary cis-acting elements in facilitating exon recognition.

Exonic sequences contain a staggering array of cis-acting elements that direct the activation or repression of splicing. These functional elements are classified as either exonic splicing enhancers (ESE) or silencers (ESS) based on their ability to stimulate or inhibit splicing, respectively. ESE and ESS elements, acting in concert with their cognate trans-acting RNA-binding proteins, represent important components in a splicing code that specifies how, where and when mRNAs are assembled from their precursors. Two of the major players in establishing exon identity are the serine and arginine-rich proteins (SR proteins) and the heterogeneous nuclear ribonucleoproteins (hnRNPs). SR proteins promote the initial stages of spliceosome assembly by binding to ESEs and recruiting basal splicing factors to adjacent splice sites or by antagonizing the effects of ESS elements. By contrast, hnRNPs mediate the repressive effects of silencers and can alter recruitment of the core splicing machinery. The interactions between silencers, enhancers and their cognate binding proteins play a critical role in the fidelity and regulation of pre-mRNA splicing.

At least 10% of all mutations identified as causing human inherited disease are known to alter consensus 5' or 3' splice sites, thereby inducing aberrant pre-mRNA splicing. Nonetheless, the roles played by pre-mRNA splicing in human genetic disease remain enigmatic. While the mechanistic consequences of mutations on splice sites are fairly easy to interpret, evaluating precisely how inherited disease-causing mutations influence the loss or gain of ESE/ESS motifs is more challenging. This is due in part to the considerable functional overlap between protein coding sequences and the cis-acting elements involved in splicing regulation. Hence, many missense and nonsense mutations that alter mRNA splicing may be incorrectly assumed to impact solely upon protein structure-function relationships as a consequence of amino acid substitution or protein truncation, rather than upon splicing changes per se. It is also possible that the impact of a disease allele may be due to the combination of an aberrant splicing event and the presence of a normal length mutation-bearing transcript. Such multifunctional sites within coding regions have been identified by the intragenic mapping of common single nucleotide polymorphisms (SNPs). As a consequence of purifying selection, SNPs appear somewhat depleted and synonymous codon bias restricted (GAA vs. GAG), revealing a silhouette of the "splicing code" that appears position-restricted relative to the edges of exons.

SUMMARY OF THE INVENTION

The invention encompasses methods for identification of splicing-sensitive disease mutations, and functional RNA elements as targets for amelioration of aberrant pre-mRNA splicing. Certain embodiments of the invention include methods for reducing aberrant pre-mRNA splicing in disease-related genes by interfering with ACUAGG, CUUAGG, AUUAGG, UAGGUA, GUAGUU, or other similar regulatory hexamers. The disclosed regulatory hexamers are also useful as targets for the diagnosis of diseases and conditions.

Embodiments of the invention include compounds which interact with ESE and ESS hexamers, or which specifically bind to such hexamers, or which compete with cis-acting elements for binding to such hexamers. Such compounds of the invention may comprise polynucleotides, small molecules, polypeptides, polypeptide fragments, antibodies, ribonucleoproteins, protein complexes, or ribonucleoprotein complexes. Polynucleotides of the invention may be DNA or RNA, antisense oligonucleotides, short interfering RNAs, or any of a number of nucleic acid analogs such as, for example, 2'OMe RNA, locked nucleoside analogs, phosphorodiamidate morpholino analogs, or peptide nucleic acids.

Other embodiments include methods for reducing aberrant exon splice suppression by interfering with a regulatory hexamer such as ACUAGG, CUUAGG, AUUAGG, UAGGUA, or GUAGUU. The compounds of the invention may interfere with such regulatory hexamers by specific binding, or by competing with cis-acting elements for binding. The invention contemplates reduction of aberrant exon splice suppression in cells which may comprise disease-related genes such as, for example, OPA1, PYGM, TFR2, RPS6KA3, APC, SLC5A1, and COL4A3. In certain embodiments, the function of a regulatory sequence such as ACUAGG, CUUAGG, AUUAGG, UAGGUA, or GUAGUU can be blocked without destroying the transcript (for example, via siRNA), allowing proper splicing of the endogenous gene to be restored, and leading to a full or partial rescue of the phenotype.

In the present disclosure, a cis-acting regulatory element may act in conjunction with an ESS. The cis-acting element may be defined by a polymer sequence of six ribonucleotides (RNA) which act as a binding site for a trans-factor which through direct interaction with the cis-acting element is able to alter the splicing pattern of pre-messenger RNA.

A trans-acting factor may include all protein, RNA, or ribonucleoprotein complexes which may alter pre-mRNA splicing via direct interaction with the corresponding pre-mRNA transcript.

The invention also encompasses methods for the diagnosis of diseases or conditions by identifying aberrant ESS hexamers in disease-associated genes. Examples of disease-associated genes which may be targeted by the compounds of the invention include OPA1, PYGM, TFR2, RPS6KA3, APC, SLC5A1, and COL4A3.

An embodiment of the invention is a scoring algorithm that provides a numerical expression of the relationship between disease and neutral variants and their differential distributions with regard to loss or gain of an ESE or ESS, as shown, for example, in FIG. 1. The score is a robust independent combination of the differential strength of the hexamer, plus the differential strength of that particular base in the hexamer.

BRIEF DESCRIPTION OF THE FIGURES

FIG. 1. Scoring schematic to express the relationship between disease and neutral variants and their differential distributions with respect to loss or gain of an ESE or ESS. Frequencies corresponding to HGMD and common SNP are shown. In the schematic, let t∈{ESEloss, ESEgain, ESSloss, ESSgain}, and let $S_{t,0,hgmd} \ldots S_{t,n,hgmd}$ and $S_{t,0,snp} \ldots S_{t,n,snp}$ be normalized counts plus a pseudocount for each hexamer in set t, such that:

$$\Sigma_i(S_{t,i,hgmd})=1 \text{ and } \Sigma_i(S_{t,i,snp})=1.$$

For some hexamer k in set t, let $H_{t,k,0,hgmd} \ldots H_{t,k,5,hgmd}$ and $H_{t,k,0,snp} \ldots H_{t,k,5,snp}$ be normalized counts plus a pseudocount for position 0 through 5, such that:

$$\Sigma_i(H_{t,k,i,hgmd})=1 \text{ and } \Sigma_i(H_{t,k,i,snp})=1.$$

A score γ is defined for some polymorphism affecting position j of hexamer k in set t, such that:

$$\gamma=\log_2(S_{t,k,hgmd}/S_{t,k,snp})+\log_2(H_{t,k,j,hgmd}/H_{t,k,j,snp}).$$

FIGS. 2A-2D. Patterns of gain or loss of exonic splicing regulator among pathological mutations (from HGMD) as compared to putatively neutral SNPs. In FIG. 2A and FIG. 2B, bar height corresponds to the Odds Ratio (OR) of HGMD/SNPs for the loss or gain of enhancers and silencers, respectively. Each error bar represents a two-tailed 95% confidence interval for the bar height. Directionality was expressed in the form of the ancestral state>variant for the SNPs and healthy>disease for the HGMD mutations. FIG. 2C and FIG. 2D show Principle Component Analysis (PCA) of normalized ratios of HGMD vs. SNP substitution for loss or gain of ESE and ESS hexamers, respectively. Each row corresponds to a single ESE or ESS hexamer whereas each column represents loss or gain of the hexamer by a genomic variant. Any hexamers that were not significant at the 5% level were omitted from the heat map. Each box depicts the log ratio for the counts of HGMD/SNP causing loss or gain of a specific hexamer.

Figure 3:
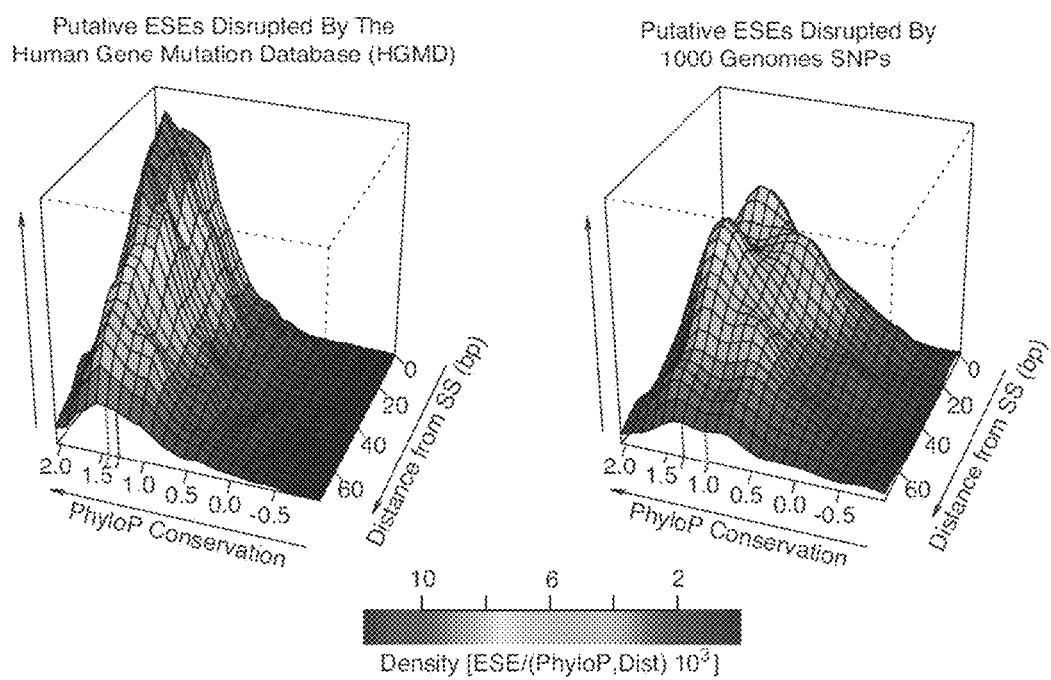

FIG. 3. Conservation of exonic splicing enhancers ablated by genomic variants. The two-dimensional density distributions (relative values) of ESEs containing associated average PhyloP scores and distances to the nearest splice site (from 3-72 bp). The density distributions for ESEs targeted for loss by inherited disease-causing (HGMD) mutations are shown in the left panel, and by neutral SNPs are shown in the right panel. On the axes showing PhyloP Conservation, the light mark designates the median PhyloP score of each density distribution and the dark mark designates a PhyloP score corresponding to a p-value of 0.05.

Figure 4A:
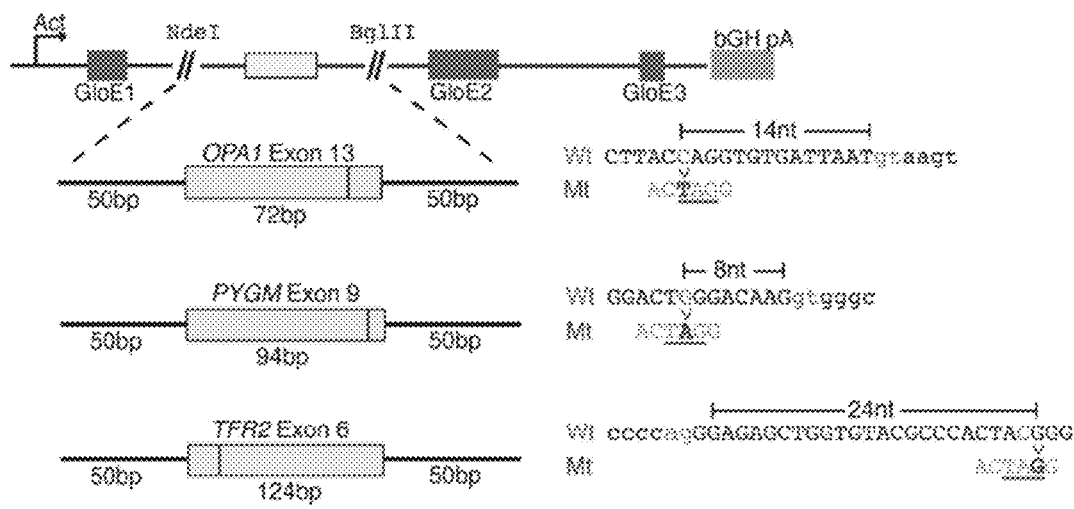
Figure 4B:
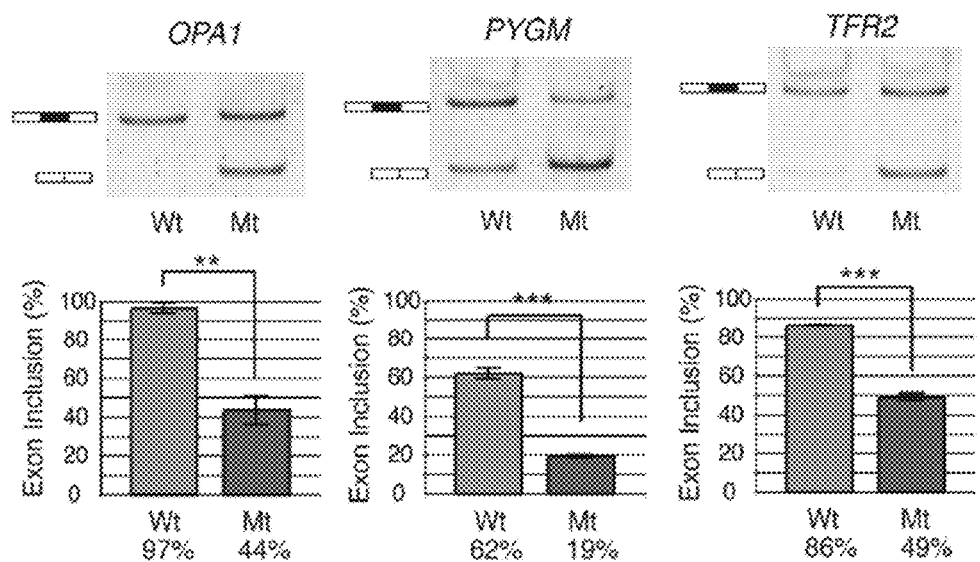

FIGS. 4A and 4B. Validation of mutations creating the enriched silencer ACUAGG using the beta hemoglobin splicing reporter. FIG. 4A shows splicing reporter constructs created from matched pairs of wild-type (Wt) or mutant (Mt) alleles that give rise to a gain of the ACUAGG silencer in constitutive exons in three different disease genes: OPA1, PYGM and TFR2. GloE1, GloE2 and GloE3 designate exons 1-3 of beta hemoglobin. The polyadenylation signal from the bovine growth hormone 1 gene is indicated by bGH pA. Wild-type allele shown above the "v", mutant allele shown below the "v", and the silencer sequence created by the mutation shown below the wild-type sequence (wild-type sequences shown of OPA1, PYGM and TFR2 are SEQ ID NO:30, SEQ ID NO:31 and SEQ ID NO:32, respectively). FIG. 4B HeLa cells were transiently transfected in triplicate with both wild-type (Wt) and mutant (Mt) alleles. Twenty-four hours after transfection, cells were treated with emetine to inhibit NMD, RNA was harvested, and the splicing efficiency determined by RT-PCR and visualized using 6% non-denaturing (29:1) polyacrylamide gel electrophoresis (PAGE). The graphs depict mean exon inclusion quantified using an Agilent 2100 Bioanalyzer with standard error bars. Statistical hypothesis testing on means was executed using a Welch t-test for normal data with unequal sample size and variance using a values of 0.05 (*), 0.01 (), and 0.001 (*).

Figure 5A:
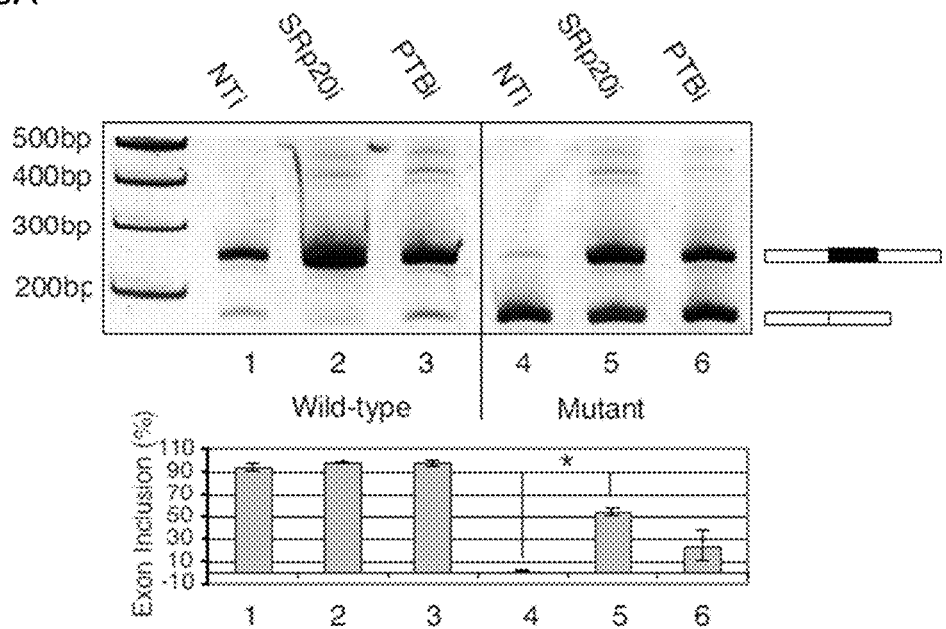
Figure 5B:
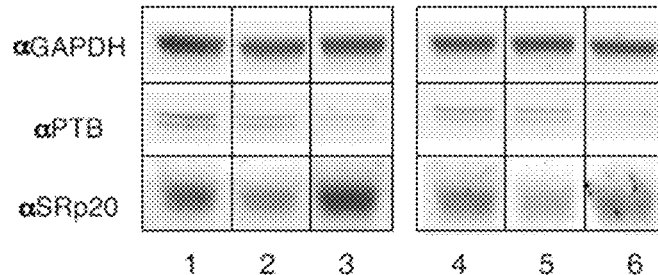
Figure 5C:
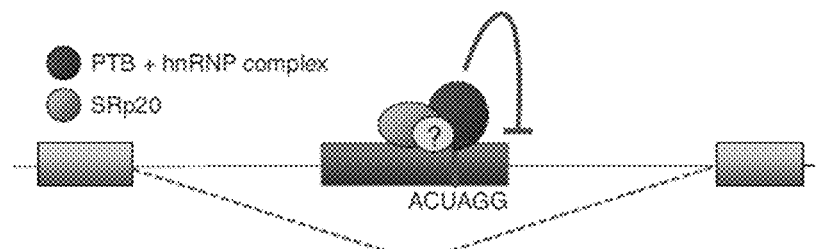

FIG. 5A-5C. Identification of trans-acting factors implicated in skipping of the ACUAGG-containing OPA1 allele. FIG. 5A RN-PCR analysis of OPA1 splicing reporters from HeLa cells cotransfected with non-targeting siRNA (NTi), SRSF3 siRNA (SRp20i), PTBP1 siRNA (PTBi). Lanes 1-3 and 4-6 are wild-type and mutant reporters, respectively. Statistical hypothesis testing on means was executed using a Welch t-test for normal data with unequal sample size and variance using a values of 0.05 (*), 0.01 (), and 0.001 (*). FIG. 5B Western blot showing relative depletion of SRp20 and PTB as compared to the GAPDH loading control. FIG. 5C Model for aberrant splicing by "ACUAGG" ESS. A point mutation creating the sequence ACUAGG results in recruitment of a silencer complex which may contain SRp20 and members of the hnRNP protein family, either directly or indirectly bound to the RNA sequence. The complex is involved in deterring inclusion of the mutant exon via mechanism(s) that still remain to be determined.

Figure 6:
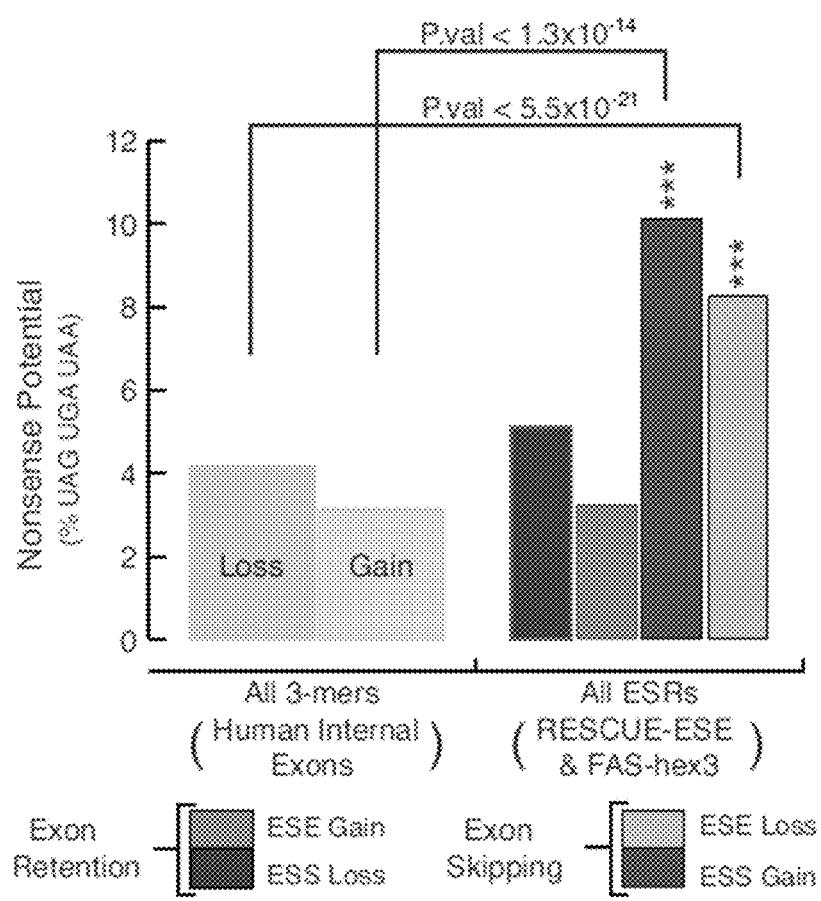

FIG. 6. Overview of the nonsense codon sequence bias in exonic splicing regulators. Bars correspond to the nonsense-coding potential of ESR loss or gain, the proportion (expressed as a percentage) of 3-mers matching UAG, UGA, or UAA out of total 3-mers. For ESR loss, this was calculated via simulated mutation based on HGMD transition/transversion probabilities. For all human internal exonic 3-mers, the nonsense-coding potential was calculated using the same algorithm as the ESRs, except using a set of all human internal exonic sequences instead of ESR hexamers. The frequencies were normalized and the values for the data given for ESR loss or gain were analyzed statistically (P-values from $\chi^2$ goodness-of-fit test) using an α value of 0.001 (***).

FIG. 7—also referred to as Table 1. Summary of putative splicing-sensitive mutations, exons, and genes associated with genetic disease.

FIG. 8—also referred to as Table 2. Summary of single nucleotide polymorphisms used in the disclosed experiments.

FIG. 9—also refereed to as Table 3. Exonic splicing enhancers significantly enriched for loss by disease-causing mutations at 5% FDR.

FIG. 10—also referred to as Table 4. Exonic splicing enhancers significantly enriched for creation by disease-causing mutations at 5% FDR, 1% FDR or 0.1% FDR.

FIG. 11—also referred to as Table 5. Exonic splicing silencers significantly enriched for loss by disease-causing mutations at 5% FDR.

FIG. 12—also referred to as Table 6. Exonic splicing silencers significantly enriched for creation by disease-causing mutations at 5% FDR.

FIG. 13—also referred to as Table 7A. RNA-binding proteins captured by wild-type and mutant RNA ligands, as identified by Multidimensional Protein Identification Technology ("MudPIT"). CONTRAST output for comparisons of peptides purified with wild-type or mutant OPA1 RNA ligands. Numbers report the percentage of residues in the protein sequence that are represented by at least one peptide passing the filtering criteria. (A) Peptides present in both samples.

FIG. 14—also referred to as Table 7B Peptides present in Mutant 200 mM (normal stringency), or both samples under loose stringency.

FIG. 15—also referred to as Table 7C Following 200 mM KCl elutions, peptides present in Healthy 200 mM (normal stringency), or both samples under loose stringency.

FIG. 16—also referred to as Table 7D Following 200 mM KCl elutions, peptides present based only on loose stringency filtering.

FIG. 17—also referred to as Table 7E Following 200 mM KCl elutions, peptides present only in elutions from Mutant RNA baits.

FIG. 18—also referred to as Table 7F Following 200 mM KCl elutions, peptides present only in elutions from Wild-type RNA baits.

FIG. 19—also referred to as Table 7G Following 200 mM KCl elutions, peptides present only in elutions from Mutant RNA baits under loose stringency.

FIG. 20—also referred to as Table 7H Following 200 mM KCl elutions, peptides present only in elutions from Healthy RNA baits under loose stringency.

FIGS. 21-28—also referred to as Tables 8A-8H. RNA-binding proteins captured by wild-type and mutant RNA ligands, as identified by Multidimensional Protein Identification Technology ("MudPIT"). CONTRAST output for comparisons of peptides purified with wild-type or mutant OPA1 RNA ligands following 1M KCl elutions. Numbers report the percentage of residues in the protein sequence that are represented by at least one peptide passing the filtering criteria.

FIG. 21—also referred to as Table 8A Peptides present in both samples.

FIG. 22—also referred to as Table 8B Peptides present in either Mutant 1M, or Healthy 1M and Mutant 1M samples, under loose stringency.

FIG. 23—also referred to as Table 8C Peptides present in either Healthy 1M, or Healthy 1M and Mutant 1M samples, under loose stringency.

FIG. 24—also referred to as Table 8D Peptides present only in Healthy 1M and Mutant 1M samples, under loose stringency.

FIG. 25—also referred to as Table 8E Peptides present only in Mutant 1M samples, under normal or loose stringency.

FIG. 26—also referred to as Table 8F Peptides present only in Healthy 1M samples, under normal or loose stringency.

FIG. 27—also referred to as Table 8G Peptides present only in Mutant 1M samples, under loose stringency.

FIG. 28—also referred to as Table 8H Peptides present only in Wild-type 1M samples, under loose stringency.

FIG. 29—also referred to as Table 9. CONTRAST criteria settings used in Multidimensional Protein Identification Technology ("MudPIT") for identification of RNA-binding proteins captured by wild-type and mutant RNA ligands.

FIG. 30—also referred to as Table 10. Antisense oligonucleotides designed to target ESS hexamers and associated disease genes.

General Representations Concerning the Disclosure

This specification incorporates by reference all documents referred to herein and all documents filed concurrently with this specification or filed previously in connection with this application, including but not limited to such documents which are open to public inspection with this specification.

Definitions

In the disclosure, the terms "a" and "an" as used herein do not denote a limitation of quantity, but rather denote the presence of at least one of the referenced items. All publications mentioned herein are incorporated by reference for all purposes to the extent allowable by law.

The terms "amino acid" and "amino acid sequence" refer to an oligopeptide, peptide, polypeptide, or protein sequence, or a fragment of any of these.

The phrase "percent identity" as applied to polynucleotide or polypeptide sequences refers to the percentage of residue matches between at least two sequences aligned using a standardized algorithm such as any of the BLAST suite of programs (e.g., blast, blastp, blastx, nucleotide blast and protein blast) using, for example, default parameters. BLAST tools are very commonly used and are available on the NCBI web site.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool set at default parameters. Such a pair of polypeptides may show, for example, at least 50%, at least 60%, at least 70%, at least 80%, at least 85%, at least 90%, at least 95%, or at least 98% or greater sequence identity over a certain defined length of one of the polypeptides.

"Amplification" relates to the production of additional copies of a nucleic acid sequence e.g., using polymerase chain reaction (PCR).

The term "antibody" refers to intact immunoglobulin molecules as well as to fragments thereof, such as Fab, F(ab')2, and Fv fragments, which are capable of binding an epitopic determinant.

The term "similarity" refers to a degree of complementarily. There may be partial similarity or complete similarity. The word "identity" may substitute for the word "similarity." A partially complementary sequence that at least partially inhibits an identical sequence from hybridizing to a target nucleic acid is referred to as "substantially similar."

The term "analog" as used herein encompasses variants and derivatives.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" or "minus" can refer to the antisense strand, and the designation "positive" or "plus" can refer to the sense strand.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml denatured salmon sperm DNA. Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al. (1989) *Molecular Cloning: A Laboratory Manual*, $2^{nd}$ ed., vol. 1-3, Cold Spring Harbor Press, Plainview N.Y.; specifically see vol. 2, ch. 9. High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic", "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein or peptide, e.g., the antigenic determinant or epitope, recognized by the binding molecule. For example, if an antibody is specific for epitope "A," the presence of a polypeptide containing the epitope A, or the presence of free unlabelled A, in a reaction containing free labeled A and the antibody will reduce the amount of labeled A that binds to the antibody. With respect to polynucleotides, the terms "specific binding" and "specifically binding" refer to that interaction between a polynucleotide and a complementary polynucleotide, an agonist, an antibody, an antagonist, a small molecule, or any natural or synthetic binding composition. The interaction is dependent upon the presence of a particular structure of the polynucleotide recognized by the binding molecule.

DETAILED DESCRIPTION OF THE INVENTION

The embodiments disclosed herein are illustrative and exemplary and are not meant to limit the invention. Other embodiments can be utilized and structural changes can be made without departing from the scope of the claims of the present invention.

The invention relates to the role of exonic splicing enhancers (ESE) and exonic splicing silencers (ESS) in disease causation, methods for identification of splicing sensitive disease mutations, and functional RNA elements as targets for amelioration of aberrant pre-mRNA splicing. The invention also encompasses methods for reducing aberrant pre-mRNA splicing in disease-related genes by interfering with a regulatory hexamer such as ACUAGG, CUUAGG, AUUAGG, UAGGUA, GUAGUU, or other similar regulatory hexamers. In alternative embodiments the method may encompass providing a compound that competes with a cis-acting element for binding at a hexamer site, for example, an ACUAGG site, a CUUAGG site, an AUUAGG site, a UAGGUA site, a GUAGUU site, or other similar sites. In certain embodiments, the function of a regulatory sequence such as ACUAGG, CUUAGG, AUUAGG, UAGGUA, GUAGUU, or other similar sequences, can be blocked without destroying the transcript (for example, via siRNA), allowing proper splicing of the endogenous gene to be restored, and leading to full or partial rescue of the phenotype.

An embodiment of the invention is a method for identifying splicing sensitive disease mutations. Statistical methods were used to develop a novel stochastic model to identify genetic variation that induces aberrant pre-mRNA splicing of disease genes. The model exploits differences in distributions of non-disease associated single nucleotide polymorphisms (SNPs) and disease-causing polymorphisms to find variation that has a statistically significant probability of altering pre-mRNA splicing of the affected gene.

Figure 1:
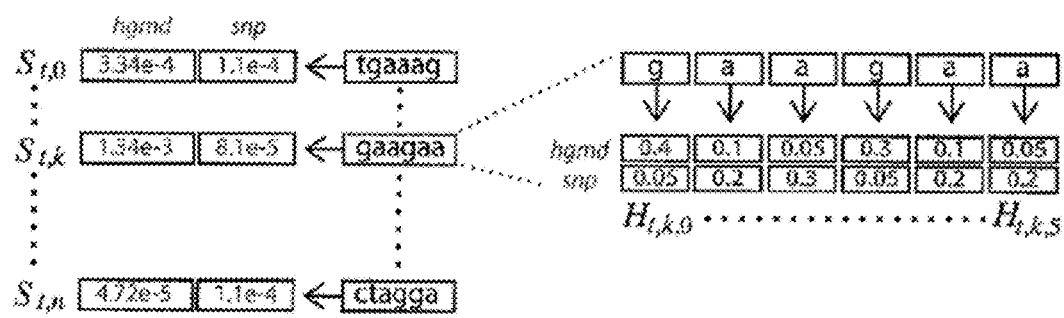

In order to predict the splicing sensitivity of a given SNP, it would be beneficial to consider the context with which the polymorphism occurs, including many splicing-sensitive features. Supervised learning methods can be utilized to perform classification based upon multiple features. Although many characteristics described in previous studies are numeric or nominal data values by default, expressing the numeric relationship between the loss/gain of a cis-element by a SNP, and splicing sensitivity, requires a more complex approach. An embodiment of the invention is the improvement on previous methodologies involving the comparison of disease-causing mutations to putatively neutral SNPs. FIG. 1 shows a schematic of a model that can be trained on the Human Gene Mutation Database (HGMD) and common 1,000 Genomes Project SNPs for either loss or gain of both ESEs and ESSs.

An embodiment of the invention provides for a numerical expression of the relationship between disease and neutral variants and their differential distributions with regard to loss or gain of an ESE or ESS, for example as shown in FIG. 1. The score is a robust independent combination of the differential strength of the hexamer, plus the differential strength of that particular base in the hexamer.

The advantages of this type of scoring method are multifold and overcome at least one major caveat of a position specific scoring matrix (PSSM) approach such as those used in ESEfinder (Cartegni, et al., *Nucleic Acids Res.* (2003) 31:3568-3571). When using PSSM to score a sequence, it is necessary to make a number of assumptions, including a possibly invalid assumption that each base is independent of every other base, and thus the sequence score is equal to the independent sum of the log scores at each position. In the case of RNA base stacking, for example, it is well known that adjacent bases may not be independent and may affect RNA stability in protein-RNA interactions. For example, for a motif that would be expressed using a single PSSM, the application of the model described in FIG. 1 may result in that motif being spread out over a number of different hexamers that are similar in sequence, thus preserving the context specific mutation of a base pair given the particular sequence around it.

An embodiment of the invention provides functional RNA elements as targets for amelioration of aberrant pre-mRNA splicing. The novel scoring model of the invention has been used to characterize the causative mechanism of disease (cis-acting element de novo creation) for about 1300 human inherited disease associated mutations whose causative mechanism is currently unknown or misunderstood. Human genomic coordinates (20-30 base pairs in length) centered upon these disease associated mutations represent novel therapeutic targets for antisense oligonucleotide based chemistries or small molecule compounds. These targets provide an avenue to ameliorate disease phenotypes through rational drug design, given an understanding of the causative mechanism for disease association of these human variants. Three such variants have been validated and support the hypothesized mechanism of action. Variants in OPA1, TFR2, and PYGM, having HGMD IDs CM080465, CM000834, and CM991088, respectively, are supported by the data provided in Sterne-Wieler et al. (*Genome Res.* (2001) 21:1563-1571), and disclosed below.

Sterne-Wieler et al. (*Genome Res.* (2001) 21:1563-1571) is fully incorporated herein by reference. In addition, the Supplemental Material for Sterne-Wieler et al. (2001), available at: http://genome.cshlp.org/content/21/10/1563/suppl/DC1, is fully incorporated herein by reference.

Materials and Methods

Dataset Preparations

Mutations from the Human Gene Mutation Database (HGMD, at http://www.hgmd.org) and SNPs (30-50% heterozygosity) from the 1000 Genomes Project (at http://www.1000genomes.org) were extracted and mapped to hg19 internal exons as annotated by the UCSC Known Gene track (Karolchik et al., *Nucleic Acids Res.* (2008) 36:D773-D779). Intersecting alleles found in both the HGMD and SNP datasets were removed from the SNP dataset. Biallelic SNPs whose ancestral allele could not be determined were also removed from the SNP dataset. Alleles mapping to within the first 3 bp from a splice site were removed from the SNP dataset due to possible splice site consensus sequence overlap. HGMD mutations were divided into subsets corresponding to the nearest splice site (5' or 3') and according to whether the mutation mapped to constitutive or alternative exons. As a quality control measure, HGMD mutations mapping past half the average HGMD exon length (144 bp) from a splice site were also removed, leaving only mutations within 3 to 72 bp from the nearest splice site.

Odds Ratios and Binomial Estimation

ESE loss was defined as an event involving a directional change from one allele to another that served to convert an ESE to neutral or to an ESS. ESE gain was defined as an event involving a change from either neutral or ESS to an ESE. The numbers of HGMD mutations or SNPs causing ESE loss/gain were counted. An odds ratio (OR) was calculated given OR=[P(event|HGMD)/(1−P(event|HGMD))]/ [P(event|SNP)/(1−P(event|SNP))], where the event can be loss or gain of a given ESE hexamer and P(loss|dataset)=1− P(gain|dataset). Odds ratios are plotted as bars, with 95% confidence intervals (two-tailed) as error bars calculated using standard methods (Pagano and Gavreau (2000) *Principles of Biostatistics*, 2nd ed., Duxbury, Calif., USA). The same assumptions and calculations were used when considering loss or gain of ESS hexamers in neutral SNP and HGMD datasets.

In order to assess the significance of the enrichment of individual ESE hexamers in the HGMD dataset as compared to the neutral SNP dataset, the binomial distribution was employed. For each hexamer i, the probability of P(HGMD [i]=k) is distributed such that HGMD[i]~Bin(n, p[i]), where HGMD[i] is a random variable corresponding to the number of mutations causing loss of a particular ESE, p[i] is the neutral background probability for the particular hexamer to be targeted for loss, and n is the total number of HGMD mutations causing loss of any ESE. The neutral background probability (p[i]) for each ESE hexamer i is calculated as the number of times a neutral SNP causes loss of i plus a pseudocount normalized over the total number of SNPs causing loss to ESEs (SNP[i]+0.5/$\Sigma_i$ (SNP[i]+0.5)). Based on large values for n and exceptionally low values for p[i], binomial p-values are approximated using the Poisson distribution such that $\lambda$[i]~np[i]. This was also applied to ESE gain and both ESS loss and ESS gain, each with their own set of neutral background probabilities. For any mutation that alters multiple ESR hexamers, only the hexamer with the lowest binomial p-value is used in statistical tests. The significance of each p-value is determined for multiple hypotheses using a Benjamini-Hochberg false discovery rate (FDR) of 5% (Benjamini and Hochberg, *J. Roy. Statist. Soc. Ser. B* (1995) 57:289-300).

Conservation of ESE Loss Hexamers

To assess the evolutionary conservation of lost ESE motifs, the average PhyloP score was calculated from multiple orthologous alignments of 46 placental mammals (Pollard et al., *Genome Res.* (2009) 20:110-121) for each ESE hexamer ablated by a directional allele. Typically, PhyloP scores are used to determine the conservation of individual sequence alignment columns between species, given a null model of neutral evolution at single nucleotide resolution. These scores in the human genome range from values as low as −13.79 to 2.94 representing the −$\log_{10}$ (p-value) to reject the null hypothesis. The average PhyloP score was used to determine the relative conservation of hexamers rather than as a strict statistical test. Using each ESE PhyloP score and its corresponding distance to the nearest exon-intron boundary, two-dimensional Gaussian kernel density estimation was performed, and the 3D density was plotted using R. To compare the distribution of PhyloP scores for ESEs disrupted by HGMD mutations to that due to chance alone, 13,000 hexamers were randomly sampled from both the HGMD- and SNP-targeted exons that did not match a hexamer in the ESE dataset. The inventors also sampled an equal size of random hexamers containing HGMD mutations which did not cause loss or gain of known ESRs. Statistical hypothesis testing on means was executed using a Welch t-test for normal data with unequal sample size and variance using a values of 0.05 (*), 0.01 (), and 0.001 (*). Given such large sample sizes, normality assumptions are approximately satisfied through the asymptotic relationship to the normal distribution provided by the central limit theorem. Additionally, we performed a non-parametric alternative, the Wilcoxon Rank Sum Test, which provided similarly significant p-values for each test shown.

Splicing Reporter Assay and RNAi

To assess the functional relevance of non-synonymous HGMD mutations to splicing, DNA inserts containing the entire exon plus 50 bp of flanking intron sequence for both the matched wild-type and mutant versions of selected mutations, flanked by NdeI and BglII restriction sites, were created using Custom Gene Synthesis (IDT, Coralville, Iowa). Test alleles were subcloned from the pSMART vector using NdeI and BglII restriction sites into the pSC14mw vector. All constructs were validated by sequencing. Splicing reporters were transiently transfected into HeLa and 293T cells in 6-well plates using Lipofectamine 2000 (Invitrogen, Carlsbad, Calif.) following the manufacturer's instructions. Cells were harvested 24 h post-transfection and cytoplasmic RNA was subsequently isolated using Tri-Reagent LS (Sigma, St. Louis, Mo.). RNA samples were converted to cDNA using GoScript (Promega, Madison, Wis.). 100 ng of cDNA was used as templates for PCR using Bullseye R-Taq (Midwest Scientific, St. Louis, Mo.). The sequences of the PCR primers used are the following: Reporter Forward, caaacagacaccatggtgcacc (SEQ ID NO:26); Reporter Reverse, aacagcatcaggagtggacagatc (SEQ ID NO:27); SRSF6 Forward, tacggcttcgtggagttcgag (SEQ ID NO:28); SRSF6 Reverse, tcttgccaactgcaccgactag (SEQ ID NO:29). Following PCR, the amplicons were purified using PURELINK micro-centrifuge columns (Invitrogen). Amplicons corresponding to alternative mRNA isoforms were separated with 6% (29:1) polyacrylamide gel electrophoresis and visualized using SYBR Safe staining (Invitrogen). Bands corresponding to exon inclusion and exclusion were cut out and validated by DNA sequencing. The linearity of the PCR reaction was confirmed by assaying splicing at increasing PCR cycles. Quantification was performed following 29 cycles of PCR. Ratios corresponding to splicing efficiencies (% exon inclusion) were used to assay the effects of single nucleotide substitutions between samples rather than the absolute amount of each product. Molar ratios of mRNA isoforms were quantified using peak integration on a DNA 1000 chip (Agilent, Santa Clara, Calif.) using an Agilent 2100 Bioanalyzer. In order to assay for activity of nonsense-mediated decay, we treated cells with 100 μg/ml emetine dihydrocholoride hydrate (Fluka, St. Louis, Mo.) 10 h before harvesting.

For the RNA interference assay, HeLa cells were transiently co-transfected with both the construct and appropriate siRNA (NTi, SRp20i, or PTBi) using DharmaFECT Duo (Thermo Scientific, Waltham, Mass.) according to the manufacturer's instructions and harvested at 48 h post-transfection. Nuclear protein was resolved on NOVEX 10% bis tris polyacryamide gels (Life Technologies, Carlsbad, Calif.) and transferred to Immobilon FL (Millipore, Billerica, Mass.) using a GENIE Blotter (Idea Scientific, St. Paul, Minn.). Antibodies corresponding to PTB (mAb BB7), SRp20 (Sigma), and GAPDH (Calbiochem, Billerica, Mass.) were visualized with fluorescent labeled secondary antibodies (GE Healthcare, Pittsburgh, Pa.) using the FluorChem Q system (Cell Biosciences, Santa Clara, Calif.). Following purification of cytoplasmic RNA using Tri-Reagent LS (Sigma), amplicons were generated using One-step RT-PCR (Invitrogen) and the following cycling program: 55° C., 30 min; 94° C., 2 min; 30 cycles of: 94° C., 30 sec; 59° C., 30 sec; 72° C., 60 sec.

RNA Affinity Chromatography

RNA affinity chromatography was performed as described in Caputi and Zahler (*J. Biol. Chem.* (2001) 276:43850-43859), with the following modifications. For the OPA1 ligands, a region 35 nt upstream and 25 nt downstream of the 5' splice site from exon 12 of the OPA1 gene was selected. Both the wild-type and mutant alleles were sequenced using Custom Gene Synthesis (IDT). RNA was transcribed in vitro using T7 RNA polymerase (Ambion, Austin, Tex.), and then gel purified from 6% (19:1) polyacrylamide gels. 1500 pmol purified RNA was oxidized by metaperiodate treatment and coupled to adipic acid dihydrazide agarose beads (Sigma). 1.5 mg HeLa nuclear extract was incubated with the beads coupled to wild-type or mutant RNA bait, washed and eluted with increasing concentrations of KCl. One half of the sample was resolved by 10% NOVEX NUPAGE gel electrophoresis (Life Technologies) and silver stained (Silver SNAP; BD Biosciences, San Jose, Calif.). The remaining half was precipitated with 20% TCA, and washed in acetone. The protein pellet was analyzed by Multidimensional Protein Identification Technology ("MudPIT"), which involves 2-dimensional chromatography separation followed by mass spectrometry. Differences in peptide coverage between the wild-type and mutant eluates were quantified using MASCOT (Perkins et al., *Electrophoresis* (1999) 20:3551-3567) and peptide spectra from each sample were compared using CONTRAST (Tabb et al., *J. Proteome Res.* (2002) 1:21-26). All peptides identified in both eluates are listed in Tables 7 and 8. Criteria settings used for CONTRAST are listed in Table 9.

Results

Disease-Causing Mutations Overlap with the Splicing Code 27,681 exonic disease-causing mutations (missense and nonsense, see Table 1) were extracted from the HGMD, a proprietary, hand-curated database requiring one or more pieces of causal evidence for inclusion (e.g., absence from normal controls, co-segregation of lesion and phenotype through pedigree, independent occurrence in an unrelated patient, etc.). For common genetic variants, 8,601 exonic single nucleotide polymorphisms (SNPs) were extracted from the 1,000 Genomes Project (Table 2). These exonic SNPs were selected for neutrality by filtering average heterozygosity to 30-50%, corresponding to a Hardy-Weinberg minor allele frequency of at least ~0.18. In addition, the ancestral allele (biallelic directionality) was determined by comparison to the chimpanzee (*Pan troglodytes*) genome.

A set of 238 hexameric sequences corresponding to the RESCUE-ESE dataset (Fairbrother et al., *Science* (2002) 297:1007-1013) and 176 hexameric sequences corresponding to the FAS-hex2 ESS dataset (Wang et al., *Cell* (2004) 119:831-845) were employed. Each set of hexanucleotides was experimentally validated to enhance or silence splicing of an alternative exon in a mini-gene context. The directionality of the substitutions, based on ancestral>variant for SNPs and wild-type>disease for HGMD mutations, was used to calculated odds ratios (OR), expressing the relative likelihoods that either disease-causing mutations or the putatively neutral polymorphisms are associated with the loss or gain of ESEs or ESSs.

FIGS. 2A and 2B show the patterns of gain or loss of exonic splicing regulator among pathological mutations (from HGMD) as compared to putatively neutral SNPs. In FIG. 2A, hexamers corresponding to exonic splicing enhancers were obtained from the RESCUE-ESE database. Each hexamer was scored for the loss or gain (de novo creation) of an ESE by the inherited disease-causing mutations (relative to the wild-type allele) or putatively neutral SNPs (relative to the ancestral allele). Whereas disruption of ESEs was found to be strongly associated with the mutations from the HGMD dataset by comparison with neutral SNPs, there was substantially less evidence for the gain of ESEs in the disease mutation dataset. In FIG. 2B, hexamers corresponding to exonic splicing silencers were obtained from the FAS-hex2 database. In contrast to the results shown in FIG. 2A, a strong association was noted between disease-causing mutations and the creation of ESS motifs in FIG. 2B. Taken together, these data suggest that exon skipping may play a key role in human inherited disease not only via the loss of exonic splicing enhancers but also via the gain of exonic splicing silencers.

Disease-Associated Alterations of the Splicing Code

To determine if specific cis-acting elements are more susceptible to disease-causing mutations than others relative to a background level ascertained by reference to putatively neutral SNPs, the binomial enrichment p-value for loss or gain of individual hexamer sequences was calculated. The distribution of genomic variants across individual hexamers from the ESE and ESS datasets was visualized using Principle Component Analysis for optimal leaf ordering. The $\log_2$ ratios of HGMD mutations versus SNPs for loss or gain of individual ESE and ESS hexamers with a binomial p-value significant at a 5% false discovery rate (FDR) are depicted in FIGS. 2C and 2D. A positive log ratio corresponds to a hexamer in a certain context that is significantly enriched in inherited disease. Alternatively, a negative log ratio represents a hexamer that is polymorphic across human populations. White boxes correspond to non-significant P-values given a false discovery rate (FDR) of 5%. In FIG. 2C, hexamer clusters corresponding to ESE-loss, ESE-loss and ESE-gain, and ESE-gain, are designated by regions i, ii and iii, respectively. In FIG. 2D, hexamer clusters corresponding to ESS-gain and ESS-loss are designated by regions i and ii, respectively. The loss/gain of SRSF1-like binding sites are labeled as GAAGAA in FIG. 2C, whereas the ACUAGG hexamer is labeled as ACUAGG in FIG. 2D.

Of the 238 ESE hexamers considered in this analysis, 106 showed no significant difference for either loss or gain by inherited disease-causing mutations relative to SNPs given the 5% FDR. Similarly, 67 out of 176 ESS hexamers were not significantly different between the HGMD and SNP datasets. For both ESEs and ESSs, the heat maps demonstrate that HGMD mutations are not uniformly distributed across all hexamers but rather are enriched in select subsets corresponding to losses or gains. For ESEs, there is the observation of not only clusters of hexamers that are both exclusively either ablated or created by disease-causing mutations (FIG. 2C, regions i and iii), but also a small subset of hexamers that are subject to a significant degree of both loss and gain by disease-causing mutations (FIG. 2C, region ii). By contrast to the ESEs, a much larger number of hexamers are significantly enriched for disease-causing mutations that create ESSs rather than abolish ESSs (FIG. 2D, compare regions i and ii). Also examined was the loss or gain of each hexamer sequence in several different contexts, including their proximity to the nearest 5' or 3' splice sites and their presence within alternative or constitutive exons. Although the general observations described in FIGS. 2C and 2D hold true, there is inconclusive evidence for a bias of hexamer loss or gain relative to either splice site or between constitutive or alternative exons.

ESEs Ablated by Disease-Causing Mutations Share Hallmarks of Functional Splicing Enhancers Since evolutionary conservation usually implies functionality, it was determined whether there were differences in average evolutionary conservation between those ESE hexamers lost as a consequence of disease-associated mutation and those lost as a result of the introduction of a neutral SNP allele. Because ESEs are more abundant in the vicinity of spliced sites, and the activity of splicing enhancers decreases with increasing distance from splice sites (Grayeley and Maniatis, *Mol. Cell* (1998) 1:765-771; Yeo et al., *Genome Biol.* (2004) 5:R74; Parmley et al., *Mol. Biol. Evol.* (2006) 23:301-309), average PhyloP scores were evaluated across alignments of 46 placental mammals for HGMD- or SNP-disrupted ESE hexamers relative to their positions within exons.

FIG. 3 shows the bivariate density distributions of ESE hexamers lost by disease-causing mutations and neutral SNPs (left and right panels, respectively). On the axes displaying PhyloP scores, a dark mark corresponds to the statistical threshold for evolutionary conservation (PhyloP score>1.3, $\alpha=0.05$) and a light mark corresponds to the median PhyloP scores for ESE hexamers. The median PhyloP score corresponding to the distribution of putative ESE hexamers ablated by disease-causing mutations is 1.42 (FIG. 3, left panel, light mark), easily exceeding the statistical threshold for evolutionary conservation. By contrast, ESE hexamers abolished by putatively neutral SNPs have much lower distributed average PhyloP scores, such that the median (1.02) is well below the statistical threshold to reject the null hypothesis of neutrally evolving sequence. Although the median distance of ESEs from splice sites is not significantly different for those disrupted by SNPs or HGMD mutations, the distribution of PhyloP scores for ESEs lost by disease-causing mutations shifts towards higher values approaching splice sites. By contrast, the distribution for ESEs disrupted by neutral SNPs is visibly shifted towards lower values near the edges of exons. Overall, the density plots in FIG. 3 indicate that ESEs targeted by disease-causing mutations exhibit a bias not only towards higher conservation values, but also with respect to a location toward the edges of exons as compared to those ESEs targeted by neutral SNPs.

Disease-causing mutations often affect conserved regions of proteins. To determine if the conservation levels observed for ESE hexamers ablated by disease-causing mutations could result as a byproduct of this bias, random hexamers that did not cause loss/gain of any ESR from HGMD mutation- or SNP-containing exons, as well as another subset which encompassed HGMD mutations, were sampled. As expected, random hexamers sampled both from HGMD exons and from those containing HGMD mutations displayed lower distributed evolutionary conservation values than the ESEs lost by HGMD mutations (median average PhyloP scores of 1.32 and 1.36 compared to 1.45, respectively; Welch test two-tailed p-value<$1.79 \times 10^{-39}$ and $3.81 \times 10^{-15}$). Furthermore, the PhyloP scores for ESEs targeted by neutral SNPs were distributed lower overall than the set of random hexamers sampled from SNP-targeted exons (median average PhyloP scores of 1.09 and 1.15, respectively; Welch test two-tailed p-value<0.039).

Functional Validation of a Splicing Silencer Mutationally Linked to 67 Different Diseases Genes In order to test the hypothesis that those exonic splicing silencers that harbor a preponderance of disease alleles could represent functionally repressive elements, the activity of one of the most significant hexamers identified by our comparison of disease-causing and neutral polymorphisms within ESSs (designated in FIG. 2D as ACUAGG; binomial p-value<$2.2 \times 10^{-16}$, from Table 6) was validated. This specific hexamer appears to have been created by a total of 83 different disease-causing mutations in 67 different genes. This list of disease-causing mutations was searched for sequences that were amenable for cloning into splicing reporter constructs, and were present in exons of near average size and splice site strength. Of the three different disease-causing mutations we selected, OPA1, PYGM and TFR2, there was no a priori evidence for any effect on splicing from in vitro analysis (Schimpf et al., *Hum. Mutat.* (2008) 29:106-112; Bruno et al., *Neuromuscul. Disord.* (1999) 9:34-37; Camaschella et al., *Nat. Genet.* (2000) 25:14-15;). However, aberrant splicing of OPA1, PYGM and TFR2 is observed in patients carrying coding and noncoding mutations at other positions in these genes (Schimpf et al., *Hum. Genet.* (2006) 118:767-771; Nogales-Gadea et al., *Hum. Mutat.* (2008) 29:277-283; Biasiotto et al., *Haematologica* (2008) 93:309-310).

Matched pairs of beta hemoglobin-based (HBB1) splicing reporter gene constructs containing the wild-type or mutant exon plus 50 bp of adjacent intron sequence were created. To investigate the effects of the ACUAGG silencer on splicing of the reporter genes, HeLa cells were transiently transfected with both wild-type or mutant constructs. Because inclusion of all three of the test exons is predicted to induce nonsense-mediated decay (NMD) by inducing an in-frame premature termination codon (PTC), we assayed splicing in the presence of the translation inhibitor emetine dihydrochloride, a potent inhibitor of NMD in vivo. After RNA isolation and conversion to cDNA, each sample was tested for reporter RNA splicing efficiency. Inhibition of NMD was confirmed by assaying the splicing of the SRSF6 pre-mRNA, an endogenous PTC-containing gene known to undergo NMD. The presence of the SRSF6 poison exon-containing mRNA shows that NMD was indeed inhibited in the emetine-positive samples. As shown in FIG. 4B, introduction of the ACUAGG hexamer resulted in a remarkable degree of exon skipping in the OPA1, PYGM and TFR2 reporters. Quantification of amplicons using an Agilent 2100 Bioanalyzer demonstrated that the ACUAGG silencer significantly decreased inclusion of the OPA1, PYGM and TFR2 test exons from 97% to 44% (p-value<$2.39 \times 10^{-3}$), 62% to 19% (p-value<$6.83 \times 10^{-4}$) and 86% to 49% (p-value<$7.62 \times 10^{-4}$), respectively (FIG. 4B). These data suggest that it is possible to predict splicing-relevant mutations based upon the statistical enrichment of hexamers in disease-associated mutation datasets.

Identification of Trans-Acting Splicing Silencers

The data presented in FIG. 5 suggest that the ACUAGG motif functions as a strong splicing silencer. Splicing silencers have been shown to interact with trans-acting factors such as hnRNPs and to alter the kinetics of the non-rate limiting steps of spliceosome assembly when two 5' splice sites are in competition (Zhu et al., *Mol. Cell* (2001) 8:1351-1361; Yu et al., *Cell* (2008) 135:1224-1236). Given that activation of cryptic 5' splice sites in the mutant OPA1 construct was not observed, potential trans-acting factors were searched for by RNA affinity chromatography using HeLa nuclear extracts. RNA-binding proteins captured by the wild-type and mutant RNA ligands at low and high stringency were identified by Multidimensional Protein Identification Technology "MudPIT" (Tables 7, 8 and 9). At both high and low concentrations of KCl, peptides corresponding to SRp20 (SRSF3), PTB (PTBP1), hnRNP D (HNRNPD) and hnRNP L (HNRNPL) were present on the mutant RNA ligand (Tables 7 and 8), suggesting that these proteins may play a role in mediating the silencing activity of the ACUAGG hexamer.

To test the role of SRp20 and PTB in splicing silencing, HeLa cells were co-transfected with either the wild-type or mutant OPA1 splicing reporter and siRNA targeting SRp20, PTB or a non-targeting duplex. In cells transfected with non-targeting control siRNA, the mutant OPA1 reporter was inefficiently spliced relative to the wild-type reporter (FIG. 5A, compare lanes 1 and 4). By contrast, depletion of SRp20 and, to a lesser extent, PTB partially rescued inclusion of the mutant OPA1 exon (FIG. 5A, compare lane 4 with lanes 5 and 6). Quantification of the RT-PCR amplicons from duplicate experiments revealed that depletion of SRp20 and PTB restored inclusion of the mutant exon to ~50% and ~25% of the wild-type levels, respectively. Analysis of the exon inclusion ratios for the SRp20 and PTB depletion revealed that only knock down of SRp20 resulted in statistically significant changes relative to the control (FIG. 5B). Depletion of both SRp20 and PTB was confirmed by fluorescent western blot analysis of nuclear extracts prepared from transfected cells (FIG. 5B). Quantification of the western blots revealed ~2-fold and 2.75-fold depletions of SRp20 and PTB, respectively, relative to cells transfected with non-targeting control duplex. Taken together, these data implicate SRp20 and PTB in both the recognition and function of the ACUAGG exonic splicing silencer motif.

Potential Nonsense Sequences are Enriched in ESR Hexamers

Nonsense-associated altered splicing (NAS) describes the phenomenon whereby exons encoding premature stop codons tend to be excluded from the mature RNA transcript during pre-mRNA splicing in the nucleus. Although the primary mechanism of NAS is still unknown, several different models have been proposed. These include a nuclear scanning model that invokes the action of a frame-sensitive mechanism in pre-mRNA splicing (Wang et al., *Mol. Cell* (2002) 10:951-957). Alternatively, NAS may be the direct result of ESE disruption as a means to abolish exon recognition (Shiga et al., *J. Clin. Invest.* (1997) 100:2204-2210; Liu et al., *Nat. Genet.* (2001) 27:55-58). In order for nonsense mutations to be specifically associated with the loss/gain of ESR sequences, there must be a sequence bias in the ESRs themselves. To investigate this hypothesis for ESR loss, mutations were simulated based on the transition/transversion rates observed for the 14,771 exonic HGMD mutations located near the edges of exons. For the ESR gains, the proportion of nonsense 3-mers (UAG, UAA, UGA) were evaluated compared to all of the 3-mers within the corresponding hexamers. As a control for the experiment, the same algorithm was used to evaluate the "loss" or "gain" of all 3-mers (excluding the first 3 bp) in a previously used set of 206,029 human internal exons (FIG. 6; Fairbrother et al., *PLoS Biol.* (2004) 2:E268). Using these data, we compared the nonsense potential of exon retention to exon skipping with respect to that of our control.

For all ESR hexamers in our datasets, we observed at least a ~2-fold increase in nonsense-potential consistent with silencer gains (p-value<$5.50\times10^{-21}$) and enhancer losses (p-value<$1.27\times10^{-14}$) when compared to controls ($\chi^2$ goodness-of-fit test, FIG. 6). As expected, minimal values of nonsense-potential were observed for silencer loss (p-value: <0.19) and enhancer gain (p-value<0.86), consistent with the nonsense-potential seen for the respective "loss" and "gain" of all human exonic 3-mers ($\chi^2$ goodness-of-fit test, FIG. 6). The lack of nonsense-potential for enhancer gain is not surprising given the abundance of enhancers within exons, and their being subject to protein coding restrictions. These data therefore support a model that involves the disruption of enhancers and the creation of silencers to yield nonsense-associated altered splicing (NAS). Consistent with this postulate, it would appear as though enhancer loss and silencer gain are specifically associated with potential-nonsense codons through the sequence bias of the ESRs.

Discussion

The results presented here demonstrate that nearly ~25% (7,154/27,681) of exonic (i.e. missense and nonsense) mutations that cause human inherited disease are likely to induce exon skipping either via the loss of evolutionarily conserved splicing enhancers or alternatively through the creation of potent splicing silencers (Table 2). Given that it has already been recognized that at least 10% of disease-causing mutations ablate 5' or 3' splice site consensus sequences (Krawczak et al., *Hum. Mutat.* (2007) 28:150-158), a conservative estimate is that approximately one third of disease-causing mutations may induce aberrant splicing. An independent strategy has reached a similar estimate (22%) of splicing sensitive missense/nonsense disease-causing mutations (Lim et al., *Proc. Natl. Acad. Sci. USA* (2011) 108:11093-11098). Future studies that include mutations which affect intronic cis-elements may well increase this proportion. Overall, the results provide new insights into the underlying mechanisms that link mutation-induced aberrant splicing and human inherited disease. Understanding these mechanisms is a prerequisite for the optimization of treatment regimens as we enter the era of personalized medicine.

One surprising and unexpected result is that although genomic variants that create ESEs or abolish ESSs are more frequently associated with neutral SNPs (FIGS. 2A and 2B), some individual ESE and ESS hexamers show a remarkable enrichment for disease-causing mutations when gained or lost, respectively. This class of mutations may induce aberrant splicing of adjacent exons, such as observed for a polymorphism in the MSTIR1 gene (Ghigna et al., *Mol. Cell* (2005) 20:881-890). It is notable that specific ESR hexamers, based on their HGMD/SNP log ratios, appear to be disproportionately represented by disease-causing mutations (FIG. 2C, Region i and FIG. 2D, Region i). Within each of these clusters there are individual hexamers that appear to be mutated very frequently in genetic disease, suggesting that specific trans-acting factors may be associated with several genetic disorders. For example, one of the sequences in the enhancer loss-enriched cluster displays a remarkable degree of similarity to the canonical binding site for the splicing factor SF2/ASF (SRSF1) (Tacke et al., *EMBO J.* (1995) 14:3540-3551; Sanford et al., *Genome Res.* (2009) 19:381-394) (FIG. 2C. GAAGAA). Indeed, the presence of an SF2/ASF consensus motif in this cluster supports previous evidence for the loss of ESEs as an important cause of human inherited disease (Sanford et al., ibid). There are a striking number of ESEs and ESSs that are relatively untouched by disease-causing mutations, but appear to be more polymorphic in different human populations. These data suggest at least two non-mutually exclusive possibilities. The first is that those hexamers that are over-represented in the SNP dataset may be redundant with the function of other hexamers and hence more prone to variation across human populations. Alternatively, the polymorphic ESRs identified here may be associated with allele-specific alternative splicing that confers a gain of fitness rather than a disease phenotype (Fraser and Xie, *Genome Res.* (2009) 19:567-575).

An investigation was carried out to determine the function of a specific ESS hexamer, ACUAGG (FIG. 2D), that has been created de novo by no fewer than 83 different single nucleotide substitutions (both missense and nonsense) in 67 different genes as a cause of human inherited disease (Table 6). Reporter constructs derived from three different disease genes, OPA1, TFR2 and PYGM, all demonstrated that ACUAGG promotes skipping of test exons derived from the mutant alleles of each gene. A reporter construct, corresponding to an ACUAGG introduction near the 3' splice site of exon 13 from MYH7, was prepared. This mutation failed to induce appreciable skipping of the test exon. For the case of ACUAGG insertion in OPA1, the effects of this ectopic silencer element on exon skipping appear to be mediated, at least in part, by SRp20 and possibly PTB. This is surprising since SR proteins are typically thought to promote exon inclusion by binding to splicing enhancers (Ram and Ast, *Trends Genet.* (2007) 23:5-7). It is possible that interactions between SRp20, PTB and other hnRNPs create an exon silencing complex that promotes exon skipping. A comprehensive analysis of PTB-RNA interactions identified many examples of alternative cassette exons that are skipped through the action of PTB-binding sites located near the 5' splice site (Xue et al., *Mol. Cell* (2009) 36:996-1006). The present data suggests that the ACUAGG hexamer is a potent splicing silencer that functions at both 5' and 3' splice sites.

The impact of premature termination (nonsense) codons upon gene expression remains an important consideration in the elucidation of the pathogenic basis of disease-causing mutations. It is well established that the NMD pathway plays a central role in preventing the accumulation and translation of nonsense-containing mRNA isoforms (Maquat, *Nat. Rev. Mol. Cell Biol.* (2004) 5:89-99; McGlincy and Smith, *Trends Biochem. Sci.* (2008) 33:385-393). However, PTCs are also suggested to directly influence alternative splicing decisions (Wang et al., *Mol. Cell* (2002) 10:951-957; Wachtel et al., *RNA* (2004) 10:1740-1750). The most plausible model is that PTCs disrupt ESEs and induce exon skipping (Liu et al., *Nat. Genet.* (2001) 27:55-58; Cartegni et al., *Nat. Rev. Genet.* (2002) 3:285-298; Pagani et al., *J. Biol. Chem.* (2003) 278:26580-26588; Zatkova et al., *Hum. Mutat.* (2004) 24:491-501). The results presented in FIG. 5 extend this model by suggesting that such a surveillance mechanism might evolve via the acquisition of ESR sequences to counteract PTC-containing exons associated with a greater likelihood of skipping. The apparent bias of ESR sequences towards potential nonsense codons would appear to be the most logical explanation for nonsense-associated altered splicing (Valentine and Heflich, *RNA* (1997) 3:660-676). To test this postulate, the inventors examined the very first observation of NAS where exon skipping was observed in the fibrillin (FBN1) gene due to a nonsense-causing T>G transversion 26 bp from a constitutive 3' splice site (Dietz et al., *Science* (1993) 259:680-683). Consistent with the model of the inventors, the mutation appears to create a disease-enriched silencer CU<u>UAG</u>G (Table 6, binomial p-value<$2.2\times10^{-16}$), with the core of the motif containing the previously observed nonsense codon, UAG. It is suspected that many NAS observations may be consistent with this model due to ESR sequence bias or else attributable to PCR amplification artifacts after NMD (Cartegni et al., ibid). It remains to be determined if such a mechanism might arise as an attempt to preserve the transcript at the expense of a single exon or as a hammer to ensure that NMD is successfully elicited by the PTC.

Regulation of ESE and ESS

The invention provides compounds and methods for reducing aberrant pre-mRNA splicing in disease-related genes by interfering with a regulatory hexamer such as ACUAGG, CUUAGG, AUUAGG, UAGGUA, GUAGUU, or other similar regulatory hexamers. In alternative embodiments the method may encompass providing a compound that competes with a cis-acting element for binding at a hexamer site, for example, an ACUAGG site, a CUUAGG site, an AUUAGG site, a UAGGUA site, a GUAGUU site, or other similar sites. In certain embodiments, the function of a regulatory sequence such as ACUAGG, CUUAGG, AUUAGG, UAGGUA, GUAGUU, or other similar sequences, can be blocked without destroying the transcript (for example, with compounds such as siRNA), allowing proper splicing of the endogenous gene to be restored, and leading to full or partial rescue of the phenotype.

The invention provides compounds which may comprise polynucleotides, examples of which are described in Table 10. Such polynucleotides may be DNA (deoxyribonucleic acid, with thymine bases in place of uracil bases) or RNA (ribonucleic acid, with uracil bases in place of thymine bases). In alternative embodiments, the polynucleotides of the invention are antisense oligonucleotides. In alternative embodiments, the polynucleotides of the invention are short interfering RNAs which may, for example, function via RNA interference. In alternative embodiments, a polynucleotide of the invention may comprise one or more DNA monomers, may comprise one or more RNA monomers, may comprise one or more 2'OMe RNA (2'-O-methyl ribonucleic acid) monomers, may comprise one or more phosphorothioate-backbone connected nucleic acids, may comprise one or more LNA (locked nucleoside analog; U.S. Pat. No. 6,794,499) monomers, may comprise one or more PMO (phosphorodiamidate morpholino) monomers, or may comprise one or more PNA (peptide nucleic acid) monomers.

In alternative embodiments, the compounds of the invention may comprise small molecules, proteins, polypeptides, polypeptide fragments, antibodies, protein complexes, ribonucleoproteins, or ribonucleoprotein complexes. In alternative embodiments, such compounds may comprise potential trans-acting factors such as SR proteins, SRp20, PTB, hnRNP D or hnRNP L; or polypeptide fragments of SR proteins, SRp20, PTB, hnRNP D or HNRNP L.

The invention provides methods for reducing aberrant exon splice suppression by interfering with a regulatory hexamer such as ACUAGG, CUUAGG, AUUAGG, UAGGUA, GUAGUU, or other similar regulatory hexamers. Such methods may comprise: (1) providing a cell comprising a regulatory hexamer, (2) providing a compound that interacts with the regulatory hexamer, and (3) contacting the regulatory hexamer with the compound. In alternative embodiments, such methods may be used to regulate exonic splicing, to enhance exonic splicing, to silence exonic splicing, or to suppress exonic splicing. In further embodiments, such methods may be used to regulate the function of ESE hexamers, or to regulate the function of ESS hexamers. In alternative embodiments, the compounds used in such methods may bind specifically to the regulatory hexamer, or may compete with a cis-acting element for binding with the regulatory hexamer.

The invention provides methods for reducing aberrant pre-mRNA splicing by interfering with a regulatory hexamer such as ACUAGG, CUUAGG, AUUAGG, UAGGUA, GUAGUU, or other similar regulatory hexamers. Such methods may comprise: (1) providing a cell comprising a cis-acting element, (2) providing a compound that interacts with the cis-acting element, and (3) contacting, or directly competing for contact with, the cis-acting element with the compound. In alternative embodiments, such methods may be used to regulate exonic splicing, to enhance exonic splicing, to silence exonic splicing, or to suppress exonic splicing. In further embodiments, such methods may be used to regulate the function of ESE hexamers, or to regulate the function of ESS hexamers. In alternative embodiments, the compounds used in such methods may bind specifically to the regulatory hexamer, or may compete with a cis-acting element for binding with the regulatory hexamer.

The invention provides methods to diagnose a disease or condition, or to identify an individual having a disease or condition, or to identify a cell having a genetic predisposition to a disease or condition. Such methods may comprise: (1) providing a cell comprising a disease-related gene, (2) providing a compound that binds specifically to the disease-related gene having an aberrant regulatory ESS or ESE hexamer, and (3) detecting specific binding of the compound to the gene. In alternative embodiments, such methods may comprise: (1) providing the RNA from a cell, (2) providing a compound that binds specifically to a disease-related gene having an aberrant regulatory ESS or ESE hexamer, and (3) detecting specific binding of the compound to the RNA.

In alternative embodiments, the diagnostic methods of the invention are directed to the detection of the ACT JAGG hexamer in the OPA1 gene. Such methods may be used to diagnose a disease or condition such as, for example, optic neuropathy, optic atrophy type 1, deafness, autosomal dominant optic atrophy, autosomal dominant optic atrophy-plus syndrome, vision loss, hearing loss, progressive external ophthalmoplegia, ataxia, motor neuropathy, sensory neuropathy, or myopathy. Examples of compounds used to detect the ACUAGG hexamer in the OPA1 gene are compounds comprising polynucleotides comprising a sequence selected from the group consisting of SEQ ID NO:1, SEQ ID NO:2, SEQ ID NO:3, SEQ ID NO:4, and SEQ ID NO:5.

In alternative embodiments, the diagnostic methods of the invention are directed to the detection of the ACUAGG hexamer in the PYGM gene. Such methods may be used to diagnose a disease or condition such as, for example, glycogen storage disease, glycogen storage disease type V, exercise intolerance, rhabdomyolysis, or myoglobinuria.

In alternative embodiments, the diagnostic methods of the invention are directed to the detection of the ACUAGG hexamer in the TFR2 gene. Such methods may be used to diagnose a disease or condition such as, for example, hemochromatosis, iron overload disorder, arthritis, liver disease, diabetes, or heart abnormalities.

In alternative embodiments, the diagnostic methods of the invention are directed to the detection of the CUUAGG hexamer in the RPS6KA3 gene. Such methods may be used to diagnose a disease or condition such as, for example, Coffin-Lowry syndrome, X-linked intellectual disability, short stature, microcephaly, kyphoscoliosis, or skeletal abnormalities. Examples of compounds used to detect the CUUAGG hexamer in the RPS6KA3 gene are compounds comprising polynucleotides comprising a sequence selected from the group consisting of SEQ ID NO:6, SEQ ID NO:7, SEQ ID NO:8, SEQ ID NO:9, and SEQ ID NO:10.

In alternative embodiments, the diagnostic methods of the invention are directed to the detection of the AUUAGG hexamer in the APC gene. Such methods may be used to diagnose a disease or condition such as, for example, cancer, colon cancer, stomach cancer, familial adenomatous polyposis, Turcot syndrome, or attenuated familial adenomatous polyposis. Examples of compounds used to detect the AUUAGG hexamer in the APC gene are compounds comprising polynucleotides comprising a sequence selected from the group consisting of SEQ ID NO:11, SEQ ID NO:12, SEQ ID NO:13, SEQ ID NO:14, and SEQ ID NO:15.

In alternative embodiments, the diagnostic methods of the invention are directed to the detection of the UAGGUA hexamer in the SLC5A1 gene. Such methods may be used to diagnose a disease or condition such as, for example, metabolic disorders, glucose-galactose malabsorption, acidosis, glucosuria, or kidney disorders. Examples of compounds used to detect the UAGGUA hexamer in the SLC5A1 gene are compounds comprising polynucleotides comprising a sequence selected from the group consisting of SEQ ID NO:16, SEQ ID NO:17, SEQ ID NO:18, SEQ ID NO:19, and SEQ ID NO:20.

In alternative embodiments, the diagnostic methods of the invention are directed to the detection of the GUAGUU hexamer in the COL4A3 gene. Such methods may be used to diagnose a disease or condition such as, for example, Alport syndrome, nephropathy, thin basement membrane nephropathy, Goodpasture syndrome, kidney disorders, anti-glomerular basement membrane nephritis, hematuria, proteinuria, end-stage renal disease (ESRD), hearing loss, or anterior lenticonus. Examples of compounds used to detect the GUAGUU hexamer in the COL4A3 gene are compounds comprising polynucleotides comprising a sequence selected from the group consisting of SEQ ID NO:21, SEQ ID NO:22, SEQ ID NO:23, SEQ ID NO:24, and SEQ ID NO:25.

The invention provides methods to treat a disease or condition. Such methods may comprising providing an effective amount of a compound to a patient, wherein the compound interacts with an aberrant ESE or ESS regulatory hexamer. In alternative embodiments, the compounds used in such methods may bind specifically to the regulatory hexamer, or may compete with a cis-acting element for binding with the regulatory hexamer.

The invention claimed is:

1. A pharmaceutical composition comprising a polynucleotide or analog thereof, wherein the polynucleotide comprises a sequence that binds a hexamer ACUAGG, wherein binding of the polynucleotide to the hexamer interferes with aberrant splicing of a disease related gene caused by a single nucleotide mutation, and wherein the polynucleotide comprises a 2'-O-methyl ribonucleic acid, a locked nucleoside analog, a phosphorodiamidate morpholino nucleotide, or a peptide nucleic acid.

2. The pharmaceutical composition of claim 1, wherein the polynucleotide comprises a sequence that is complementary to the hexamer ACUAGG.

3. The pharmaceutical composition of claim 1, wherein the polynucleotide is between 19 and 21 nucleotides in length.

4. The pharmaceutical composition of claim 3, wherein the polynucleotide comprises a sequence of any one of SEQ ID NOs: 1-5.

5. The pharmaceutical composition of claim 1, wherein the single nucleotide mutation occurs within 3-72 bases from the nearest splice site.

* * * * *